(12) United States Patent
Chen et al.

(10) Patent No.: US 12,203,077 B2
(45) Date of Patent: *Jan. 21, 2025

(54) FUSION PROTEINS FOR IMPROVED PRECISION IN BASE EDITING

(71) Applicant: ShanghaiTech University, Shanghai (CN)

(72) Inventors: Jia Chen, Shanghai (CN); Xingxu Huang, Shanghai (CN); Li Yang, Shanghai (CN); Bei Yang, Shanghai (CN); Xiaosa Li, Shanghai (CN); Ying Wang, Shanghai (CN); Yajing Liu, Shanghai (CN)

(73) Assignee: ShanghaiTech University, Shanghai (CN)

(*) Notice: Subject to any disclaimer, the term of this patent is extended or adjusted under 35 U.S.C. 154(b) by 712 days.

This patent is subject to a terminal disclaimer.

(21) Appl. No.: 16/640,337

(22) PCT Filed: Aug. 28, 2018

(86) PCT No.: PCT/CN2018/102750
§ 371 (c)(1),
(2) Date: Feb. 19, 2020

(87) PCT Pub. No.: WO2019/042284
PCT Pub. Date: Mar. 7, 2019

(65) Prior Publication Data
US 2020/0354729 A1  Nov. 12, 2020

(30) Foreign Application Priority Data
Sep. 1, 2017 (WO) .............. PCT/CN2017/100131

(51) Int. Cl.
C12N 9/22 (2006.01)
C07K 14/32 (2006.01)
C12N 9/78 (2006.01)
C12N 15/10 (2006.01)
C12N 15/79 (2006.01)

(52) U.S. Cl.
CPC .......... C12N 15/79 (2013.01); C07K 14/32 (2013.01); C12N 9/22 (2013.01); C12N 9/78 (2013.01); C12N 15/102 (2013.01); C07K 2319/09 (2013.01); C12Y 305/04005 (2013.01)

(58) Field of Classification Search
CPC . C12N 15/79; C12N 9/22; C12N 9/78; C12N 15/102; C07K 14/32; C07K 2319/09; C07K 2319/00; C12Y 305/04005
See application file for complete search history.

(56) References Cited

U.S. PATENT DOCUMENTS

2015/0165054 A1   6/2015   Liu et al.
2019/0010481 A1*  1/2019   Joung ............... C12N 9/22

FOREIGN PATENT DOCUMENTS

| CN | 105934516 A | 9/2016 |
|---|---|---|
| CN | 106916852 A | 7/2017 |
| WO | 2017015015 A1 | 1/2017 |
| WO | 2017070632 A2 | 4/2017 |
| WO | WO2017070633 A2 | 4/2017 |
| WO | WO2017096328 A1 | 6/2017 |
| WO | 2017184768 A1 | 10/2017 |
| WO | 2018010516 A1 | 1/2018 |
| WO | 2018039438 A1 | 3/2018 |
| WO | 2018119359 A1 | 6/2018 |
| WO | 2019161783 A1 | 8/2019 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Gao et al., Cell Research 26:901-913, 2016.*
Staahl et al., Nature Biotechnology 35(5):431-434, published online Feb. 13, 2017.*
Wang et al., Cell Research 27:1289-1292, published online Aug. 29, 2017.*
Chen et al., Cell Discovery 6:62, 2020.*
Extended European Search Report for EP Application No. 18852218.9 dated Jun. 22, 2021, 8 pages.
International Search Report and Written Opinion for PCT/CN2018/102750 dated Nov. 21, 2018, 6 pages.
Li et al. "Base editing with a Cpf1-cytidine deaminase fusion", Nature Biotechnology, vol. 36, No. 4, Mar. 19, 2018, pp. 324-327.
Mitsunobu et al., "Beyond Native Cas9: Manipulating Genomic Information and Function", Trends in Biotechnology, Elsevier Publications, Cambridge, GB, vol. 35, No. 10, Jul. 21, 2017, pp. 983-996.
Wang et al., "Enhanced based editing by co-expression of free uracil DNA glycosylase inhibitor", Cell Research, vol. 27, No. 10, Aug. 29, 2017, pp. 1289-1292.

* cited by examiner

*Primary Examiner* — Delia M Ramirez
(74) *Attorney, Agent, or Firm* — Sheppard Mullin Richter & Hampton LLP

(57) ABSTRACT

Provided are base editors containing a cytidine and a catalytically inactive version of Lachnospiraceae bacterium Cpf1 (LbCpf1). The new base editors have greatly improved editing efficiency and fidelity as compared to Cas9-based base editors, and have different editing windows.

13 Claims, 32 Drawing Sheets
Specification includes a Sequence Listing.

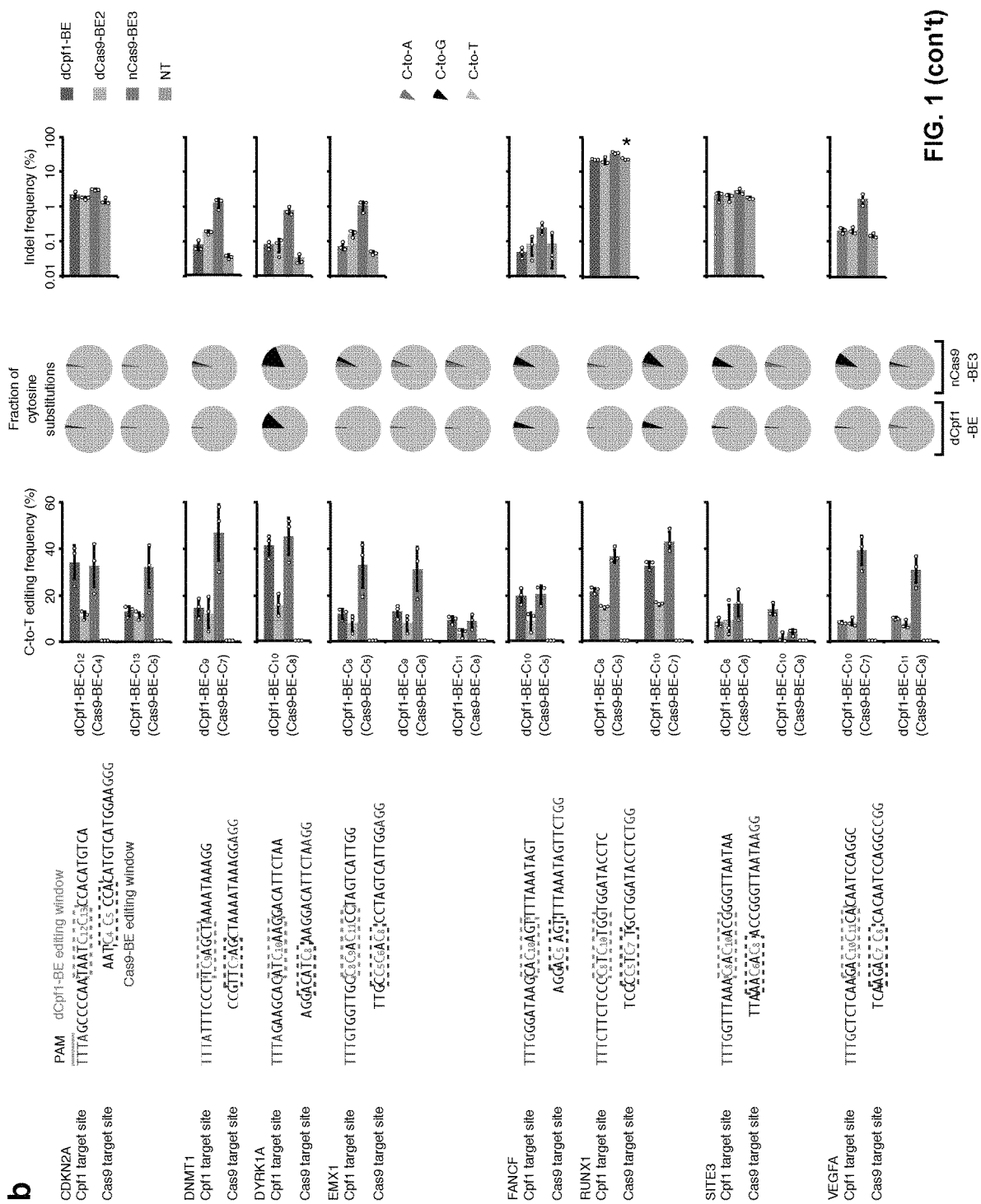
FIG. 1 (con't)

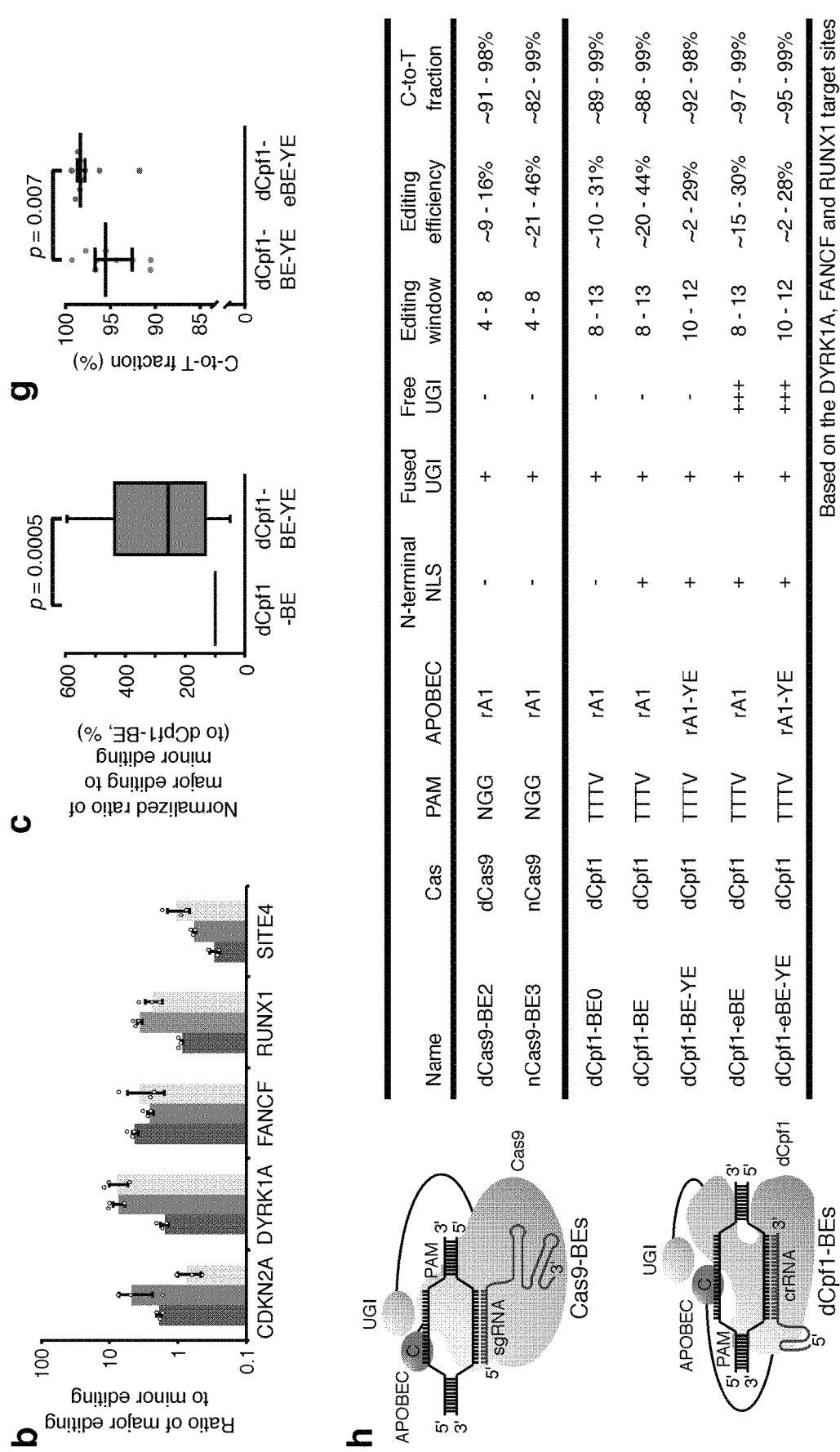
FIG. 2 (con't)

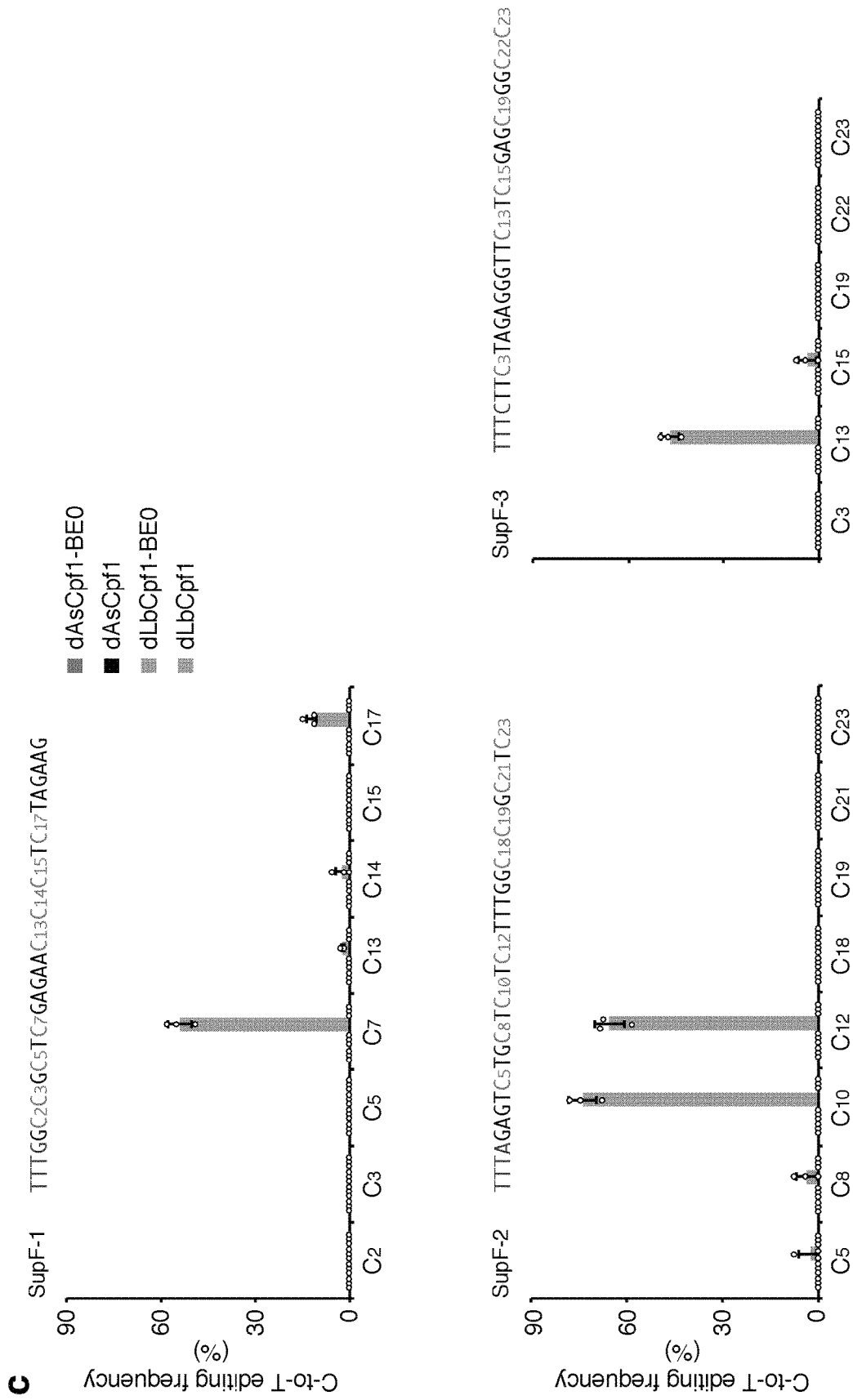
FIG. 3 (cont't)

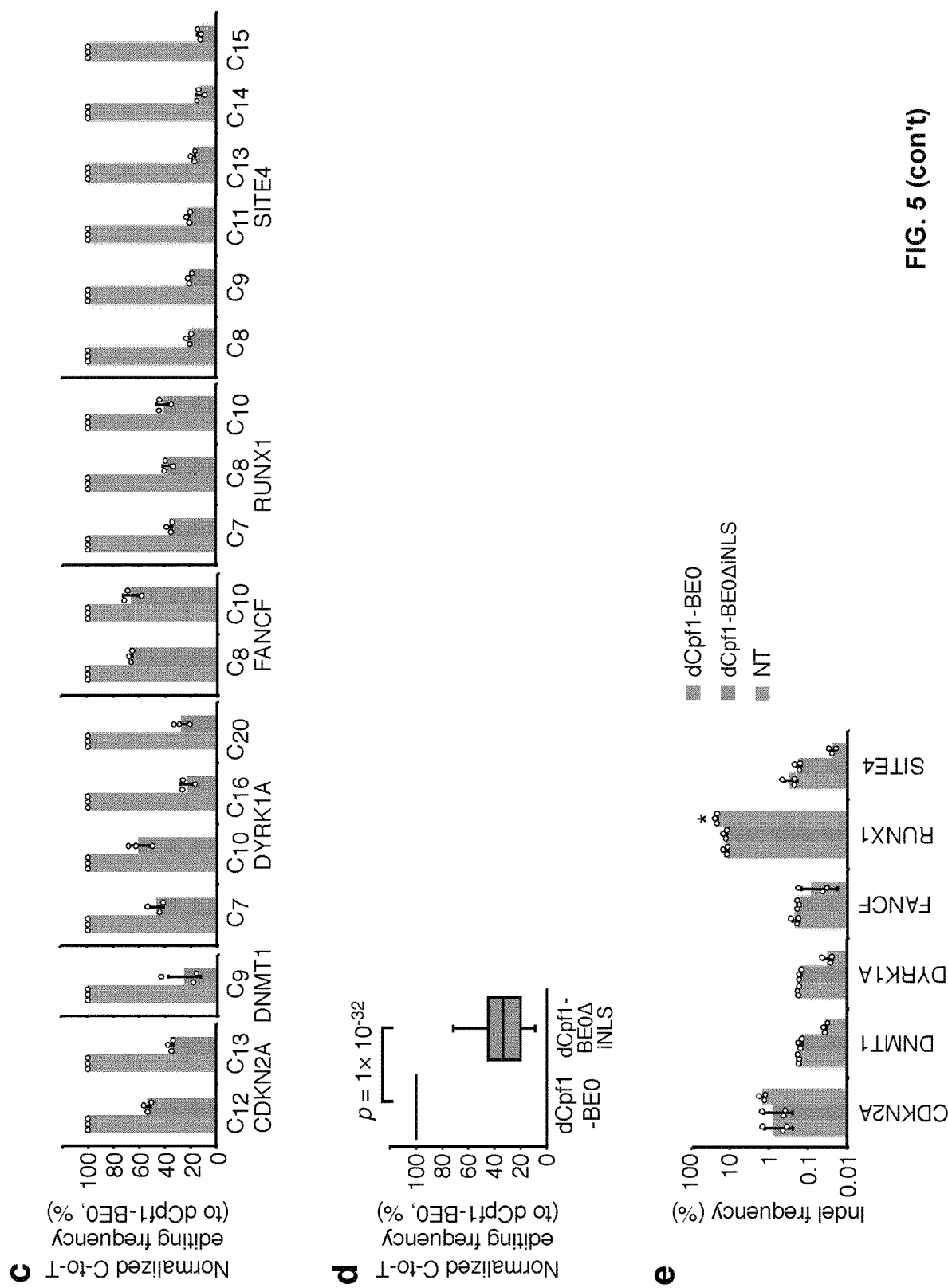
FIG. 5 (con't)

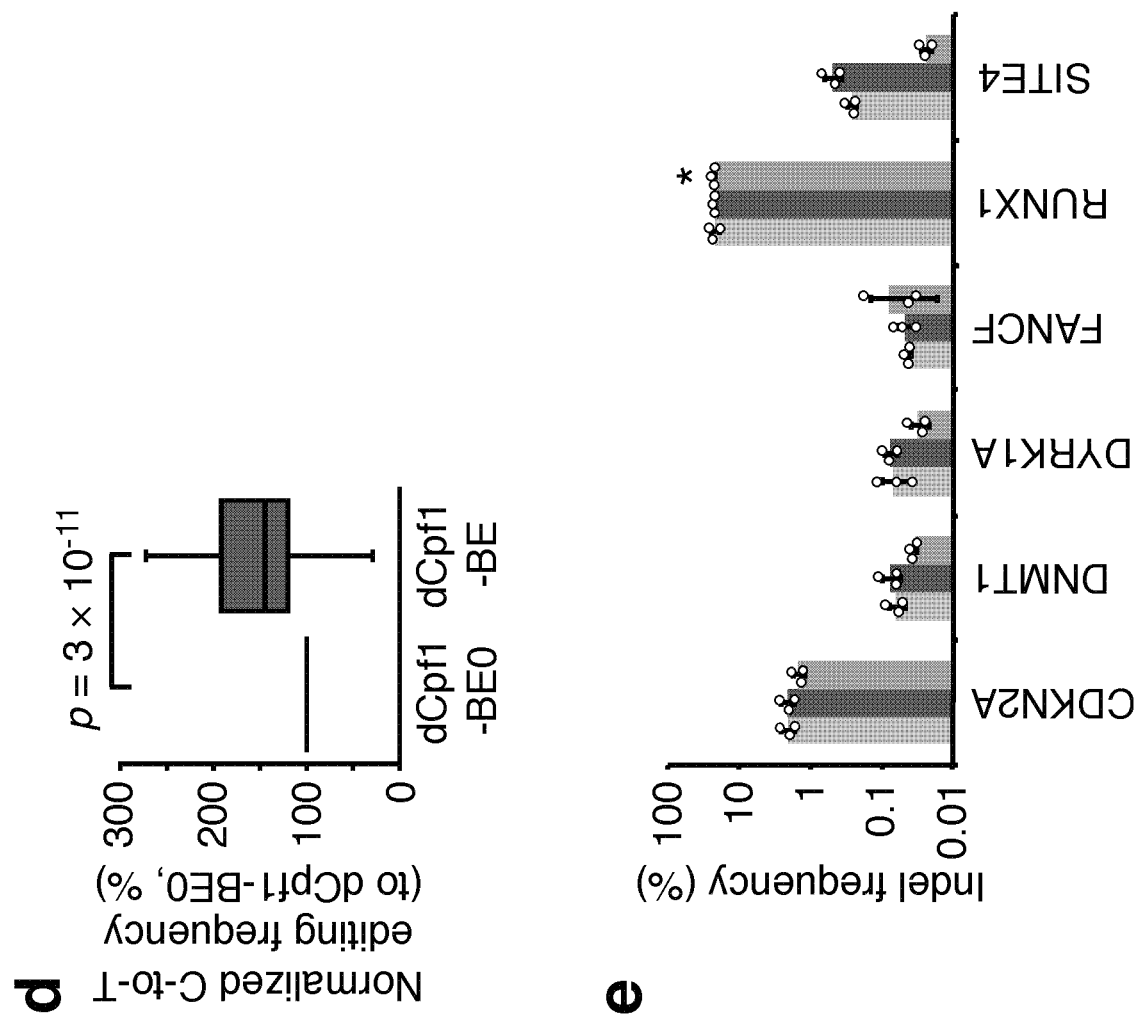
FIG. 6 (con't)

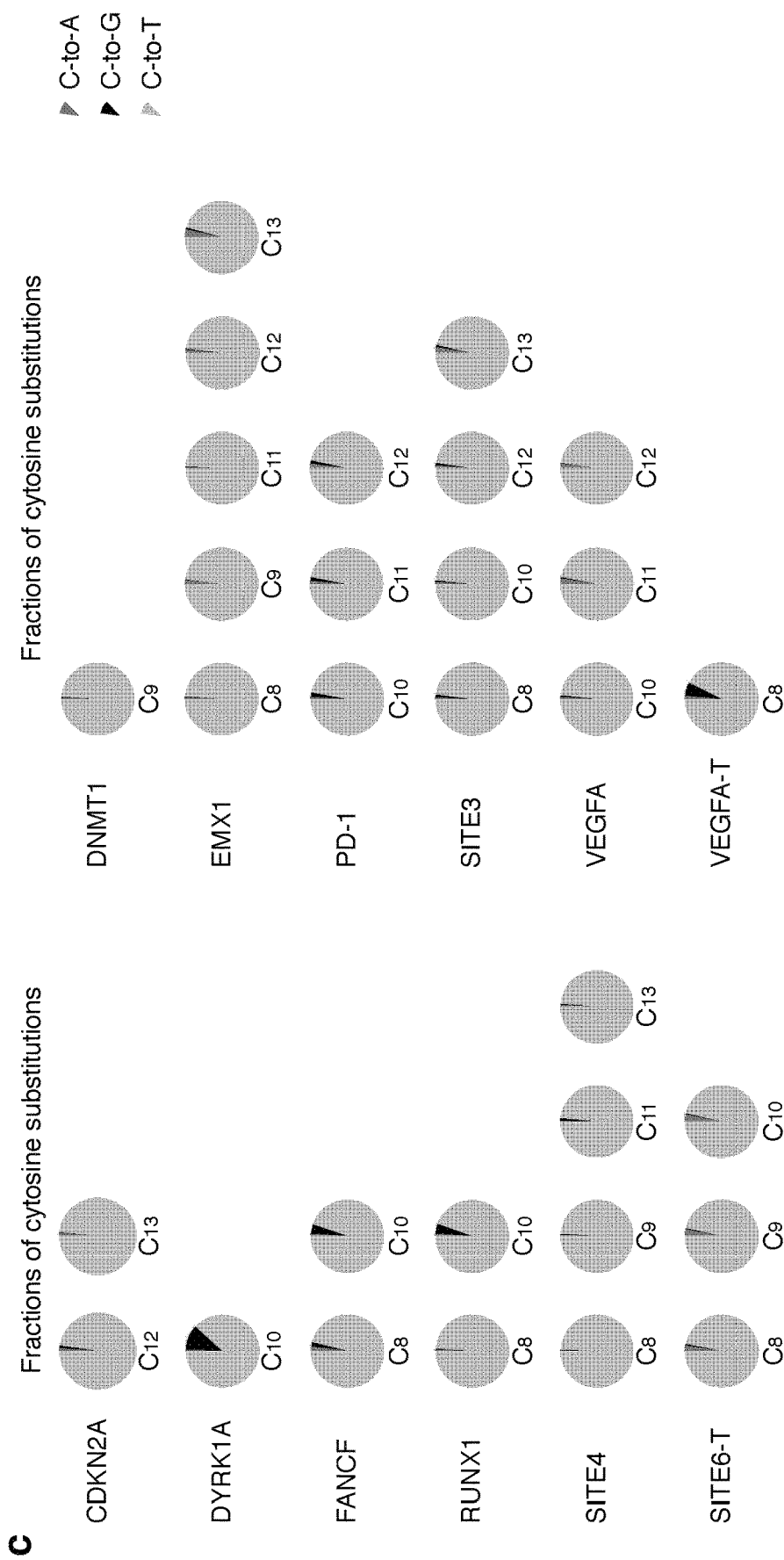
FIG. 7 (con't)

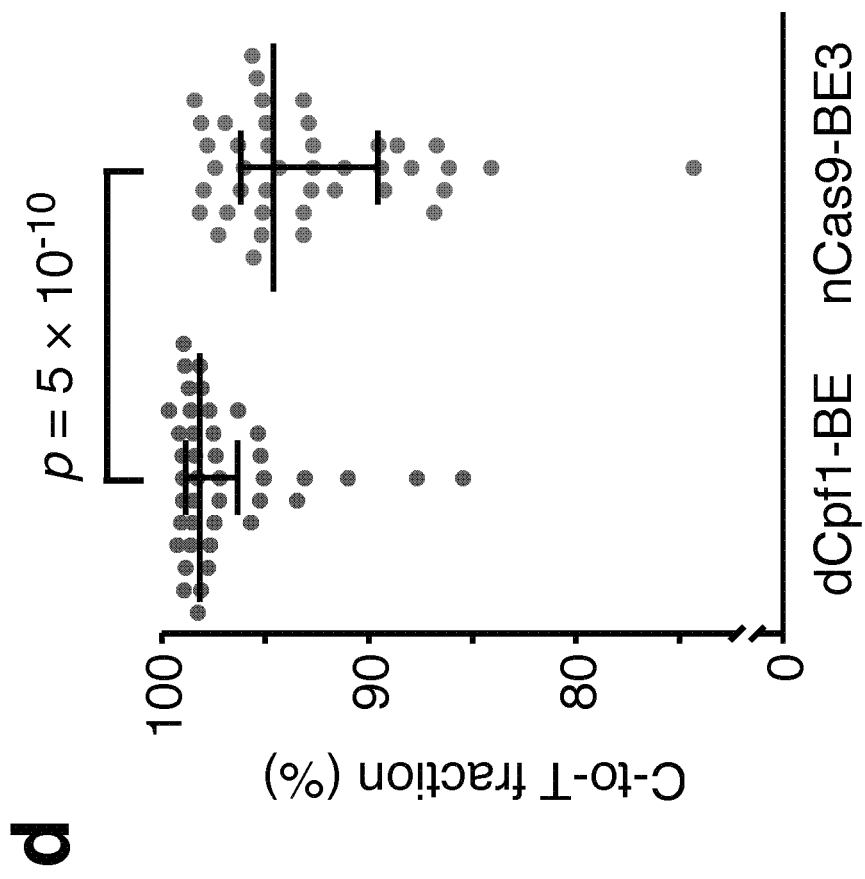
FIG. 7 (con't)

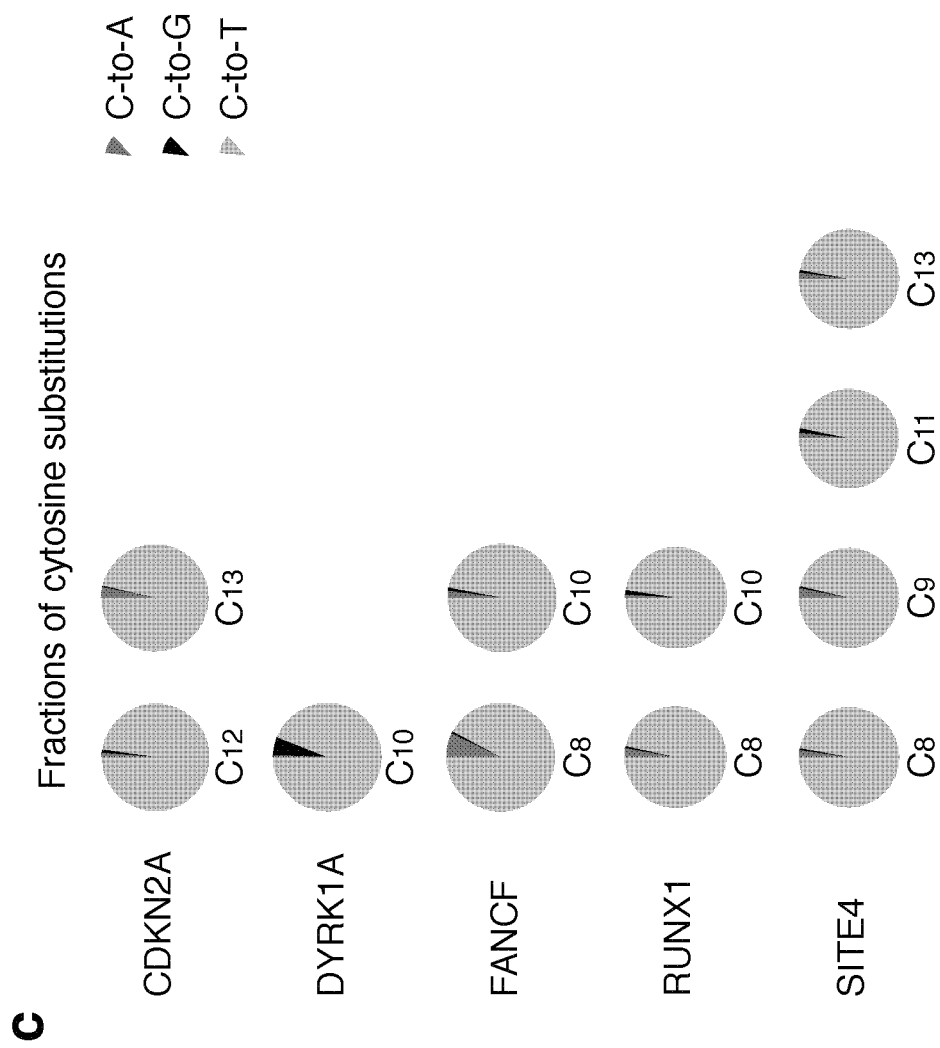
FIG. 8(con't)

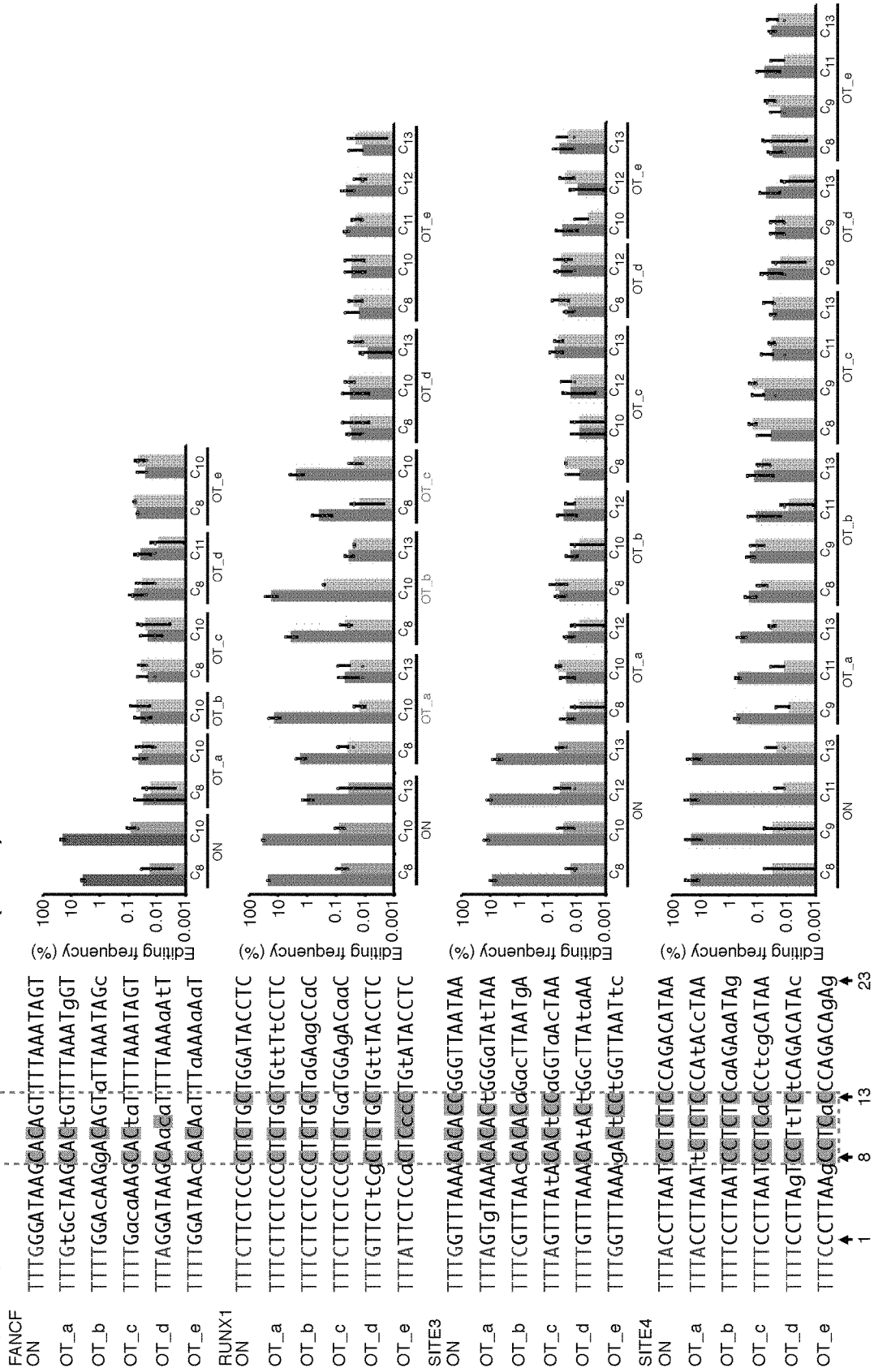
FIG. 9 (con't)

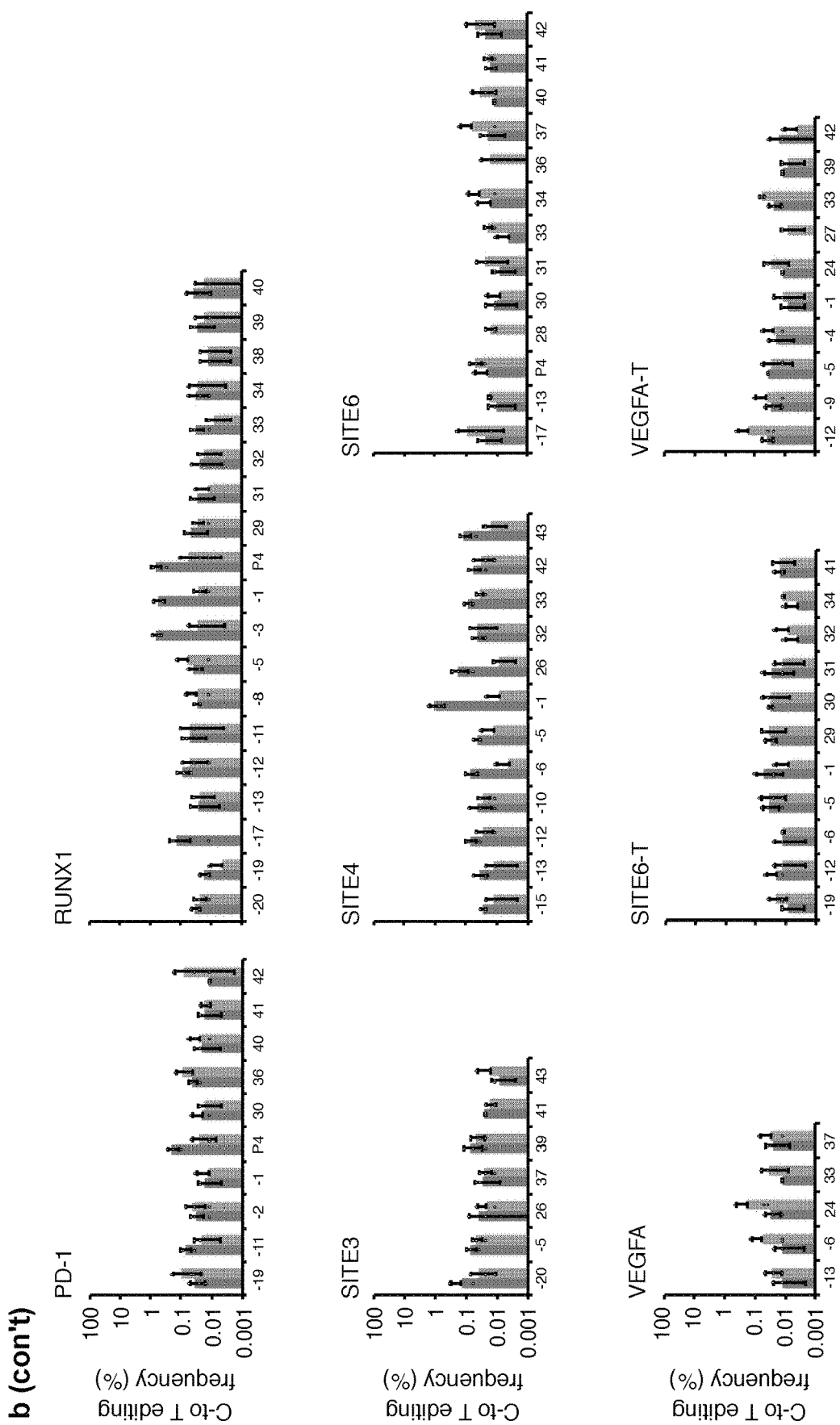
FIG. 10 (con't)

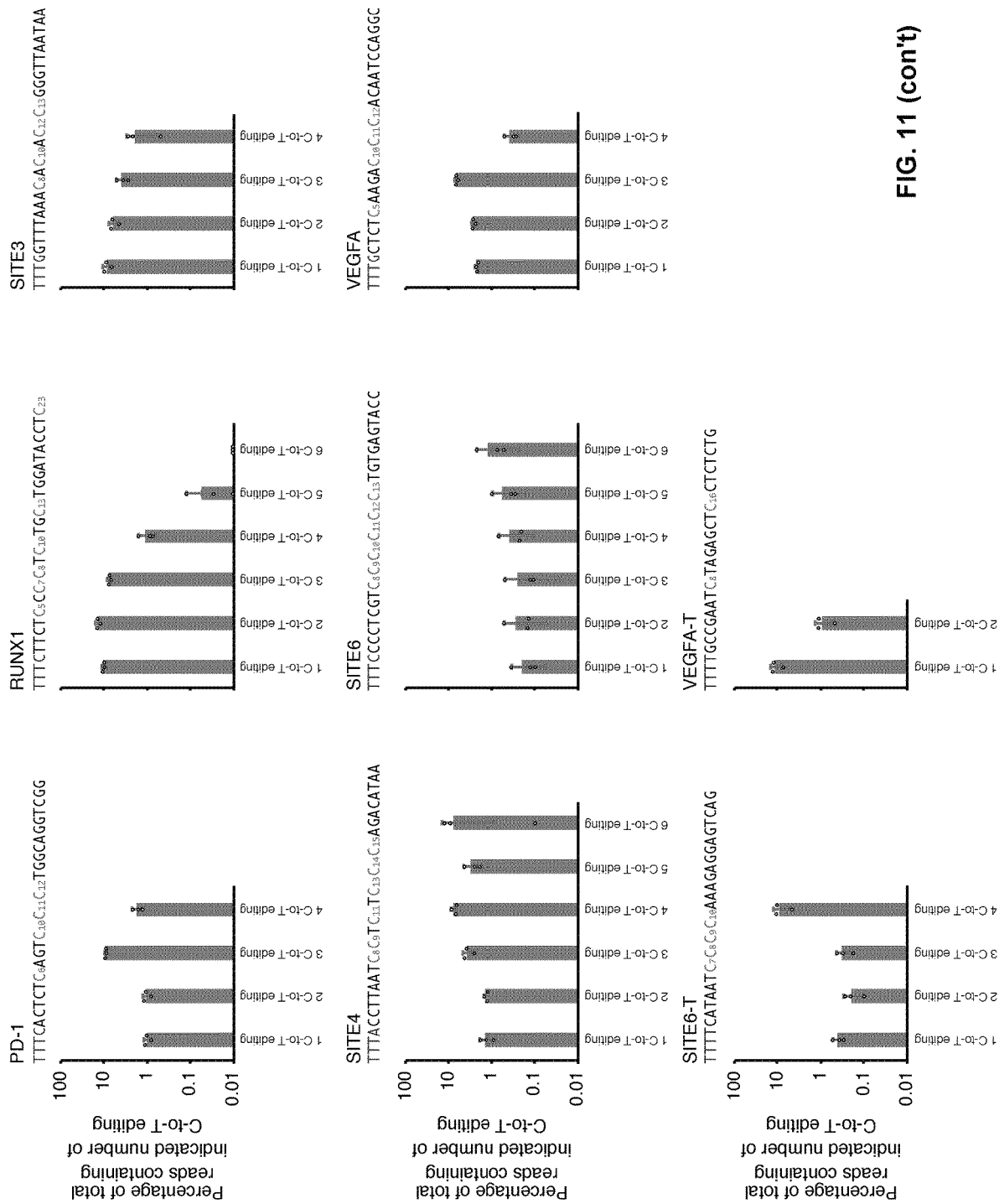
FIG. 11 (con't)

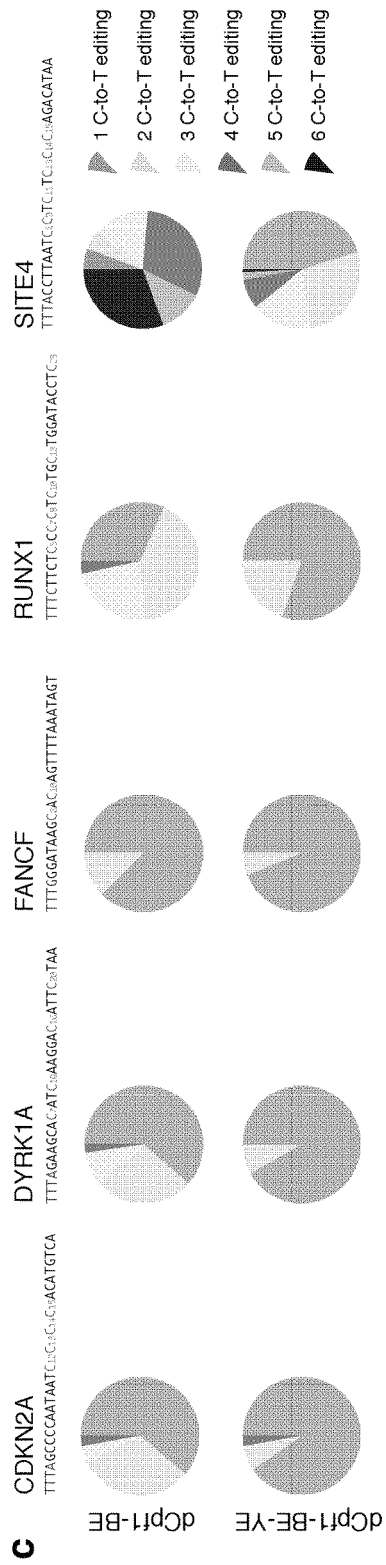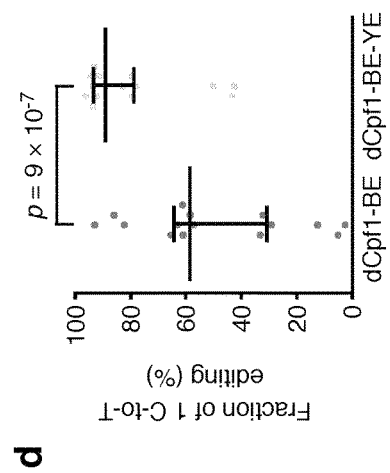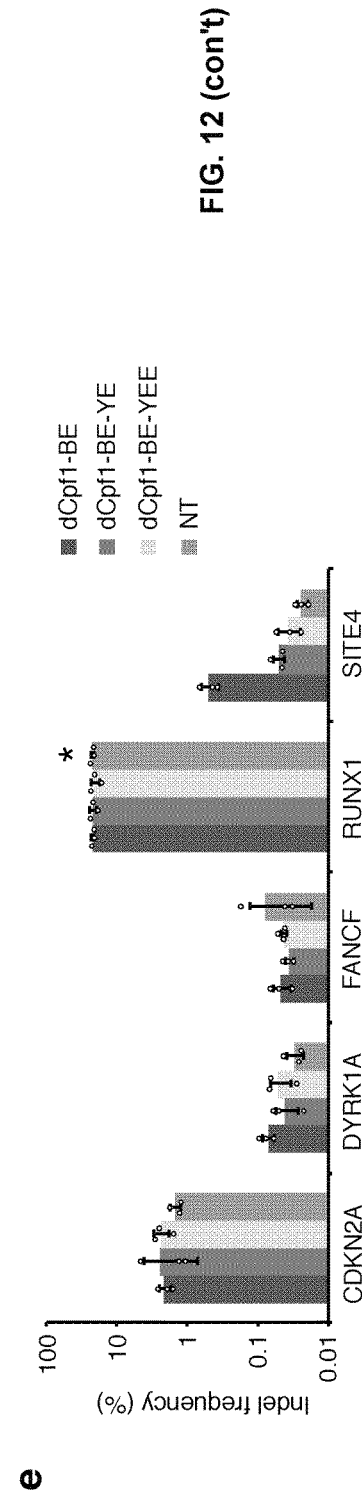
FIG. 12 (con't)

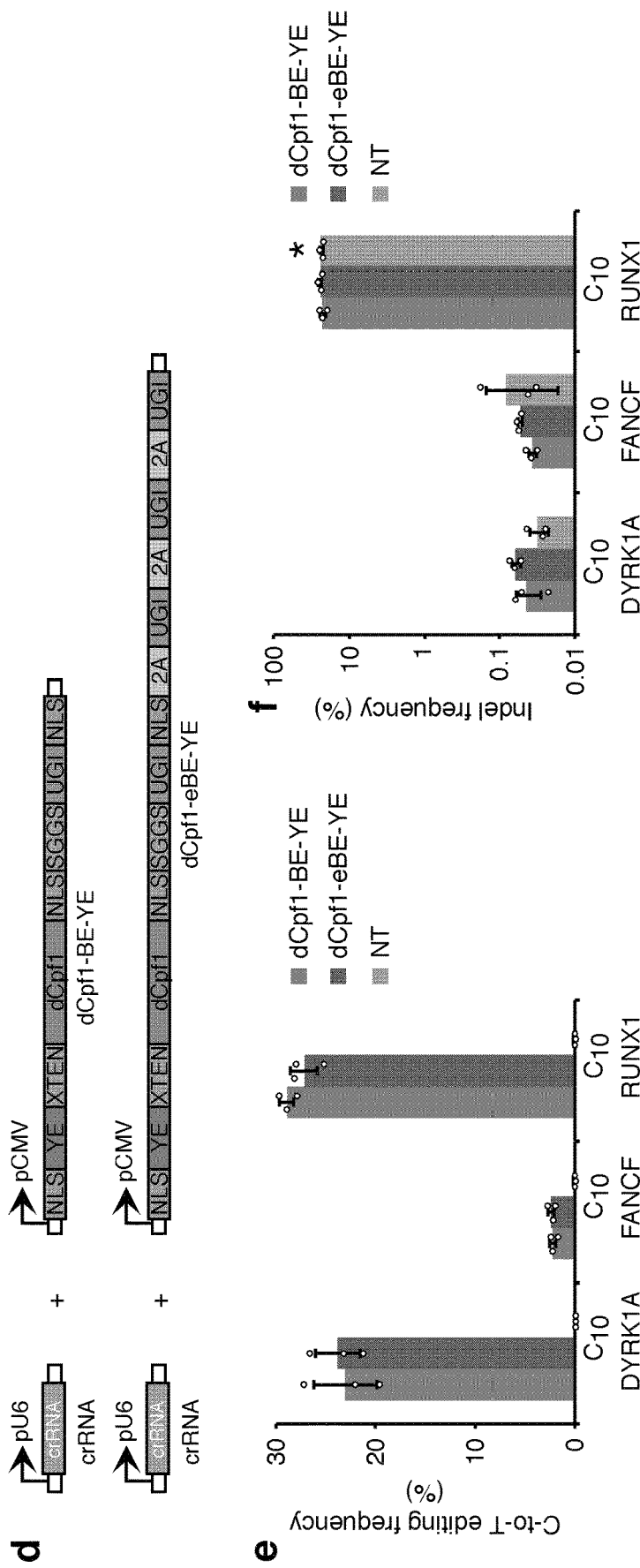
FIG. 13 (con't)

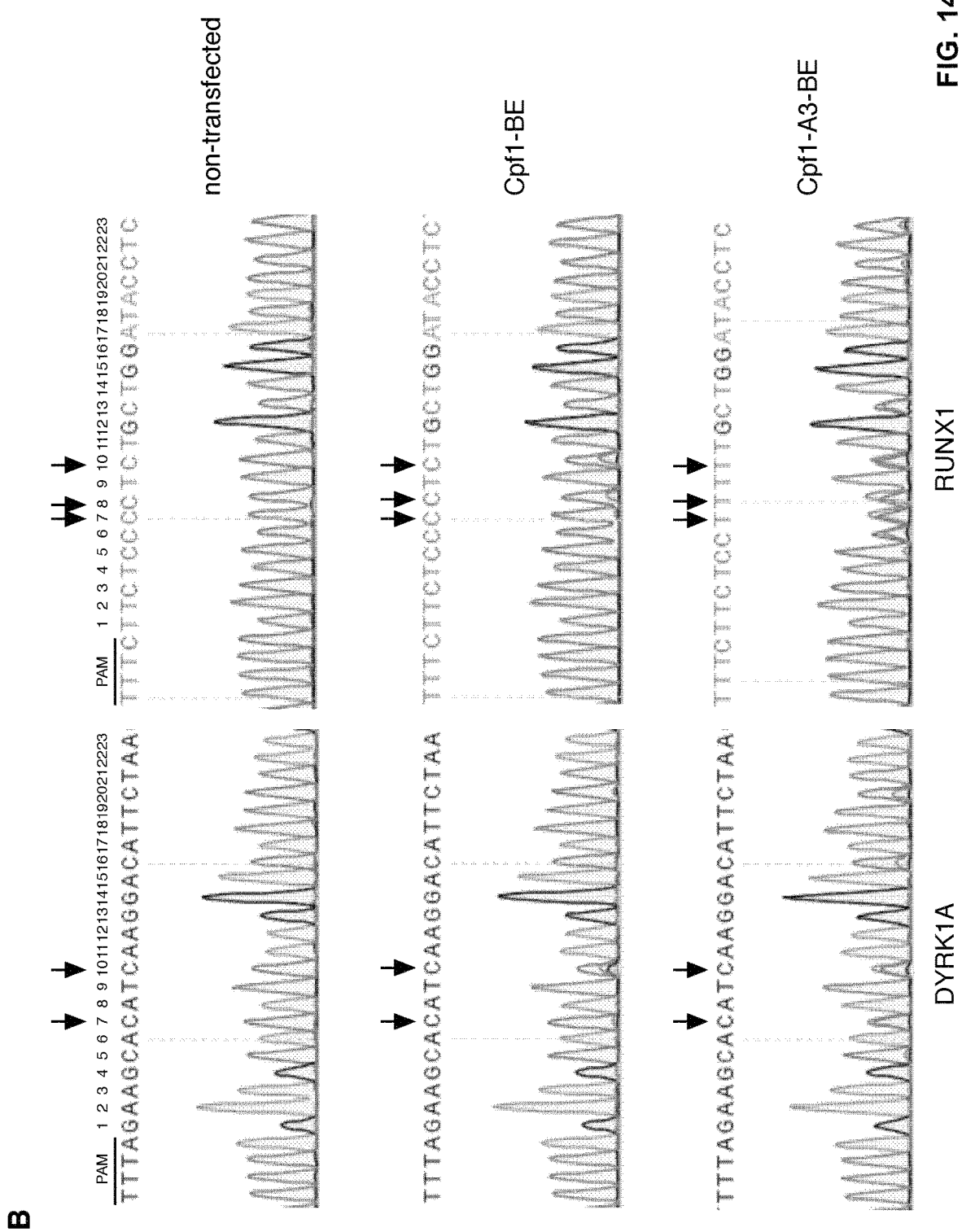
FIG. 14 (con't)

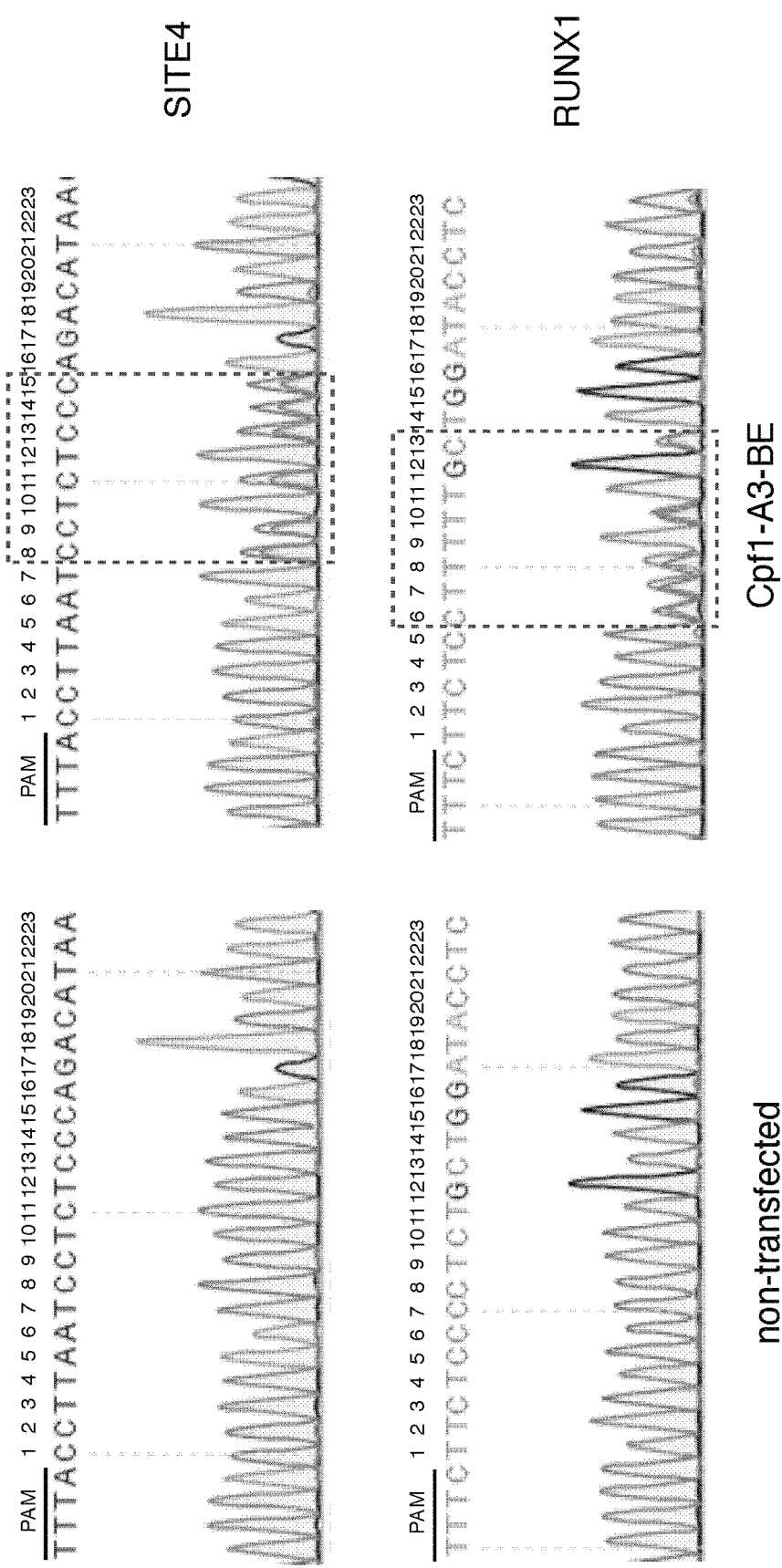
FIG. 15 (con't)

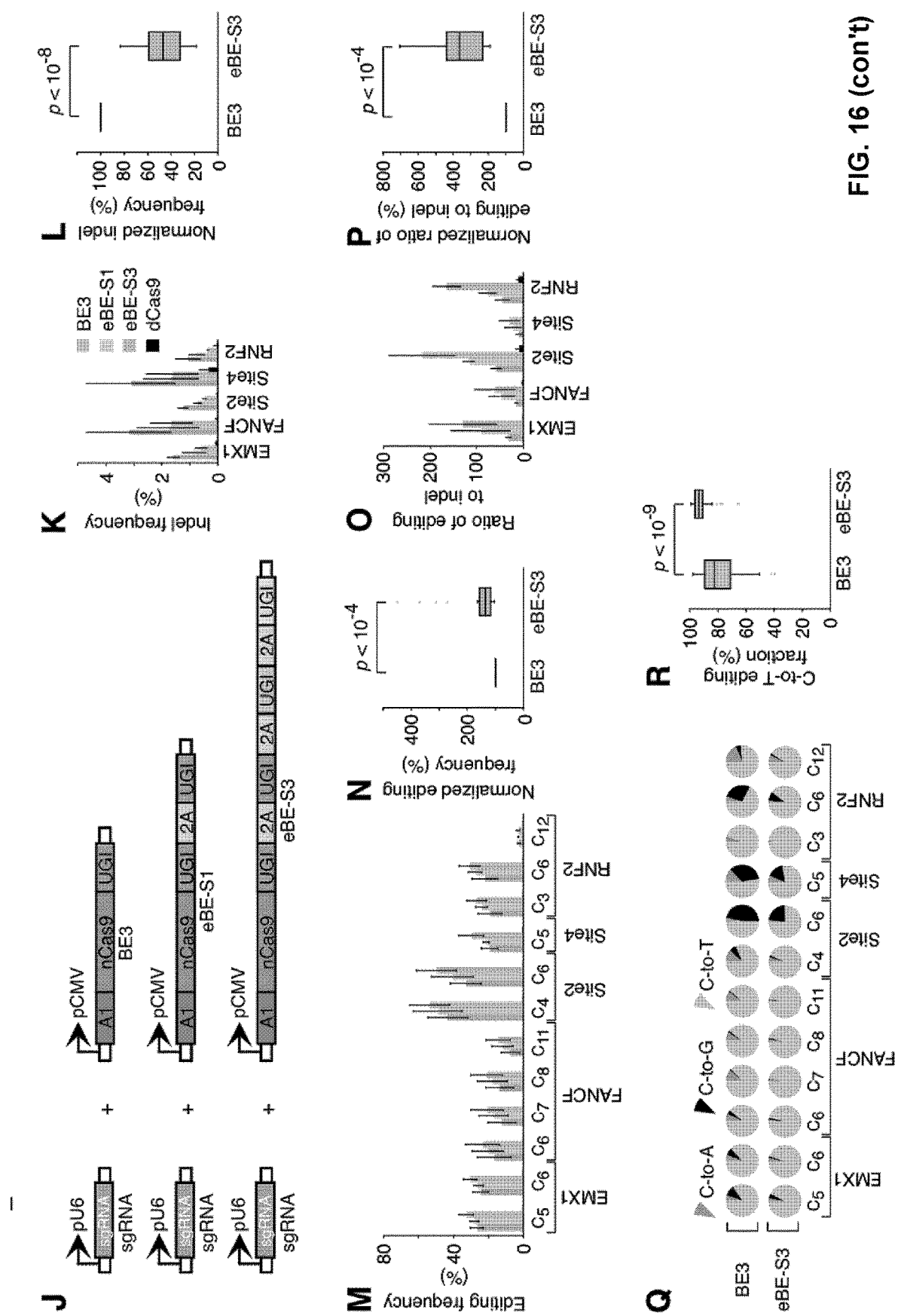
FIG. 16 (con't)

FUSION PROTEINS FOR IMPROVED PRECISION IN BASE EDITING

CROSS-REFERENCE TO RELATED PATENT APPLICATIONS

This application is a U.S. National Stage Application under 35 U.S.C. 371 of International Application No. PCT/CN2018/102750, filed Aug. 28, 2018, which claims priority to PCT/CN2017/100131, filed on Sep. 1, 2017, the contents of all of which are incorporated herein by reference in their entirety in the present disclosure.

SEQUENCE LISTING

The instant application contains a Sequence Listing which has been submitted in ASCII format via EFS-Web and is hereby incorporated by reference in its entirety. Said ASCII copy, created on Dec. 26, 2022, is named 274751_updated_ST25.txt and is 67,424 bytes in size.

BACKGROUND

Genome editing that can be used to genetically manipulate the genome of cells and living organism has broad application interest in life sciences research, biotechnology, agricultural technology development and pharmaceutical and clinical development. For example, genome editing can be used to correct driver mutations underlying genetic diseases and thereby resulting in complete cure of these diseases in a living organism. CRISPR/Cas (Clustered regularly interspaced short palindromic repeats/CRISPR-associated protein) system has been the most powerful genomic editing tool since its conception for its unparalleled editing efficiency, convenience and the potential applications in living organism. Directed by guide RNA (gRNA), a Cas nuclease can generate DNA double strand breaks (DSBs) at the targeted genomic sites in various cells (both cell lines and cells from living organisms). These DSBs are then repaired by the endogenous DNA repair system, which could be utilized to perform desired genome editing.

In general, two major DNA repair pathways could be activated by DSBs, non-homologous end joining (NHEJ) and homology-directed repair (HDR). NHEJ can introduce random insertions/deletions (indels) in the genomic DNA region around the DSBs, thereby leading to open reading frame (ORF) shift and ultimately gene inactivation. In contrast, when HDR is triggered, the genomic DNA sequence at target site could be replaced by the sequence of the exogenous donor DNA template through a homologous recombination mechanism, which can result in the correction of genetic mutation.

Base editors (BE), which integrate the CRISPR/Cas system with the APOBEC (apolipoprotein B mRNA editing enzyme, catalytic polypeptide-like) cytidine deaminase family, were recently invented that greatly enhanced the efficiency of CRISPR/Cas9-meditated gene correction. Through fusion with Cas9 nickase (nCas9), the cytosine (C) deamination activity of rat APOBEC1 (rA1) can be purposely directed to the target bases in genome and to catalyze C to Thymine (T) substitutions at these bases.

However, the reliance on the Cas9 nickase as the deaminase fusion partner in the most active current base editors leads to an increased frequency of unwanted indels and non-C-to-T base substitutions, and limits editing to regions with G/C rich protospacer adjacent motif (PAM) sequences.

SUMMARY

The present disclosure, in some embodiments, provide base editors useful for genome editing that combines a catalytically inactive Lachnospiraceae bacterium Cpf1 (dLbCpf1) with a cytidine deaminase. Such base editors recognize a T-rich PAM sequence and converts C to T in human cells at high efficiency and with low levels of indels, non-C-to-T substitutions and off-target editing. These are all significant improvements over Cas9-based base editors. In addition, besides APOBEC1 (A1), when the LbCpf1 was fused to APOBEC3 (A3, or APOBEC3A), even greater editing efficiency was achieved. In addition to the greatly improved editing efficiency and precision, LbCpf1-based base editors further differ from Cas9-based base editors in terms of editing windows. Another interesting discovery in the present disclosure is that the presence of a free uracil DNA glycosylase inhibitor (UGI) domain can further improve the efficiency and fidelity in base editing.

In accordance with one embodiment of the present disclosure, therefore, provided is a fusion protein comprising a first fragment comprising a cytidine deaminase and a second fragment comprising a catalytically inactive Lachnospiraceae bacterium Cpf1 (dLbCpf1).

In some embodiments, the cytidine deaminase is an apolipoprotein B mRNA editing enzyme, catalytic polypeptide-like (APOBEC) protein. In some embodiments, the APOBEC protein is selected from the group consisting of APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase. In one embodiment, the APOBEC protein is APOBEC1. In one embodiment, the APOBEC1 protein comprises a W90Y or R126E mutation, or the combination thereof. In some embodiments, the APOBEC protein is APOBEC3A. In some embodiments, the APOBEC3A protein has one or more mutations selected from W104A, Y130F, D131Y, D31E, and/or Y132D mutations; examples of combinatory mutations including Y130F-D131E-Y132D, Y130F-D131Y-Y132D.

In some embodiments, the fusion protein further includes one or more uracil DNA glycosylase inhibitor (UGI). In some embodiments, the fusion protein comprises at least two UGIs.

In some embodiments, at least one of the UGIs is separated from the first fragment and the second fragment by a protease cleavage site. In some embodiments, the protease cleavage site is a self-cleaving peptide.

In some embodiments, the fusion protein further comprises one or more nuclear localization sequences (NLS). In some embodiments, at least one iNLS is located between the second fragment and the first UGI. In some embodiments, at least two iNLS are located between the second fragment and the first UGI. In some embodiments, at least one NLS is located N-terminal to the first fragment and the second fragment.

In some embodiments, at least one NLS is located C-terminal to the first fragment and the second fragment. In some embodiments, the fusion protein comprises, from the N-terminus to the C-terminus, a first NLS, the first fragment, the second fragment, a second NLS, a first UGI, a third NLS, a self-cleaving peptide, and a second UGI. In some embodiments, the fusion protein further comprises a fourth NLS between the second fragment and the first UGI. In some embodiments, the fusion protein further comprises, N-terminal to the second UGI, a second self-cleaving peptide, and a third UGI.

Also provided, in one embodiment, is a method of editing a cytosine on a nucleic acid sequence in a sample, comprising contacting the sample with a suitable guide RNA and a fusion protein of the present disclosure, or a polynucleotide encoding the fusion protein.

In some embodiments, the cytosine is between nucleotide positions 6 and 22 3' to a protospacer adjacent motif (PAM) sequence on the nucleic acid sequence. In some embodiments, the cytidine deaminase is APOBEC3A. In some embodiments, the APOBEC3A protein has one or more mutations selected from W104A, Y130F, D131Y, D31E, and/or Y132D mutations; examples of combinatory mutations including Y130F-D131E-Y132D, Y130F-D131Y-Y132D.

In some embodiments, the cytosine is between nucleotide positions 8 and 13 3' to a protospacer adjacent motif (PAM) sequence on the nucleic acid sequence. In some embodiments, the cytidine deaminase is APOBEC1 protein. In some embodiments, the cytosine is between nucleotide positions 10 and 12 3' to the PAM sequence. In some embodiments, the cytidine deaminase is APOBEC1 protein comprising a W90Y or R126E mutation, or the combination thereof.

In some embodiments, the PAM sequence is a T-rich PAM sequence. In some embodiments, the method further comprises contacting the sample with a UGI not fused to a Cas protein, or a polynucleotide encoding the UGI.

In another embodiment, provided is a fusion protein comprising a first fragment comprising a cytidine deaminase, a second fragment comprising a Cas protein, and a uracil DNA glycosylase inhibitor (UGI) separated from the first fragment and the second fragment with a protease cleavage site. In some embodiments, the protease cleavage site is a self-cleaving peptide. In some embodiments, the fusion protein further comprises a second UGI separated from the first fragment and the second fragment with a second protease cleavage site. In some embodiments, the fusion protein further comprises a third UGI separated from the second UGI with a third protease cleavage site. In some embodiments, the Cas protein is Cas9 or Cpf1.

Polynucleotides encoding the fusion proteins of the present disclosure, constructs containing the polynucleotides, cells containing the polynucleotides or the constructs, and compositions comprising any of the above are also provided, without limitation.

DETAILED DESCRIPTION

Definitions

Figure 1:
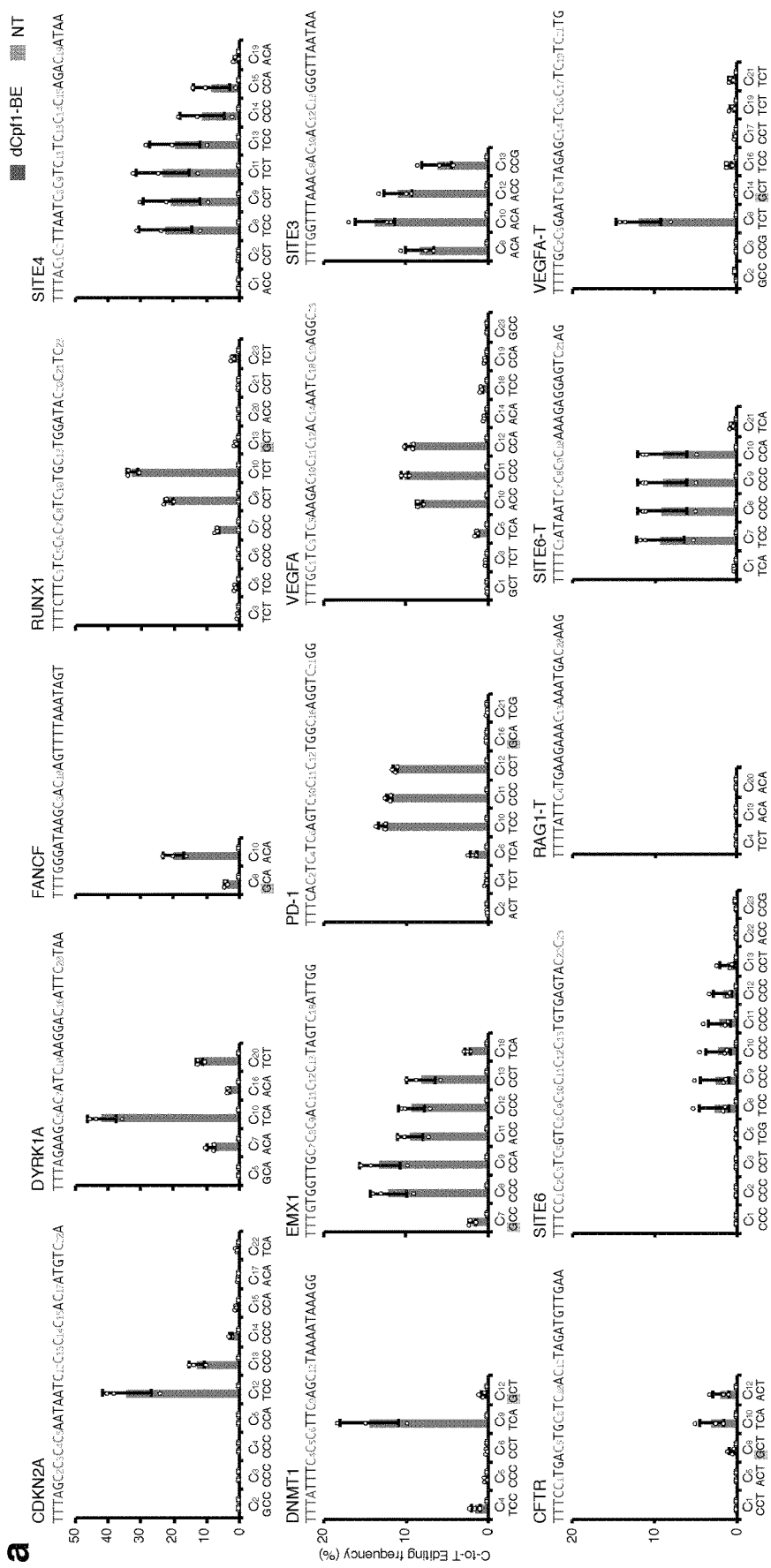
FIG. 1, with panels a-b. Base editing mediated by dCpf1-BE. (a) Determination of dCpf1-BE-induced base editing frequency at every single cytosine in the indicated spacer region. The dCpf1-BE showed inefficient C-to-T base editing at the cytosines following a G (shadowed). The cytosines were counted with the base proximal to the PAM setting as position 1. The target sequences, from left to right and top to bottom, are SEQ ID NO:18-32. (b) The comparison of base editing mediated by dCpf1-based and Cas9-bases BEs. The C-to-T editing frequencies of the indicated cytosines, the fractions of cytosine substitutions and the indel frequencies were individually determined at the indicated genomic target sites under different conditions. The target site sequences and editing windows of dCpf1-BE and Cas9-BEs are shown. NT, non-transfected. Asterisk denotes an unusually high basal indel frequency (or amplification, sequencing, alignment artifact) at the examined RUNX1 site in the non-transfected 293FT cells. Means±s.d. were from three independent experiments. The sequences shown, from top to bottom, are SEQ ID NO:33-48.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein", "amino acid chain" or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Fusion Proteins

As demonstrated in Example 1, a CRISPR-Cpf1-based base editor was developed by fusing the rat cytidine deaminase APOBEC1 to a catalytically inactive version of Lachnospiraceae bacterium Cpf1 (LbCpf1). The base editor recognizes a T-rich PAM sequence and converts C to T in human cells at high efficiency and with low levels of indels, non-C-to-T substitutions and off-target editing. These are all significant improvements over Cas9-based base editors. In addition, besides APOBEC1 (A1), when the LbCpf1 was fused to APOBEC3 (A3, or APOBEC3A), even greater editing efficiency was achieved.

In addition to the greatly improved editing efficiency and precision, LbCpf1-based base editors further differ from Cas9-based base editors in terms of editing windows. In general, the editing window of a Cas9-based base editor is from position 4 to position 8 and the observed editing windows for Cpf1-based base editors are from position 8 to position 13 (Cpf1-A1 base editor) and from position 6 to position 22 (Cpf1-A3 base editor). When the Cpf1 is fused to an APOBEC mutant (e.g., A1 with W90Y and R126E mutations), the editing window can be narrowed to position 10 to position 12, providing a tool for more precise position-specific editing.

Another interesting discovery in the present disclosure is that the presence of a free uracil DNA glycosylase inhibitor (UGI) domain can further improve the efficiency and fidelity in base editing. UGI has been used as a fusion portion in base editors, typically placed at the C-terminal end of the base editor. The added benefit of the addition of the free UGI, however, is surprising and unexpected. For convenience and good control, in one embodiment of the present disclosure, a UGI is fused to the based editor through a linker comprising a protease cleavage site, enabling generation of free UGI upon expression.

Yet another interesting finding of the present disclosure is that addition of more internal SV40 nuclear localization sequences (iNLS) in the base editor can further improve the editing efficiency. The iNLS, one, two, or more, can be inserted between the Cpf1 or Cas9 and the UGI. In some embodiments, the iNLS can be added to the N-terminal or C-terminal side of the cytidine deaminase and the Cpf1 or Cas9.

In accordance with one embodiment of the present disclosure, therefore, provided is a fusion protein comprising a first fragment comprising a cytidine deaminase and a second fragment comprising a catalytically inactive Lachnospiraceae bacterium Cpf1 (dLbCpf1).

"Cytidine deaminase" refers to enzymes that catalyze the irreversible hydrolytic deamination of cytidine and deoxycytidine to uridine and deoxyuridine, respectively. Cytidine deaminases maintain the cellular pyrimidine pool. A family of cytidine deaminases is APOBEC ("apolipoprotein B mRNA editing enzyme, catalytic polypeptide-like"). Members of this family are C-to-U editing enzymes. The N-terminal domain of APOBEC like proteins is the catalytic domain, while the C-terminal domain is a pseudocatalytic domain. More specifically, the catalytic domain is a zinc dependent cytidine deaminase domain and is important for cytidine deamination. RNA editing by APOBEC-1 requires homodimerisation and this complex interacts with RNA binding proteins to form the editosome.

Non-limiting examples of APOBEC proteins include APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase.

Various mutants of the APOBEC proteins are also known that have bring about different editing characteristics for base editors. For instance, for human APOBEC3A, certain mutants (e.g., Y130F, Y132D, W104A and D131Y) even outperform the wildtype human APOBEC3A in terms of editing efficiency. Accordingly, the term APOBEC and each of its family member also encompasses variants and mutants that have certain level (e.g., 70%, 75%, 80%, 85%, 90%, 95%, 98%, 99%) of sequence identity to the corresponding wildtype APOBEC protein and retain the cytidine deaminating activity. The variants and mutants can be derived with amino acid additions, deletions and/or substitutions. Such substitutions, in some embodiments, are conservative substitutions.

Lachnospiraceae bacterium Cpf1 (LbCpf1) is one of the many Cpf1 proteins of a large group. Cpf1 is a Cas protein. The term "Cas protein" or "clustered regularly interspaced short palindromic repeats (CRISPR)-associated (Cas) protein" refers to RNA-guided DNA endonuclease enzymes associated with the CRISPR (Clustered Regularly Interspaced Short Palindromic Repeats) adaptive immunity system in *Streptococcus pyogenes*, as well as other bacteria. Cas proteins include Cas9 proteins, Cas12a (Cpf1) proteins, Cas13 proteins and various engineered counterparts. Example Cas proteins are provided in the table below.

In some embodiments, the fusion protein comprises a first fragment comprising an APOBEC protein and a second fragment comprising a catalytically inactive LbCpf1. In some embodiments, the fusion protein comprises a first fragment comprising an APOBEC1 protein and a second fragment comprising a catalytically inactive LbCpf1. In some embodiments, the fusion protein comprises a first fragment comprising an APOBEC3A protein and a second fragment comprising a catalytically inactive LbCpf1. In some embodiments, the fusion protein comprises a first fragment comprising an APOBEC3A protein and a second fragment comprising a catalytically inactive LbCpf1.

In some embodiments, the cytidine deaminase is a human protein. In some embodiments, the cytidine deaminase is a rat protein. In some embodiments, the cytidine deaminase is a mouse protein. In some embodiments, the cytidine deaminase includes one, two, or three amino acid substitutions while retaining the cytidine deaminase activity (such as APOBEC1 with W90Y and/or R126E mutations).

The fusion protein may include other fragments, such as uracil DNA glycosylase inhibitor (UGI) and nuclear localization sequences (NLS).

The "Uracil Glycosylase Inhibitor" (UGI), which can be prepared from *Bacillus subtilis* bacteriophage PBS1, is a small protein (9.5 kDa) which inhibits *E. coli* uracil-DNA glycosylase (UDG) as well as UDG from other species. Inhibition of UDG occurs by reversible protein binding with a 1:1 UGD:UGI stoichiometry. UGI is capable of dissociating UDG-DNA complexes. A non-limiting example of UGI is found in *Bacillus phage* AR9 (YP_009283008.1). In some embodiments, the UGI comprises the amino acid sequence of SEQ ID NO:8 or has at least at least 70%, 75%, 80%, 85%, 90% or 95% sequence identity to SEQ ID NO:8 and retains the uracil glycosylase inhibition activity.

In some embodiments, the UGI is placed at the C-terminal side of the cytidine deaminase-Cpf1 portion. In some

TABLE A

Example Cas Proteins

| Cas protein types | Cas proteins |
|---|---|
| Cas9 proteins | Cas9 from *Staphylococcus aureus* (SaCas9) |
| | Cas9 from *Neisseria meningitidis* (NmeCas9) |
| | Cas9 from *Streptococcus thermophilus* (StCas9) |
| | Cas9 from *Campylobacter jejuni* (CjCas9) |
| Cas12a (Cpf1) proteins | Cas12a (Cpf1) from *Acidaminococcus* sp BV3L6 (AsCpf1) |
| | Cas12a (Cpf1) from *Francisella novicida* sp BV3L6 (FnCpf1) |
| | Cas12a (Cpf1) from *Smithella* sp SC_K08D17 (SsCpf1) |
| | Cas12a (Cpf1) from *Porphyromonas crevioricanis* (PcCpf1) |
| | Cas12a (Cpf1) from *Butyrivibrio proteoclasticus* (BpCpf1) |
| | Cas12a (Cpf1) from *Candidatus Methanoplasma termitum* (CmtCpf1) |
| | Cas 12a (Cpf1) from *Leptospira inadai* (LiCpf1) |
| | Cas 12a (Cpf1) from *Porphyromonas macacae* (PmCpf1) |
| | Cas12a (Cpf1) from *Peregrinibacteria bacterium* GW2011_WA2_33_10 (Pb3310Cpf1) |
| | Cas12a (Cpf1) from *Parcubacteria bacterium* GW2011_GWC2_44_17 (Pb4417Cpf1) |
| | Cas12a (Cpf1) from *Butyrivibrio* sp. NC3005 (BsCpf1) |
| | Cas12a (Cpf1) from *Eubacterium eligens* (EeCpf1) |
| Cas13 proteins | Cas13d from *Ruminococcus flavefaciens* XPD3002 (RfCas13d) |
| | Cas13a from *Leptotrichia wadei* (LwaCas13a) |
| | Cas13b from *Prevotella* sp. P5-125 (PspCas13b) |
| | Cas13b from *Porphyromonas gulae* (PguCas13b) |
| | Cas13b from *Riemerella anatipestifer* (RanCas13b) |
| Engineered Cas proteins | Nickases (mutation in one nuclease domain) |
| | Catalytically inactive mutant (dCas9; mutations in both of the nuclease domains) |
| | Enhanced variants with improved specificity (see, e.g., Chen et al., *Nature*, 550, 407-410 (2017) | embodiments, the fusion protein comprises at least two UGIs. In some embodiments, at least one of the UGIs is separated from the deaminase-Cpf1 portion by a protease cleavage site. Therefore, upon expression, the UGI may be cleaved off from the fusion protein to become a standalone protein, aside from the deaminase-Cpf1 portion. As demonstrated in Example 2, such free UGI (i.e., a UGI protein not fused to a deaminase-Cpf1 fusion protein) can further increase the efficiency and specificity of the base editor. In some embodiments, the fusion protein includes at least two such cleavage site-separated UGI units.

In some embodiments, the protease cleavage site is a self-cleaving peptide, such as the 2A peptides. "2A peptides" are 18-22 amino-acid-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (*Thosea asigna* virus 2A) were also identified. A few non-limiting examples of 2A peptides are provided in SEQ ID NO:9-11.

The fusion protein, in some embodiments, may include one or more nuclear localization sequences (NLS).

A "nuclear localization signal or sequence" (NLS) is an amino acid sequence that tags a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. A non-limiting example of NLS is the internal SV40 nuclear localization sequence (iNLS). In some embodiments, the NLS comprises the amino acid sequence of SEQ ID NO:7 or has at least 70%, 75%, 80%, 85%, 90% or 95% sequence identity to SEQ ID NO:7 and retains the nuclear localization activity.

In some embodiments, at least one NLS is located C-terminal to the first fragment and the second fragment (the cytidine deaminase-Cpf1 portion), e.g., between the second fragment (which includes the Cpf1) and an UGI. In some embodiments, at least two NLS are located between the second fragment and the UGI. In some embodiments, at least three NLS are located between the second fragment and the UGI. In some embodiments, at least one NLS is located N-terminal to the first fragment and the second fragment (the cytidine deaminase-Cpf1 portion).

Non-limiting example arrangements of the components in the fusion proteins include, from the N-terminus to the C-terminus, (a) NLS, cytidine deaminase, Cpf1, NLS, UGI, NLS, 2A, and UGI; (b) NLS, cytidine deaminase, Cpf1, NLS, NLS, UGI, NLS, 2A, and UGI; (c) NLS, cytidine deaminase, Cpf1, NLS, UGI, NLS, 2A, UGI, 2A, and UGI; (d) NLS, cytidine deaminase, Cpf1, NLS, UGI, NLS, 2A, UGI, 2A, UGI, 2A and UGI.

In some embodiments, a peptide linker is optionally provided between each of the fragments in the fusion protein. In some embodiments, the peptide linker has from 1 to 100 amino acid residues (or 3-20, 4-15, without limitation). In some embodiments, at least 10%, 20%, 30%, 40%, 50%, 60%, 70%, 80% or 90% of the amino acid residues of peptide linker are amino acid residues selected from the group consisting of alanine, glycine, cysteine, and serine.

TABLE 1

Example Sequences

| Name | Sequence | SEQ ID NO: |
|---|---|---|
| APOBEC1 | MSSETGPVAVDPTLRRRIEPHEFEVFFDPRELRKETCLLYEINWGGR HSIWRHTSQNTNKHVEVNFIEKFTTERYFCPNTRCSITWFLSWSPCG ECSRAITEFLSRYPHVTLFIYIARLYHHADPRNRQGLRDLISSGVTI QIMTEQESGYCWRNFVNYSPSNEAHWPRYPHLWVRLYVLELYCIILG LPPCLNILRRKQPQLTFFTIALQSCHYQRLPPHILWATGLK | 1 |
| APOBEC1-YE | MSSETGPVAVDPTLRRRIEPHEFEVFFDPRELRKETCLLYEINWGGR HSIWRHTSQNTNKHVEVNFIEKFTTERYFCPNTRCSITWFLSYSPCG ECSRAITEFLSRYPHVTLFIYIARLYHHADPENRQGLRDLISSGVTI QIMTEQESGYCWRNFVNYSPSNEAHWPRYPHLWVRLYVLELYCIILG LPPCLNILRRKQPQLTFFTIALQSCHYQRLPPHILWATGLK | 2 |
| APOBEC1-YEE | MSSETGPVAVDPTLRRRIEPHEFEVFFDPRELRKETCLLYEINWGGR HSIWRHTSQNTNKHVEVNFIEKFTTERYFCPNTRCSITWFLSYSPCG ECSRAITEFLSRYPHVTLFIYIARLYHHADPENRQGLEDLISSGVTI QIMTEQESGYCWRNFVNYSPSNEAHWPRYPHLWVRLYVLELYCIILG LPPCLNILRRKQPQLTFFTIALQSCHYQRLPPHILWATGLK | 3 |
| APOBEC3A | MEASPASGPRHLMDPHIFTSNFNNGIGRHKTYLCYEVERLDNGTSVKM DQHRGFLHNQAKNLLCGFYGRHAELRFLDLVPSLQLDPAQIYRVTWFI SWSPCFSWGCAGEVRAFLQENTHVRLRIFAARIYDYDPLYKEALQMLR DAGAQVSIMTYDEFKHCWDTFVDHQGCPFQPWDGLDEHSQALSGRLRA ILQNQGN | 4 |
| dLbCpf1 | MSKLEKFTNCYSLSKTLRFKAIPVGKTQENIDNKRLLVEDEKRAEDYK GVKKLLDRYYLSFINDVLHSIKLKNLNNYISLFRKKTRTEKENKELEN LEINLRKEIAKAFKGNEGYKSLFKKDIIETILPEFLDDKDEIALVNSF NGFTTAFTGFFDNRENMFSEEAKSTSIAFRCINENLTRYISNMDIFEK VDAIFDKHEVQEIKEKILNSDYDVEDFFEGEFFNFVLTQEGIDVYNAI IGGFVTESGEKIKGLNEYINLYNQKTKQKLPKFKPLYKQVLSDRESLS FYGEGYTSDEEVLEVFRNTLNKNSEIFSSIKKLEKLFKNFDEYSSAGI FVKNGPAISTISKDIFGEWNVIRDKWNAEYDDIHLKKKAVVTEKYEDD RRKSFKKIGSFSLEQLQEYADADLSVVEKLKEIIIQKVDEIYKVYGSS | 5 |

TABLE 1-continued

Example Sequences

| Name | Sequence | SEQ ID NO: |
|---|---|---|
| | EKLFDADFVLEKSLKKNDAVVAIMKDLLDSVKSFENYIKAFFGEGKET NRDESFYGDFVLAYDILLKVDHIYDAIRNYVTQKPYSKDKFKLYFQNP QFMGGWDKDKETDYRATILRYGSKYYLAIMDKKYAKCLQKIDKDDVNG NYEKINYKLLPGPNKMLPKVFFSKKWMAYYNPSEDIQKIYKNGTFKKG DMFNLNDCHKLIDFFKDSISRYPKWSNAYDFNFSETEKYKDIAGFYRE VEEQGYKVSFESASKKEVDKLVEEGKLYMFQIYNKDFSDKSHGTPNLH TMYFKLLFDENNHGQIRLSGGAELFMRRASLKKEELVVHPANSPIANK NPDNPKKTTTLSYDVYKDKRFSEDQYELHIPIAINKCPKNIFKINTEV RVLLKHDDNPYVIGIARGERNLLYIVVVDGKGNIVEQYSLNEIINNFN GIRIKTDYHSLLDKKEKERFEARQNWTSIENIKELKAGYISQVVHKIC ELVEKYDAVIALADLNSGFKNSRVKVEKQVYQKFEKMLIDKLNYMVDK KSNPCATGGALKGYQITNKFESFKSMSTQNGFIFYIPAWLTSKIDPST GFVNLLKTKYTSIADSKKFISSFDRIMYVPEEDLFEFALDYKNFSRTD ADYIKKWKLYSYGNRIRIFRNPKKNNVFDWEEVCLTSAYKELFNKYGI NYQQGDIRALLCEQSDKAFYSSFMALMSLMLQMRNSITGRTDVAFLIS PVKNSDGIFYDSRNYEAQENAILPKNADANGAYNIARKVLWAIGQFKK AEDEKLDKVKIAISNKEWLEYAQTSVKHGSPKKKRKV | |
| dAsCpf1 | MTQFEGFTNLYQVSKTLRFELIPQGKTLKHIQEQGFIEEDKARNDHYKE LKPIIDRIYKTYADQCLQLVQLDWENLSAAIDSYRKEKTEETRNALIEE QATYRNAIHDYFIGRTDNLTDAINKRHAEIYKGLFKAELFNGKVLKQLG TVTTTEHENALLRSFDKFTTYFSGFYENRKNVFSAEDISTAIPHRIVQD NFPKFKENCHIFTRLITAVPSLREHFENVKKAIGIFVSTSIEEVFSFPF YNQLLTQTQIDLYNQLLGGISREAGTEKIKGLNEVLNLAIQKNDETAHI IASLPHRFIPLFKQILSDRNTLSFILEEFKSDEEVIQSFCKYKTLLRNE NVLETAEALFNELNSIDLTHIFISHKKLETISSALCDHWDTLRNALYER RISELTGKITKSAKEKVQRSLKHEDINLQEIISAAGKELSEAFKQKTSE ILSHAHAALDQPLPTTLKKQEEKEILKSQLDSLLGLYHLLDWFAVDESN EVDPEFSARLTGIKLEMEPSLSFYNKARNYATKKPYSVEKFKLNFQMPT LASGWDVNKEKNNGAILFVKNGLYYLGIMPKQGRYKALSFEPTEKTSE GFDKMYYDYFPDAAKMIPKCSTQLKAVTAHFQTHTTPILLSNNFIEPLE ITKEIYDLNNPEKEPKKFQTAYAKKTGDQKGYREALCKWIDFTRDFLSK YTKTTSIDLSSLRPSSQYKDLGEYYAELNPLLYHISFQRIAEKEIMDAV ETGKLYLFQIYNKDFAKGHHGKPNLHTLYWTGLFSPENLAKTSIKLNGQ AELFYRPKSRMKRMAHRLGEKMLNKKLKDQKTPIPDTLYQELYDYVNHR LSHDLSDEARALLPNVITKEVSHEIIKDRRFTSDKFFFHVPITLNYQAA NSPSKFNQRVNAYLKEHPETPIIGIARGERNLIYITVIDSTGKILEQRS LNTIQQFDYQKKLDNREKERVAARQAWSVVGTIKDLKQGYLSQVIHEIV DLMIHYQAVVVLANLNFGFKSKRTGIAEKAVYQQFEKMLIDKLNCLVLK DYPAEKVGGVLNPYQLTDQFTSFAKMGTQSGFLFYVPAPYTSKIDPLTG FVDPFVWKTIKNHESRKHFLEGFDFLHYDVKTGDFILHFKMNRNLSFQR GLPGFMPAWDIVFEKNETQFDAKGTPFIAGKRIVPVIENHRFTGRYRDL YPANELIALLEEKGIVFRDGSNILPKLLENDDSHAIDTMVALIRSVLQM RNSNAATGEAYINSPVRDLNGVCFDSRFQNPEWPMDADANGAYHIALKG QLLLNHLKESKDLKLQNGISNQDWLAYIQELRNGSPKKKRKV | 6 |
| iNLS | PKKKRKV | 7 |
| UGI | TNLSDIIEKETGKQLVIQESILMLPEEVEEVIGNKPESDILVHTAYDES TDENVMLLTSDAPEYKPWALVIQDSNGENKIKML | 8 |
| P2A | GSGATNFSLLKQAGDVEENPGP | 9 |
| T2A | GSGEGRGSLLTCGDVEENPGP | 10 |
| E2A | GSGQCTNYALLKLAGDVESNPGP | 11 |
| APOBEC3A Y130F | MEASPASGPRHLMDPHIFTSNFNNGIGRHKTYLCYEVERLENGTSVKMDQ HRGFLHNQAKNLLCGFYGRHAELRFLDLVPSLQLDPAQIYRVTWFISWSP CFSWGCAGEVRAFLQENTHVRLRIFAARIFDYDPLYKEALQMLRDAGAQV SIMTYDEFKHCWDTFVDHQGCPFQPWDGLDEHSQALSGRLRAILQNQGN | 12 |
| APOBEC3A Y132D | MEASPASGPRHLMDPHIFTSNFNNGIGRHKTYLCYEVERLDNGTSVKMDQ HRGFLHNQAKNLLCGFYGRHAELRFLDLVPSLQLDPAQIYRVTWFISWSP CFSWGCAGEVRAFLQENTHVRLRIFAARIYDDDPLYKEALQMLRDAGAQV SIMTYDEFKHCWDTFVDHQGCPFQPWDGLDEHSQALSGRLRAILQNQGN | 13 |
| APOBEC3A W104A | MEASPASGPRHLMDPHIFTSNFNNGIGRHKTYLCYEVERLENGTSVKMDQ HRGFLHNQAKNLLCGFYGRHAELRFLDLVPSLQLDPAQIYRVTWFISWSP CFSAGCAGEVRAFLQENTHVRLRIFAARIYDYDPLYKEALQMLRDAGAQV SIMTYDEFKHCWDTFVDHQGCPFQPWDGLDEHSQALSGRLRAILQNQGN | 14 |

TABLE 1-continued

Example Sequences

| Name | Sequence | SEQ ID NO: |
|---|---|---|
| APOBEC3A D131Y | MEASPASGPRHLMDPHIFTSNFNNGIGRHKTYLCYEVERLDNGTSVKMDQ<br>HRGFLHNQAKNLLCGFYGRHAELRFLDLVPSLQLDPAQIYRVTWFISWSP<br>CFSWGCAGEVRAFLQENTHVRLRIFAARIYYYDPLYKEALQMLRDAGAQV<br>SIMTYDEFKHCWDTFVDHQGCPFQPWDGLDEHSQALSGRLRAILQNQGN | 15 |
| APOBEC3A Y130F-D131E-Y132D | MEASPASGPRHLMDPHIFTSNFNNGIGRHKTYLCYEVERLENGTSVKMDQ<br>HRGFLHNQAKNLLCGFYGRHAELRFLDLVPSLQLDPAQIYRVTWFISWSP<br>CFSWGCAGEVRAFLQENTHVRLRIFAARIFEDDPLYKEALQMLRDAGAQV<br>SIMTYDEFKHCWDTFVDHQGCPFQPWDGLDEHSQALSGRLRAILQNQGN | 16 |
| APOBEC3A Y130F-D131Y-Y132D | MEASPASGPRHLMDPHIFTSNFNNGIGRHKTYLCYEVERLDNGTSVKMDQ<br>HRGFLHNQAKNLLCGFYGRHAELRFLDLVPSLQLDPAQIYRVTWFISWSP<br>CFSWGCAGEVRAFLQENTHVRLRIFAARIFYDDPLYKEALQMLRDAGAQV<br>SIMTYDEFKHCWDTFVDHQGCPFQPWDGLDEHSQALSGRLRAILQNQGN | 17 |

For any fusion protein of the present disclosure, biological equivalents thereof are also provided. In some embodiments, the biological equivalents have at least about 70%, 75%, 80%, 85%, 90%, 95%, 98%, or 99% sequence identity with the reference fusion protein. Preferably, the biological equivalents retained the desired activity of the reference fusion protein. In some embodiments, the biological equivalents are derived by including one, two, three, four, five or more amino acid additions, deletions, substitutions, of the combinations thereof. In some embodiments, the substitution is a conservative amino acid substitution.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE B

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 |  |
| F | −4 | −5 | −5 | −3 | −4 | −3 | −6 | −5 | −4 | −5 | −2 | −5 | −4 | −1 | 0 | 1 | 2 | 9 |  |  |
| L | −6 | −4 | −3 | −3 | −2 | −2 | −4 | −3 | −3 | −2 | −2 | −3 | −3 | 2 | 4 | 2 | 6 |  |  |  |
| I | −2 | −3 | −2 | −1 | −1 | 0 | −2 | −2 | −2 | −2 | −2 | −2 | −2 | 4 | 2 | 5 |  |  |  |  |
| M | −5 | −3 | −2 | −2 | −1 | −1 | −3 | −2 | 0 | −1 | −2 | 0 | 0 | 2 | 6 |  |  |  |  |  |
| V | −2 | −1 | −1 | −1 | 0 | 0 | −2 | −2 | −2 | −2 | −2 | −2 | −2 | 4 |  |  |  |  |  |  |
| R | −4 | −3 | 0 | 0 | −2 | −1 | −1 | −1 | 0 | 1 | 2 | 3 | 6 |  |  |  |  |  |  |  |
| K | −5 | −2 | −1 | 0 | −1 | 0 | 0 | 0 | 1 | 1 | 0 | 5 |  |  |  |  |  |  |  |  |
| H | −3 | −2 | 0 | −1 | −1 | −1 | 1 | 1 | 2 | 3 | 6 |  |  |  |  |  |  |  |  |  |
| Q | −5 | −1 | 0 | −1 | 0 | −1 | 2 | 2 | 1 | 4 |  |  |  |  |  |  |  |  |  |  |
| N | −4 | 0 | −1 | 1 | 0 | 0 | 2 | 1 | 2 |  |  |  |  |  |  |  |  |  |  |  |
| E | −5 | 0 | −1 | 0 | 0 | 0 | 3 | 4 |  |  |  |  |  |  |  |  |  |  |  |  |
| D | −5 | 1 | −1 | 0 | 0 | 0 | 4 |  |  |  |  |  |  |  |  |  |  |  |  |  |
| T | −2 | 0 | 0 | 1 | 1 | 3 |  |  |  |  |  |  |  |  |  |  |  |  |  |  |
| A | −2 | 1 | 1 | 1 | 2 |  |  |  |  |  |  |  |  |  |  |  |  |  |  |  |
| S | 0 | 1 | 1 | 1 |  |  |  |  |  |  |  |  |  |  |  |  |  |  |  |  |
| P | −3 | −1 | 6 |  |  |  |  |  |  |  |  |  |  |  |  |  |  |  |  |  |
| G | −3 | 5 |  |  |  |  |  |  |  |  |  |  |  |  |  |  |  |  |  |  |
| C | 12 |  |  |  |  |  |  |  |  |  |  |  |  |  |  |  |  |  |  |  |

TABLE C

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |

TABLE C-continued

Conservative Amino Acid Substitutions

| For Amino Acid | Substitution With |
| --- | --- |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Use of the Fusion Proteins

As provided, the cytidine deaminase-LbCpf1 fusion protein is a highly efficient and high-fidelity base editor. Such base editors, therefore, can be used for efficient genome editing in biological samples. In addition, given that the cytidine deaminase-LbCpf1 base editor has different editing windows and employs different PAM sequences from Cas9-based systems, these new base editors supplement the Cas9 systems.

The present disclosure provides compositions and methods. Such compositions comprise an effective amount of a fusion protein, and an acceptable carrier. In some embodiments, the composition further includes a guide RNA that has a desired complementarity to a target DNA. Such a composition can be used for base editing in a sample.

The fusion proteins and the compositions can be used for base editing. In one embodiment, a method for editing a target polynucleotide is provided, comprising contacting to the target polynucleotide a fusion protein of the present disclosure and a guide RNA having at least partial sequence complementarity to the target polynucleotide, wherein the editing comprises deamination of a cytosine (C) in the target polynucleotide.

In one embodiment, provided is a method of editing a cytosine on a nucleic acid sequence in a sample. In some embodiments, the method entails contacting the sample a fusion protein of the present disclosure, or a polynucleotide encoding the fusion protein. In some embodiments, further added is a suitable guide RNA. Design of the guide RNA is readily available to the skilled artisan.

In some embodiments, the cytosine is between nucleotide positions 8 and 13 3' to a protospacer adjacent motif (PAM) sequence on the nucleic acid sequence. The cytidine deaminase for this editing window may be APOBEC1. In some embodiments, the cytosine is between nucleotide positions 10 and 12 3' to the PAM sequence. For the narrower editing window, a mutant APOBEC1 protein may be needed (e.g., the APOBEC1 protein with the W90Y and R126E mutations).

In some embodiments, the cytosine is between nucleotide positions 6 and 22 3' to a protospacer adjacent motif (PAM) sequence on the nucleic acid sequence. The cytidine deaminase for this editing window may be APOBEC3. In some embodiments, the editing window is narrower. For the narrower editing window, a mutant APOBEC3A protein may be needed (e.g., the APOBEC3A protein with the, W104A, Y130F, D131Y, D31E, and/or Y132D mutations; examples of combinatory mutations include Y130F-D131E-Y132D, Y130F-D131Y-Y132D; see SEQ ID NO:12-17).

In some embodiments, the PAM sequence is a T-rich PAM sequence. In some embodiments, further added is a free UGI not fused to a Cas protein, or a polynucleotide encoding the free UGI.

The contacting between the fusion protein (and the guide RNA) and the target polynucleotide can be in vitro, in particular in a cell culture. When the contacting is ex vivo, or in vivo, the fusion proteins can exhibit clinical/therapeutic significance. The in vivo contacting may be administration to a live subject, such as a human, an animal, a yeast, a plant, a bacterium, a virus, without limitation.

Free UGI and Uses

It is a discovery of the present disclosure that the presence of a free uracil DNA glycosylase inhibitor (UGI) domain can further improve the efficiency and fidelity in base editing.

In one embodiment, provided in a method of editing a target polynucleotide is provided, comprising contacting to the target polynucleotide a base editor and a UGI that is not fused to a Cas protein. In some embodiments, further added is a suitable guide RNA. Design of the guide RNA is readily available to the skilled artisan.

Also provided, is a fusion protein comprising a first fragment comprising a cytidine deaminase, a second fragment comprising a Cas protein, and a uracil DNA glycosylase inhibitor (UGI) separated from the first fragment and the second fragment with a protease cleavage site. In some embodiments, the protease cleavage site is a self-cleaving peptide, such as an A2 peptide. In some embodiments, the fusion protein further includes a second UGI linked through a second protease cleavage site. In some embodiments, the fusion protein further includes a third UGI linked through a third protease cleavage site.

Various kinds of cytidine deaminases and Cas proteins are described above. In some embodiments, the cytidine deaminase is selected from the group consisting of APOBEC1, APOBEC2, APOBEC3A, APOBEC3B, APOBEC3C, APOBEC3D, APOBEC3F, APOBEC3G, APOBEC3H, APOBEC4, and activation-induced (cytidine). In some embodiments, the Cas protein is Cas9 or Cpf1.

In one embodiment, provided is a method of editing a nucleic acid sequence in a sample. In some embodiments, the method entails contacting the sample a fusion protein of the present disclosure, or a polynucleotide encoding the fusion protein. In some embodiments, further added is a suitable guide RNA.

The present disclosure also provides compositions and methods. Such compositions comprise an effective amount of a fusion protein, and an acceptable carrier. In some embodiments, the composition further includes a guide RNA that has a desired complementarity to a target DNA. Such a composition can be used for base editing in a sample.

The contacting between the fusion protein (and the guide RNA) and the target polynucleotide can be in vitro, in particular in a cell culture. When the contacting is ex vivo, or in vivo, the fusion proteins can exhibit clinical/therapeutic significance. The in vivo contacting may be administration to a live subject, such as a human, an animal, a yeast, a plant, a bacterium, a virus, without limitation.

EXAMPLES

Example 1: Fusion Protein Enables Precise Editing of Single Bases in A/T-Rich Regions of the Human Genome The targeting range of CRISPR-Cas9 base editors (BEs) is limited by their G/C-rich PAM sequences. To overcome this limitation, this example developed a CRISPR-Cpf1-based BE by fusing the rat cytidine deaminase APOBEC1 to a catalytically inactive version of Lachnospiraceae bacterium Cpf1. The base editor recognizes a T-rich PAM sequence and converts C to T in human cells with low levels of indels, non-C-to-T substitutions and off-target editing.

Methods and Materials

Plasmid Construction pST1374-Lb-Cpf1-NLS was commercially synthesized. Two primer sets (LB_D971A_F/LB_R4635) (LB_D971A_R/LB_F2096) were used to amplify the D832A-containing fragment LbCpf1-D832A. Then two primer sets (LB_E1006A_F/LB_E1006A_R) (LB_D1225A_F/LB_D1225A_R) were used to introduce the mutations E925A and D1148A. The D832A, E925A and D1148A-containing dLbCpf1 was cloned into the PstI and ApaI linearized pST1374-LbCpf1-NLS with plasmid recombination kit Clone Express® (Vazyme, C112-02) to generate the dLbCpf1 expression plasmid pST1374-dLbCpf1-NLS. Two primer sets (LB_BE3_F1/LB_BE3_R1) (LB_BE3_F2/CPF_BE3_fu_R2) were used to amplify the dLbCpf1-SV40 NLS-UGI fragment, which was cloned into the SmaI and PmeI linearized pCMV-BE3 to generate dLbCpf1-BE0 (dCpf1-BE0) expression vector pCMV-Apobec1-XTEN-dLbCpf1(D832A/E925A/D1148A)-SV40NLS-SGGS-UGI-SV40NLS.

pST1374-As-Cpf1-NLS was commercially synthesized. Two primer sets (AS_D917A_F/AS_R4871) (AS_D917A_R/AS_F2155) were used to amplify the D908A-containing fragment AsCpf1-D908A. Then two primer sets (AS_E1006A_F/AS_E1006A_R) (As_D1225A_F/As_D1225A_R) were used to introduce the mutations E993A and D1235A. The D908A, E993A and D1235A-containing dAsCpf1 was cloned into the PstI and ApaI linearized pST1374-AsCpf1-NLS to generate the dAsCpf1 expression plasmid pST1374-dAsCpf1-NLS. Two primer sets (As_BE3_F1/As_BE3_R1) (As_BE3_F2/CPF_BE3_fu_R2) were used to amplify the dAsCpf1-SV40 NLS-UGI fragment, which was cloned into the SmaI and PmeI linearized pCMV-BE3 to generate dAsCpf1-BE0 expression vector pCMV-Apobec1-XTEN-dAsCpf1 (D908A/E993A/D1235A)-SV40NLS-SGGS-UGI-SV40NLS.

Oligonucleotides (L079_LbCpf1scaffold_for/L080_LbCpf1scaffold_rev, L081_AsCpf1scaffold_for/L082_AsCpf1scaffold_rev) were annealed and ligated into BsaI and EcoRI linearized pGL3-U6-sgRNA-PGK-puromycin (addgene, 51133) to generate the Lb-crRNA and As-crRNA expression vectors pLb-Cpf1-pGL3-U6-sgRNA and pAs-Cpf1-pGL3-U6-sgRNA.

Oligonucleotides supF_Cpf1_sg1_FOR/supF_Cpf1_sg1_REV, supF_Cpf1_sg2_FOR/supF_Cpf1_sg2_REV, supF_Cpf1_sg3_FOR/supF_Cpf1_sg3_REV or other pairs of oligonucleotides with different lengths were annealed and ligated into BsaI linearized pLb-Cpf1-pGL3-U6-sgRNA or pAs-Cpf1-pGL3-U6-sgRNA to generate the expression vectors for the Lb-crRNAs or As-crRNAs targeting SupF gene in the shuttle vector pSP189.

Two primer sets (LB_BE3_F1/LB_R) (UGI_F/CPF_BE3_fu_R2) were used to amplify the dLbCpf1-SGGS-UGI fragment, which was cloned into the SmaI and PmeI linearized dLbCpf1-BE0 (dCpf1-BE0) expression vector to generate dLbCpf1-BE0ΔiNLS expression vector pCMV-Apobec1-XTEN-dLbCpf1(D832A/E925A/D1148A)-SGGS-UGI-SV40NLS.

The primer set (1xNLS_pcrF/1xNLS_pcrR) was used to amplify the fragment NLS-Apobec1 from pCMV-BE3 and the gel-purified NLS-Apobec1 fragment was ligated into the SmaI and NotI linearized dCpf1-BE0 expression vector to generate the dCpf1-BE expression vector pCMV-SV40NLS-Apobec1-XTEN-dLbCpf1(D832A/E925A/D1148A)-SV40NLS-SGGS-UGI-SV40NLS.

Two primer sets (APOBEC_W90Y_F1/1xNLS_pcrR) (1xNLS_pcrF/APOBEC_W90Y_R1) were used to amplify the W90Y-containing fragment APOBEC-Y with the primer set. Two primer sets (APOBEC_R126E_F/APOBEC_R126E_R) (APOBEC_R132E_F/APOBEC_R132E_R) were used to introduce the mutations R126E and R132E. The APOBEC-YE and APOBEC-YEE fragment were respectively ligated into the NotI and SmaI linearized dCpf1-BE expression vector to generate the dCpf1-BE-YE and dCpf1-BE-YEE expression vectors pCMV-SV40NLS-Apobec1(W90Y/R126E)-XTEN-dLbCpf1(D832A/E925A/D1148A)-SV40NLS-SGGS-UGI-SV40NLS and pCMV-SV40NLS-Apobec1(W90Y/R126E/R132E)-XTEN-dLbCpf1(D832A/E925A/D1148A)-SV40NLS-SGGS-UGI-SV40NLS.

The primer set (LB_F2096/BE8.1_PmeI_ApaI_R) was used to introduce the ApaL site into dCpf1-BE expression vector to generate pCMV-dCpf1-BE-ApaI. The primer set (ApaI_1T2AUGI_F/PmeI_3T2AUGI_R) was used to amplify the 3×2A-UGI fragment from commercially synthesized DNA fragment 3×2A-UGI and the 3×2A-UGI fragment was ligated into the PmeI and ApaL linearized pCMV-dCpf1-BE-ApaI to generate the dCpf1-eBE expression vector pCMV-SV40NLS-Apobec1-XTEN-dLbCpf1 (D832A/E925A/D1148A)-SV40NLS-SGGS-UGI-SV40NLS-T2A-UGI-SV40NLS-P2A-UGI-SV40NLS-T2A-UGI-SV40NLS. Apobec1-YE fragment was ligated into NotI and SmaI linearized dCpf1-eBE expression vector to generate the dCpf1-eBE-YE expression vector pCMV-SV40NLS-Apobec1(W90Y/R126E)-XTEN-dLbCpf1 (D832A/E925A/D1148A)-SV40NLS-SGGS-UGI-SV40NLS-T2A-UGI-SV40NLS-P2A-UGI-SV40NLS-T2A-UGI-SV40NLS.

Oligonucleotides hCDKN2A_cpf1_sg1_FOR/hCDKN2A_cpf1_sg1_REV were annealed and ligated into BsaI linearized pLb-Cpf1-pGL3-U6-sgRNA to generate crCDKN2A expression vector pcrCDKN2A. Oligonucleotides hCDKN2A_cpfsp_sg1_FOR/hCDKN2A_cpfsp_sg1_REV were annealed and ligated into BsaI linearized pGL3-U6-sgRNA-PGK-puromycin to generate sgCDKN2A expression vector psgCDKN2A. Other crRNA and sgRNA expression vectors were constructed by the same way.

Cell Culture and Transfection

293FT and U2OS from ATCC were maintained in DMEM (10566, Gibco/Thermo Fisher Scientific)+10% FBS (16000-044, Gibco/Thermo Fisher Scientific) and have been tested to exclude *Mycoplasma* contamination.

For base editing in episomal shuttle vectors, 293FT cells were seeded in a 6-well plate at a density of $5\times10^5$ per well and transfected with 500 μl serum-free Opti-MEM that contained 4 μl LIPOFECTAMINE LTX (Life, Invitrogen), 2 μl LIPOFECTAMINE plus (Life, Invitrogen), 1 μg dLbCpf1-BE0 expression vector (or dAsCpf1-BE0 expression vector), 0.5 μg crRNA-expressing plasmid and 0.5 μg shuttle vector pSP189. After 48 hr, the plasmids were extracted from the cells with TIANprep Mini Plasmid Kit (DP103-A, TIANGEN).

For base editing in genomic DNA, 293FT and U2OS cells were seeded in a 24-well plate at a density of $2\times10^5$ per well and transfected with 500 µl serum-free Opti-MEM that contained 5.04 µl LIPOFECTAMINE LTX (Life, Invitrogen), 1.68 µl LIPOFECTAMINE plus (Life, Invitrogen), 1 µg dCpf1-BE0 expression vector (dCpf1-BE0ΔiNLS, dCpf1-BE, dCpf1-BE-YE, dCpf1-BE-YEE, dCpf1-eBE, dCpf1-eBE-YE expression vector, or pCMV-BE2, pCMV-BE3), and 0.68 µg crRNA or sgRNA-expressing plasmid. After 72 hr, the genomic DNA was extracted from the cells with QuickExtract™ DNA Extraction Solution (QE09050, Epicentre).

Blue White Colony Screening

The plasmids extracted from transfected cells were digested with DpnI (removes un-replicated input plasmid) and transformed into *E. coli* MBM7070 (lacZ$^{uag\_amber}$), which were grown on LB plates containing 50 µg/ml kanamycin, 1 mM IPTG and 0.03% Bluo-gal (Invitrogen/Life Technologies, Grand Island, NY) at 37° C. overnight and then at room temperature for another day (for maximal color development). To determine the mutation spectrum, white colonies were random picked up for Sanger sequencing.

DNA Library Preparation and Sequencing

Target genomic sites were PCR amplified by high-fidelity DNA polymerase PrimeSTAR HS (Clonetech) with primers flanking each examined sgRNA target site. Indexed DNA libraries were prepared by using the TruSeq ChIP Sample Preparation Kit (Illumina) with some minor modifications. Briefly, the PCR products amplified from genomic DNA regions were fragmented by Covaris S220. The fragmented DNAs were then PCR amplified by using the TruSeq ChIP Sample Preparation Kit (Illumina). After being quantitated with Qubit High-Sensitivity DNA kit (Invitrogen), PCR products with different tags were pooled together for deep sequencing by using the Illumina Hiseq 2500 (2×150) or Hiseq X-10 (2×150) at CAS-MPG Partner Institute for Computational Biology Omics Core, Shanghai, China. Raw read qualities were evaluated by FastQC. For paired ended sequencing, only R1 reads were used. Adaptor sequences and read sequences on both ends with Phred quality score lower than 28 were trimmed. Trimmed reads were then mapped with the BWA-MEM algorithm (BWA v0.7.9a) to target sequences. After being piled up with samtools (v0.1.18), indels and base substitutions were further calculated.

Indel Frequency Calculation

For Cpf1, indels were estimated in the aligned regions spanning from upstream 3 nucleotides to the downstream 48 nucleotides both according to PAM sites (55 bp). For Cas9, indels were estimated in the aligned regions spanning from upstream eight nucleotides to the target site to downstream 19 nucleotides to PAM sites (50 bp). Indel frequencies were subsequently calculated by dividing reads containing at least one inserted and/or deleted nucleotides by all the mapped reads at the same region.

Base Substitution Calculation

Base substitutions were selected at each position of the examined sgRNA (or crRNA) target sites that mapped with at least 1,000 independent reads, and obvious base substitutions were only observed at the targeted base editing sites. Base substitution frequencies were calculated by dividing base substitution reads by total reads.

Statistical Analysis

P values were calculated from one-tailed Student's T test in this study.

Results

Cpf1 (Cas12a) is another Cas protein that differs from Cas9 in several ways. This example tested two different Cpf1 for their ability to conduct base editing.

Figure 3:
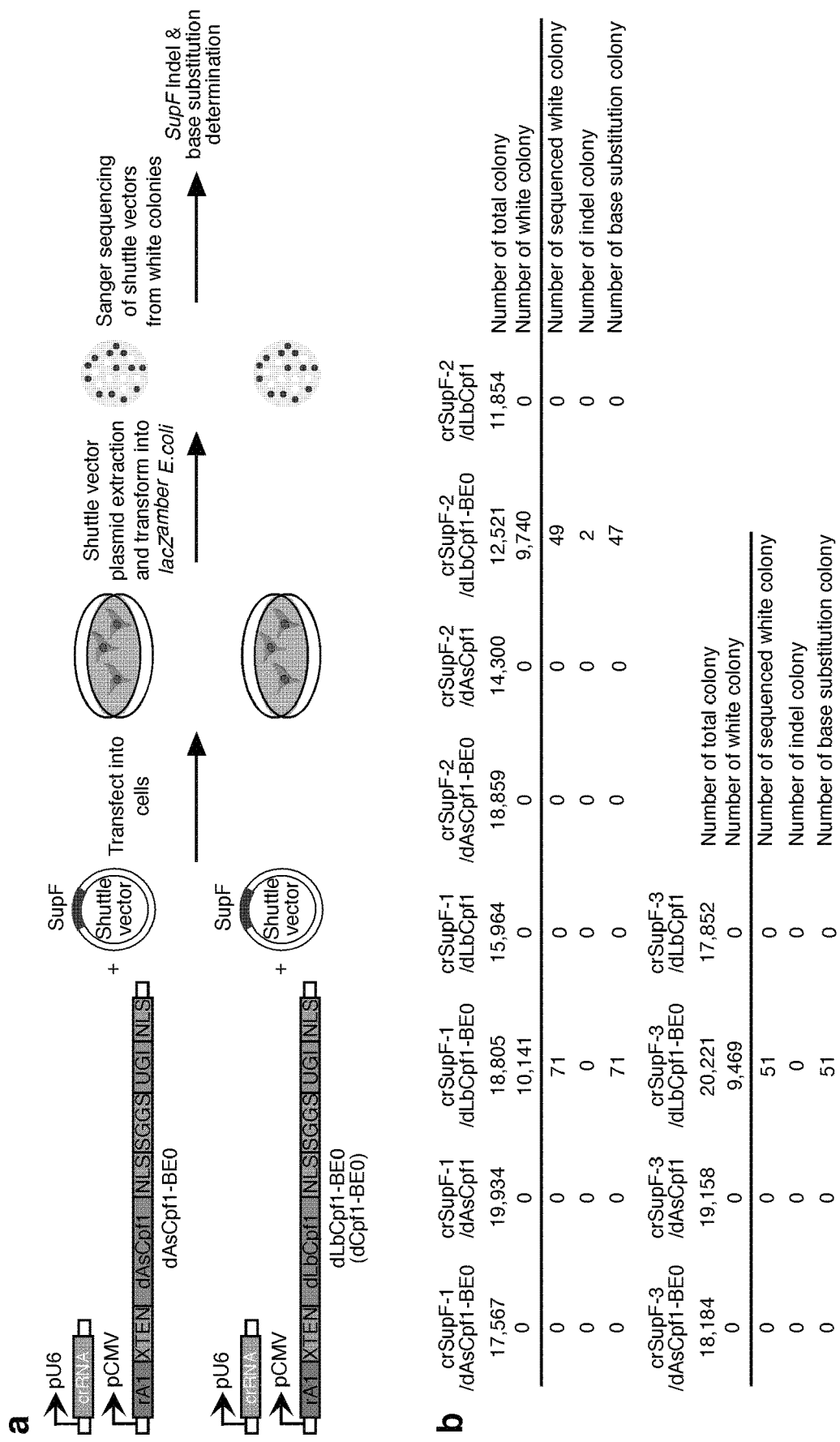
FIG. 3, with panels a-c. dLbCpf1-BE0 but not dAsCpf1-BE0 induced C-to-T base editing in episomal shuttle vector system. (a) Schematic diagram illustrating the procedures to determine the base editing induced by dLbCpf1-BE0 or dAsCpf1-BE0 in episomal shuttle vectors. (b) Number of E. coli colonies containing mutated shuttle vectors that were induced by dAsCpf1-BE0 or dLbCpf1-BE0. (c) C-to-T editing frequencies were determined at the indicated cytosines. The cytosines were counted with the base proximal to the PAM setting as position 1. Frequencies were calculated from data in (b). Means±s.d. were from three independent experiments. The sequences shown, from top to down and left to right, are SEQ ID NO:54-56.
Figure 4:
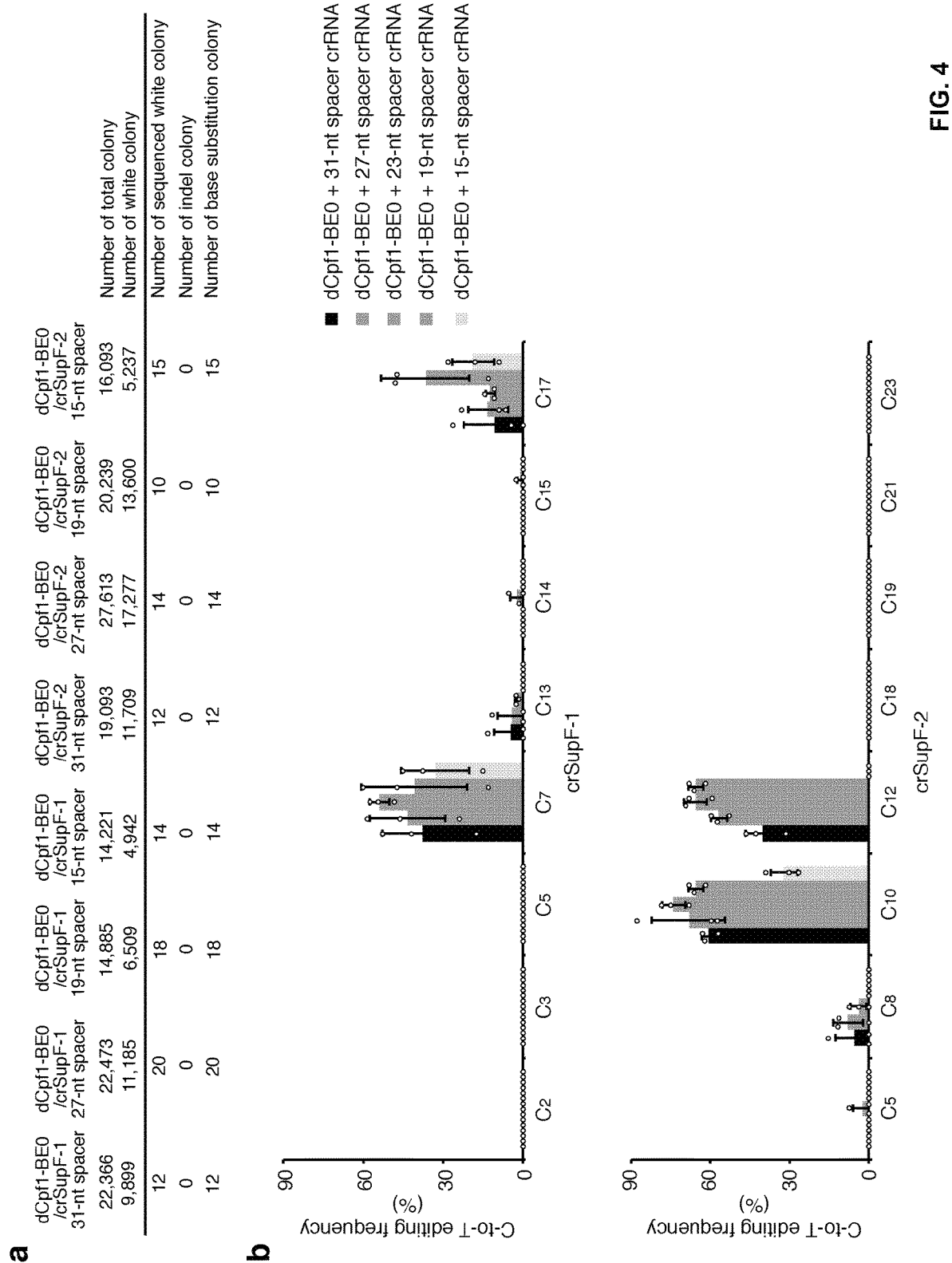
FIG. 4, with panels a-b. Effect of crRNA spacer length on editing efficiency. (a) Number of colonies containing mutated shuttle vectors that were induced by dCpf1-BE0 and crRNAs of different length. (b) C-to-T editing frequencies induced by dCpf1-BE0 and crRNAs of different length were determined at the indicated cytosines in episomal shuttle vectors. The crRNAs with the spacer length ranged from 19 to 27 nt showed similar base editing efficiencies at most of the editing positions. Frequencies were calculated from data in (a). Means±s.d. were from three independent experiments.

Rat APOBEC1 was fused to either catalytically inactive Acidaminococcus sp. Cpf1 (dAsCpf1) or catalytically inactive Lachnospiraceae bacterium Cpf1 (dLbCpf1) together with uracil DNA glycosylase inhibitor (UGI) to develop two dCpf1-based BEs, dAsCpf1-BE0 and dLbCpf1-BE0 (FIG. 3a). This example first tested their editing potential in an *E. coli* plasmid-derived episomal shuttle vector reporter system (FIG. 3a) that has been shown to be a sensitive tool to probe base substitutions in human cells. dLbCpf1-BE0 induced a high level of C-to-T base editing in the target regions (the editing frequency of single cytosine ranging from 44% to 74%), whereas dAsCpf1-BE0 did not show detectable base editing under similar conditions (FIG. 3b, 3c). Hence, this example used dLbCpf1-BEs in the rest of this study, and referred to them as dCpf1-BEs for simplicity. It was found that crRNAs with spacers ranged from 19 nt to 27 nt showed similar editing frequencies (FIG. 4).

Figure 5:
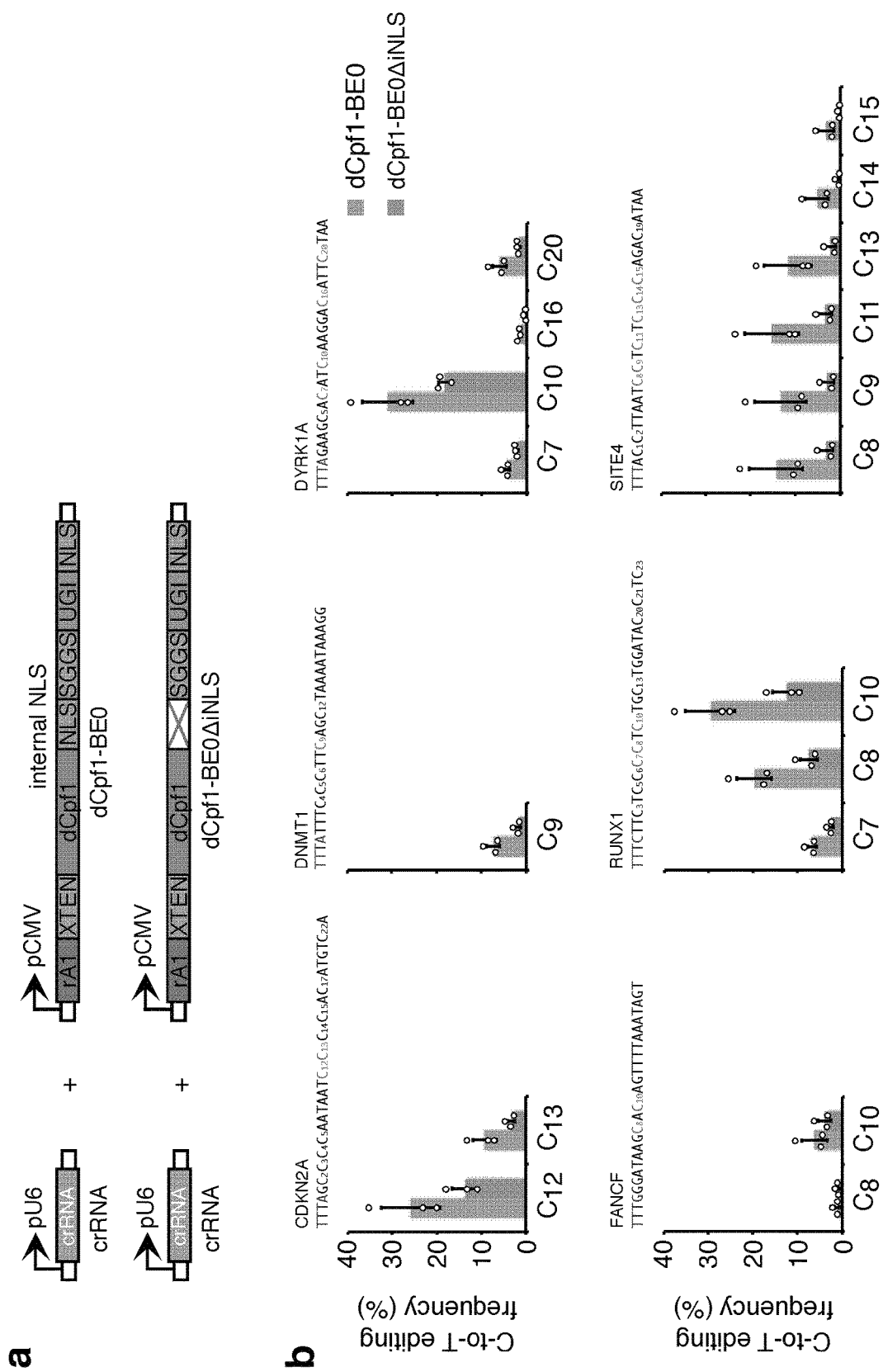
FIG. 5, with panels a-e. The internal NLS (iNLS) between dCpf1 and UGI is important for base editing induced by dCpf1-BE0. (a) Schematic diagram illustrating the design of expression vectors of dCpf1-BE0 and dCpf1-BE0ΔiNLS. (b) The C-to-T editing frequencies of the indicated cytosines were individually determined at different genomic target sites under the treatment of dCpf1-BE0 (blue) or dCpf1-BE0ΔiNLS (green). The sequences shown, from left to right and top to down, are SEQ ID NO:57-62. (c) The normalized C-to-T editing frequencies induced by dCpf1-BE0 and dCpf1-BE0ΔiNLS in genomic DNA, setting the ones induced by dCpf1-BE0 as 100%. (d) Statistical analysis of the normalized C-to-T editing frequencies. The dCpf1-BE0 induced significantly higher C-to-T editing frequencies than dCpf1-BE0ΔiNLS. P values, one-tailed Student's T test. The median, interquartile range (IQR) and 1.5×IQR are shown. n=54 independent samples from 3 independent experiments. (e) The indel frequencies were determined at indicated loci in genomic DNA. 293FT cells were either treated with dCpf1-BE0 (blue), with dCpf1-BE0ΔiNLS (green) or non-transfected (gray) before deep sequencing. Asterisk denotes an unusually high basal indel frequency (or amplification, sequencing, alignment artifact) at the examined RUNX1 site in the non-transfected 293FT cells. Means±s.d. were from three independent experiments.
Figure 6:
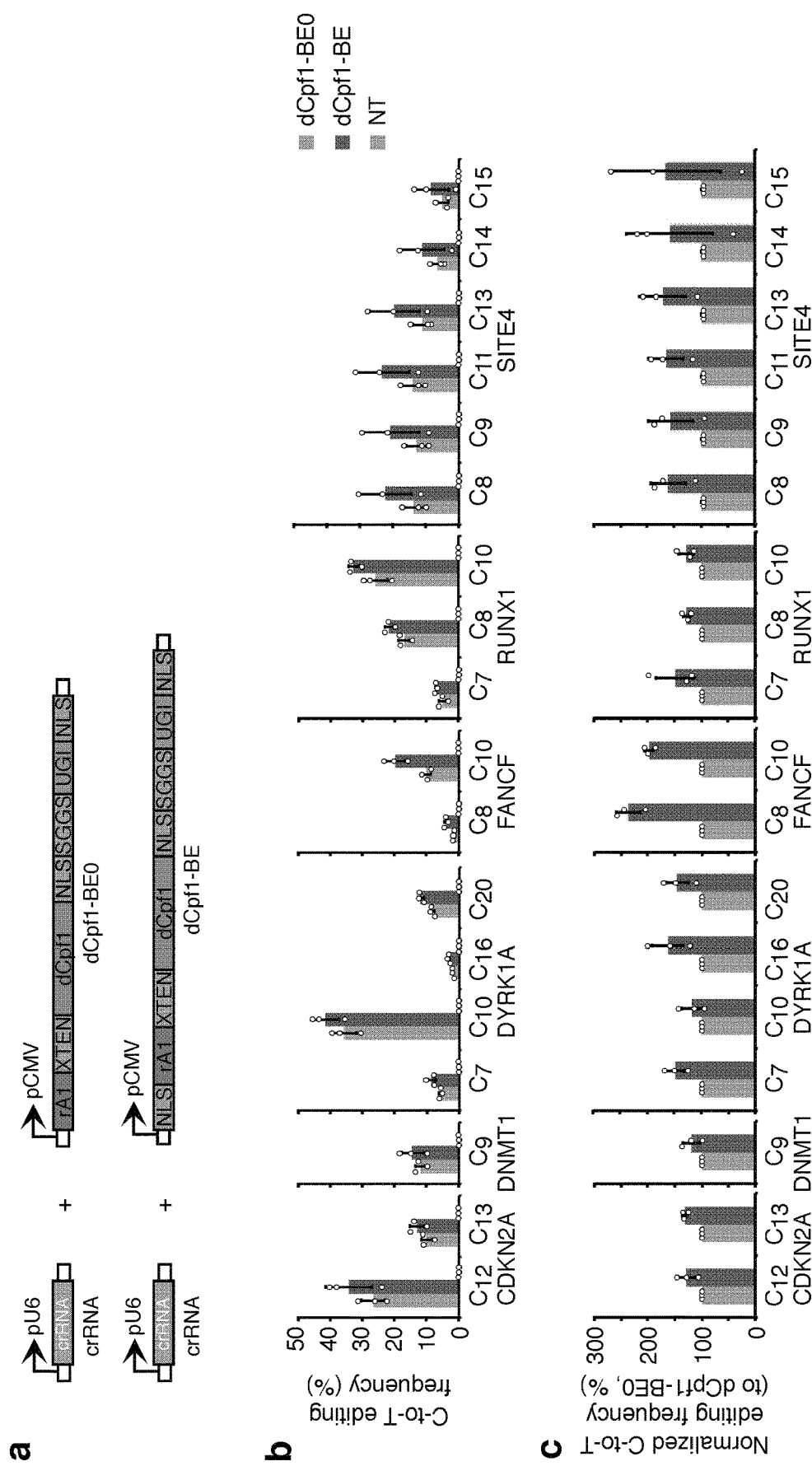
FIG. 6, with panels a-e. Additional N-terminal NLS enhanced the base editing efficiency of dCpf1-BE in genomic DNA. (a) Schematic diagram illustrating the design of expression vectors of dCpf1-BE0 and dCpf1-BE. (b) The C-to-T editing frequencies of the indicated cytosines were individually determined at different genomic target sites. 293FT cells were either treated with dCpf1-BE0 (blue), dCpf1-BE (purple) or left non-transfected (gray) before deep sequencing. (c) The normalized C-to-T editing frequencies induced by dCpf1-BE0 and dCpf1-BE in genomic DNA, setting the ones induced by dCpf1-BE0 as 100%. (d) Statistical analysis of the normalized C-to-T editing frequencies. The dCpf1-BE induced significantly higher C-to-T editing frequencies than dCpf1-BE0. P values, one-tailed Student's T test. The median, IQR and 1.5×IQR are shown. n=54 independent samples from 3 independent experiments. (e) The indel frequencies were determined at indicated loci in genomic DNA under different conditions. Asterisk denotes an unusually high basal indel frequency (or amplification, sequencing, alignment artifact) at the examined RUNX1 site in the non-transfected 293FT cells. Means±s.d. were from three independent experiments.

Next, this example analyzed the performance of dCpf1-BE0 at endogenous genomic sites in mammalian cells. dCpf1-BE0 can also induce base editing at targeted genomic sites, resulting in 6%-37% C-to-T editing frequency (mean 20%, counting the highest editing frequency of single cytosine in each target, FIGS. 5a and 5b). Deletion of internal SV40 nuclear localization sequence (iNLS) between dCpf1 and UGI dramatically reduced the base editing efficiency (FIG. 5b-5d, comparing dCpf1-BE0ΔiNLS to dCpf1-BE0). dCpf1-BE with an additional copy of N-terminal SV40NLS increased base editing efficiencies at all tested genomic loci (FIG. 6a-6d, $P=3\times10^{-11}$).

Figure 7:
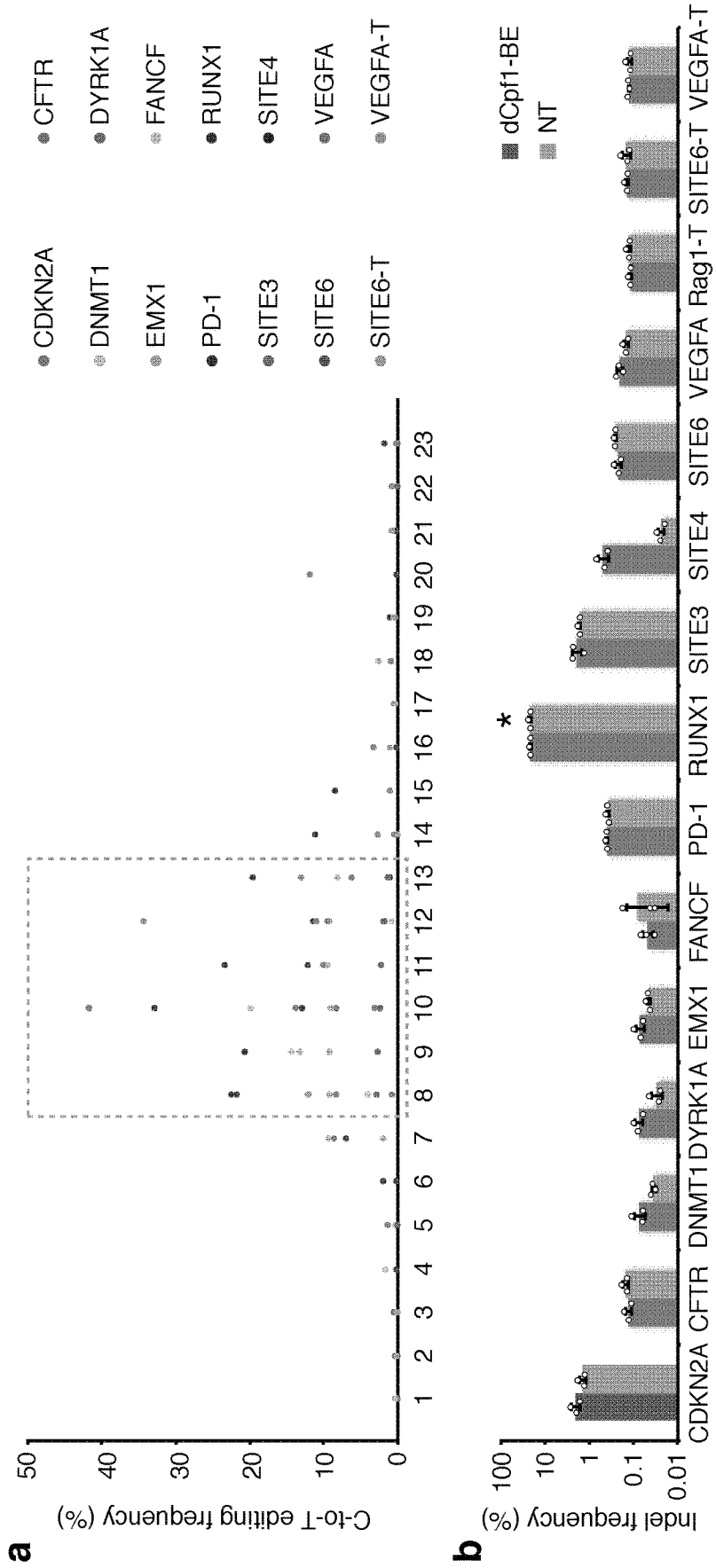
FIG. 7, with panels a-d. Features of dCpf1-BE-induced base editing. (a) Summary of the base editing frequency at each cytosine in the spacer region for the indicated 14 crRNAs. These data show that the major editing window ranges from the position 8 to 13 in spacer region. (b) The indel frequencies were determined at indicated loci in genomic DNA under different conditions. 293FT cells were either treated with dCpf1-BE (purple) or non-transfected (gray) before deep sequencing. Asterisk denotes an unusually high basal indel frequency (or amplification, sequencing, alignment artifact) at the examined RUNX1 site in the non-transfected 293FT cells. Means±s.d. were from three independent experiments. (c) The fractions of cytosine substitutions induced by dCpf1-BE were individually determined at the indicated cytosines. (d) Statistical analysis showed that the C-to-T fraction of base editing outcome induced by dCpf1-BE was significantly higher than that induced by nCas9-BE3. The median and IQR are shown. P values, one-tailed Student's T test. n=42 independent samples from 3 independent experiments.
Figure 8:
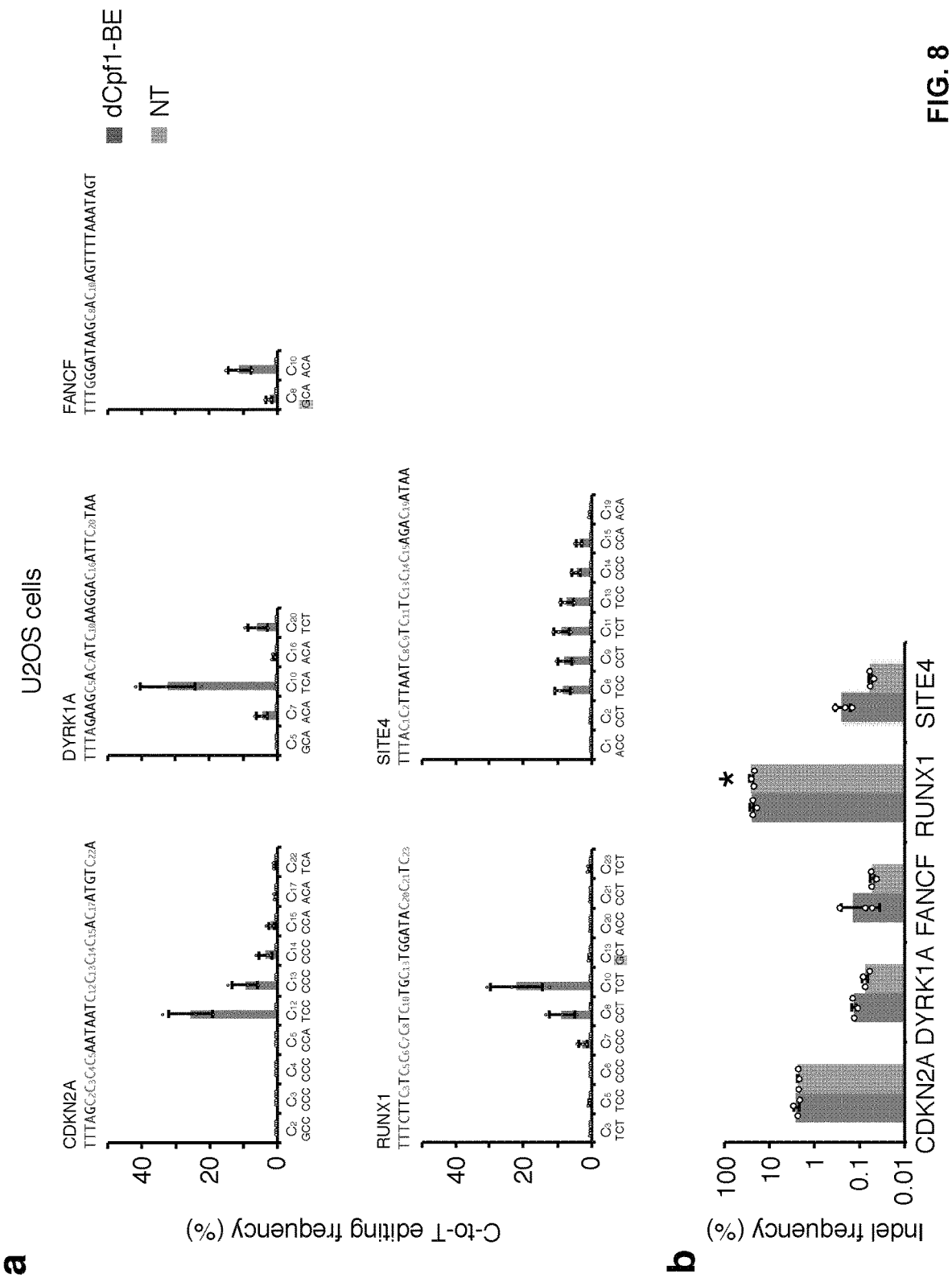
FIG. 8, with panels a-c. Base editing was induced by dCpf1-BE in U2OS cells. (a) The C-to-T editing frequencies of the indicated cytosines were individually determined at the indicated genomic target sites. U2OS cells were either treated with dCpf1-BE (purple) or non-transfected (gray) before deep sequencing. The sequences shown, from left to right and top to down, are SEQ ID NO:63-67. (b) The indel frequencies were determined at indicated loci in genomic DNA under different conditions. Asterisk denotes an unusually high basal indel frequency (or amplification, sequencing, alignment artifact) at the examined RUNX1 site in the non-transfected U2OS cells. (c) The fractions of cytosine substitutions induced by dCpf1-BE were individually determined at the indicated cytosines. (a, b) Means±s.d. were from three independent experiments.

To evaluate its efficacy in general, this example tested dCpf1-BE at 12 target sites with the TTTV PAM sequence and 3 target sites with the TTTT PAM sequence (FIG. 1a). Among the 12 target sites with the TTTV PAM sequence, dCpf1-BE induced base editing (highest single C-to-T conversion frequency ranged from 11% to 46%, mean 22%) at ten sites and inefficient base editing (frequency less than 5%, mean 3%) at two sites. At sites with the TTTT PAM sequence, dCpf1-BE induced relatively low efficiencies (~10% editing at two sites and no detectable editing for the other one). Meanwhile, the main editing window of dCpf1-BE ranges from positions 8 to 13, counting the base next to the PAM as position 1 (FIG. 7a), and dCpf1-BE barely induced C-to-T base editing at the cytosines following a guanosine (FIG. 1a). Notably, as dCpf1 is used in dCpf1-BEs, unwanted indels were not generally induced and high fractions of C-to-T conversions were achieved at tested sites (FIGS. 5e, 6e, 7b and 7c). Similarly, dCpf1-BE induced base editing in another human cell line U2OS at all examined sites (highest single C-to-T conversion frequency ranged from 10% to 33%, mean 20%) with low levels of unwanted indels and non-C-to-T substitutions (FIG. 8).

Figure 9:
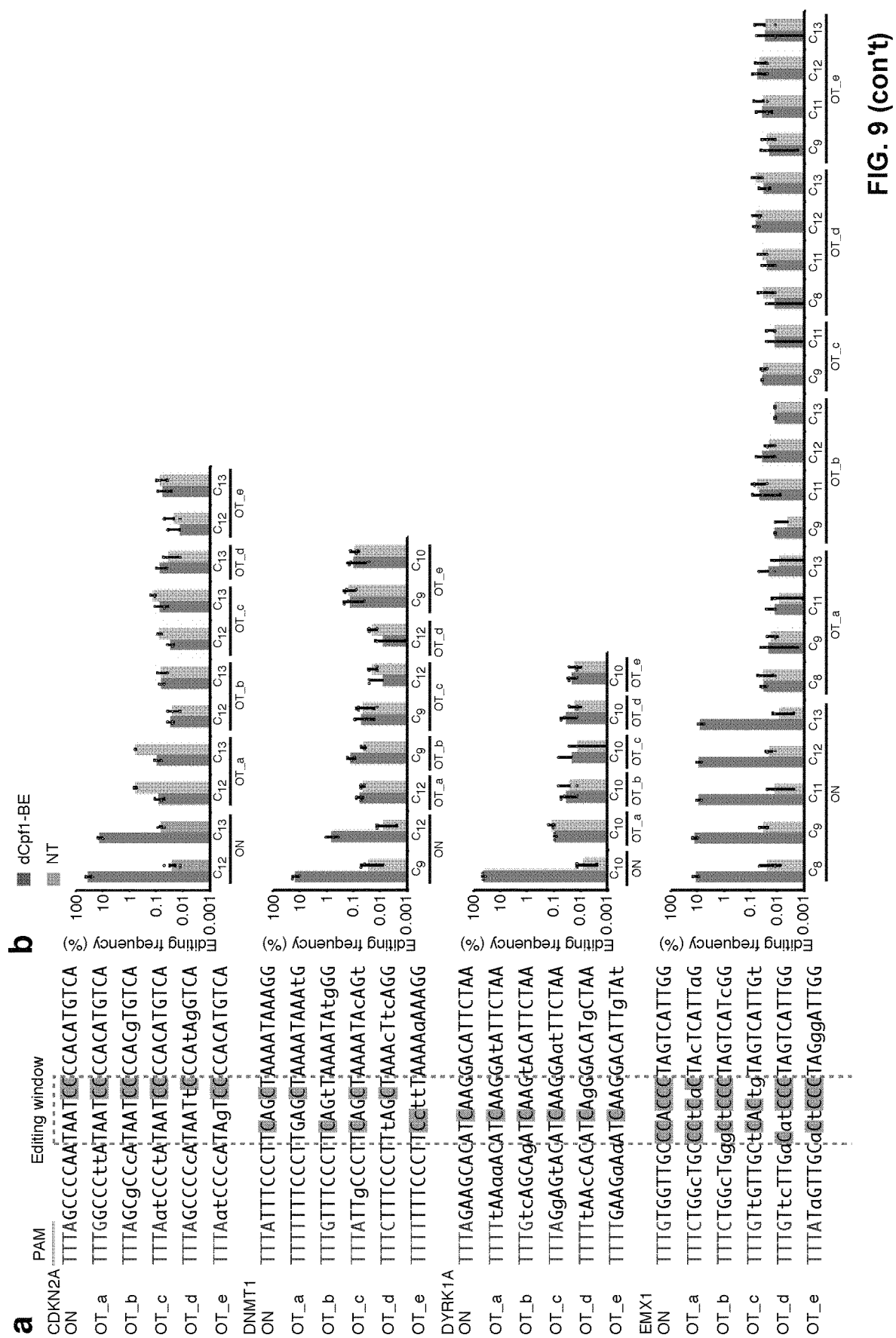
FIG. 9, with panels a-b. Determination of base editing induced by dCpf1-BE at predicted off-target sites. (a) The sequences of on- and off-target sites for the indicated crRNAs. The cytosines were counted with the base proximal to the PAM setting as position 1. The sequences shown, from top to down, are SEQ ID NO:68-115. (b) The C-to-T editing frequencies of the indicated cytosines were individually determined at the indicated on- and off-target sites. 293FT cells were either treated with dCpf1-BE (purple) or non-transfected (gray) before deep sequencing. Means±s.d. were from three independent experiments.
Figure 10:
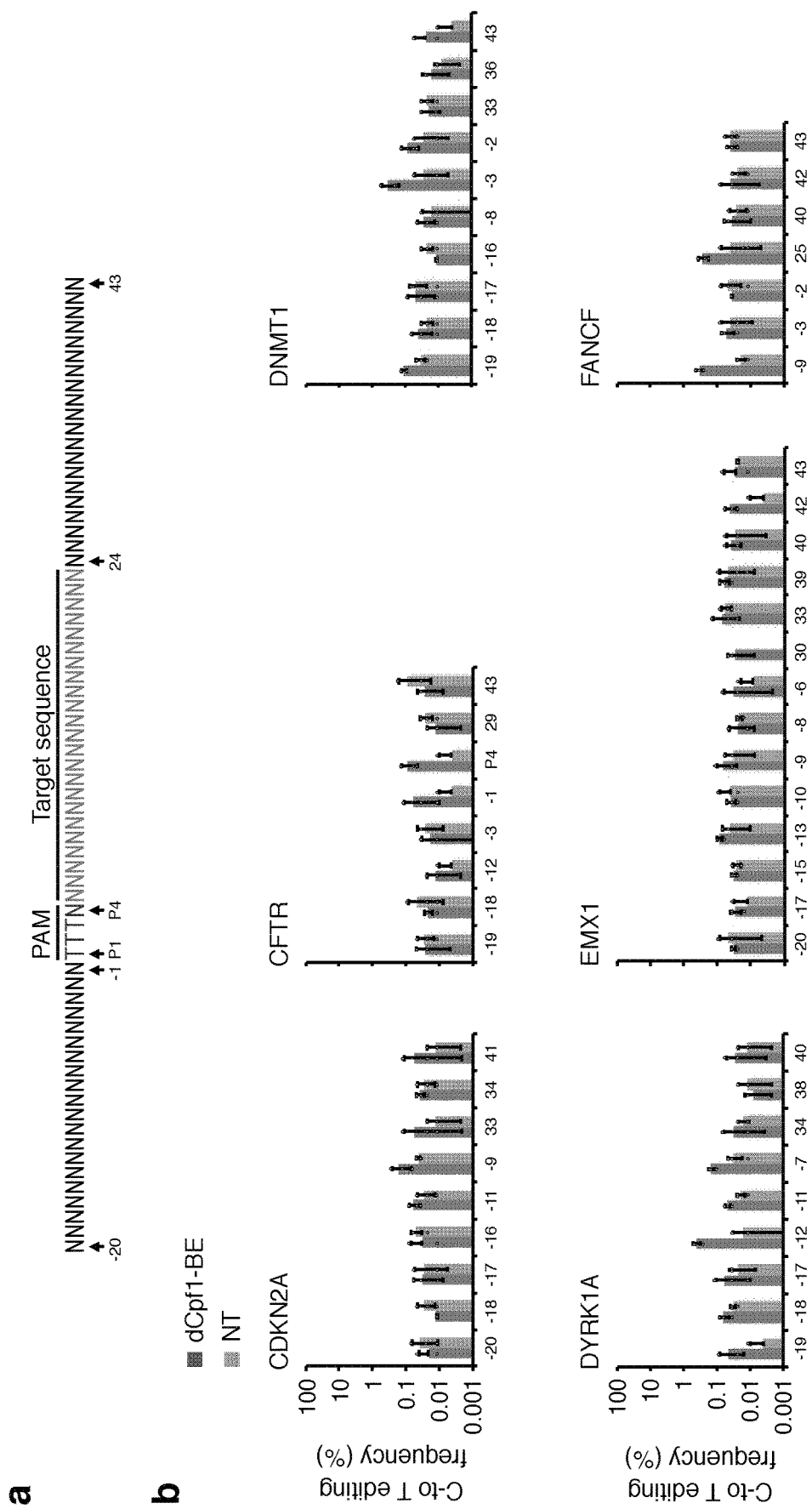
FIG. 10, with panels a-b. No substantial C-to-T editing was detected in the region outside of the spacer. (a) Schematic diagram illustrating the PAM region, the 20-nt region upstream of PAM and the 20-nt region downstream of spacer. (b) The C-to-T editing frequencies of the indicated cytosines outside of the spacer region were individually determined at the indicated sites. 293FT cells were either treated with dCpf1-BE (purple) or non-transfected (gray) before deep sequencing. Means±s.d. were from three independent experiments.

Furthermore, this example examined possible OT base editing induced by dCpf1-BE at 40 predicted OT sites for eight crRNAs (five OT sites per crRNA) and found OT base editing for one crRNA at three sites (FIG. 9). Finally, assaying a 44-nt region outside the spacer sequence, this example rarely detected C-to-T base conversions (FIG. 10).

Next, this example compared the editing efficiency of dCpf1-BE with those of different Cas9-BEs at 8 target sites where the editing windows of dCpf1-BE (position 8-13) and Cas9-BEs (position 4-8) overlap. As indicated in FIG. 1b, dCpf1-BE generally induced higher editing frequencies than dCas9-BE2 at the 14 commonly editable cytosines, and reached or exceeded the editing level induced by nCas9-BE3 at five out of the 14 editable cytosines (FIG. 1b, C-to-T editing frequency). While, it cannot be ruled out that the increased number of NLS and a longer linker between dCpf1 and UGI contributed to the performance of dCpf1-BE compared to nCas9-BE3. At the other 9 commonly editable cytosines, dCpf1-BE induced lower base editing level than nCas9-based BE3 (FIG. 1b). Notably, in all cases, dCpf1-BE induced fewer indels and non-C-to-T substitutions than nCas9-BE3 (FIG. 1b and FIG. 7d, P=5×10$^{-10}$).

Figure 2:
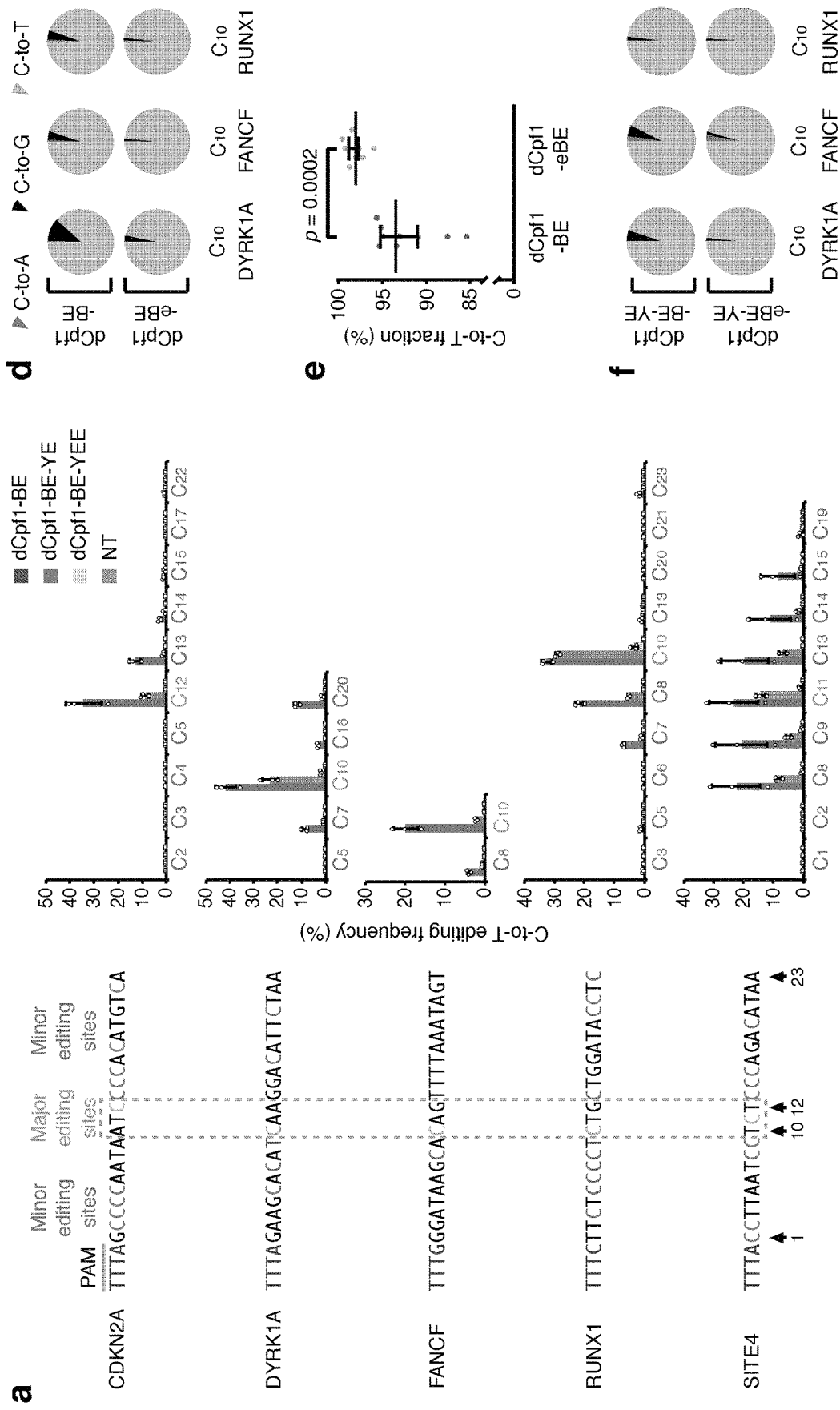
FIG. 2, with panels a-h. Improvements of dCpf1-BE. (a) Mutating APOBEC1 in dCpf1-BE to narrow down editing window. The C-to-T editing frequency at every single cytosine was individually determined in the indicated genomic target sites under different conditions. The target site sequences and the narrowed editing windows of dCpf1-BE are shown. The major editing sites ($C_{10}$-$C_{12}$) are in salmon and the minor editing sites ($C_1$-$C_9$ and $C_{13}$-$C_{23}$) are in green. The sequences shown, from top to bottom, are SEQ ID NO:49-53. (b) The ratios of major editing to minor editing were determined at the indicated genomic target sites. (c) Statistical analysis of the normalized ratios of major editing to minor editing, setting the ones induced by dCpf1-BE as 100%. The dCpf1-BE-YE induced significantly higher ratio of major editing to minor editing. The median, interquartile range (IQR) and 1.5×IQR are shown. n=15 independent samples from 3 independent experiments. (d-g) The addition of free UGI enhances the purity of editing outcomes induced by dCpf1-BEs. The fractions (d, f) and statistical analyses (e, g) of cytosine substitutions at the indicated editing positions under different conditions. (e, g) The dCpf1-eBE and dCpf1-eBE-YE induced significantly purer C-to-T editing outcomes than dCpf1-BE and dCpf1-BE-YE. The median and IQR are shown. n=9 independent samples from 3 independent experiments. (h) Summary of Cas9-based and dCpf1-based BEs. Left, schematic diagrams illustrate the complexes of Cas9-BE/sgRNA/target DNA and dCpf1-BE/crRNA/target DNA. Right, list of relevant features in Cas9-based and dCpf1-based BE systems. Comparisons are based on base editing at DYRK1A, FANCF and RUNX1 target sites. (a, b) Means±s.d. were from three independent experiments. (c, e, g) P value, one-tailed Student's T test.
Figure 11:
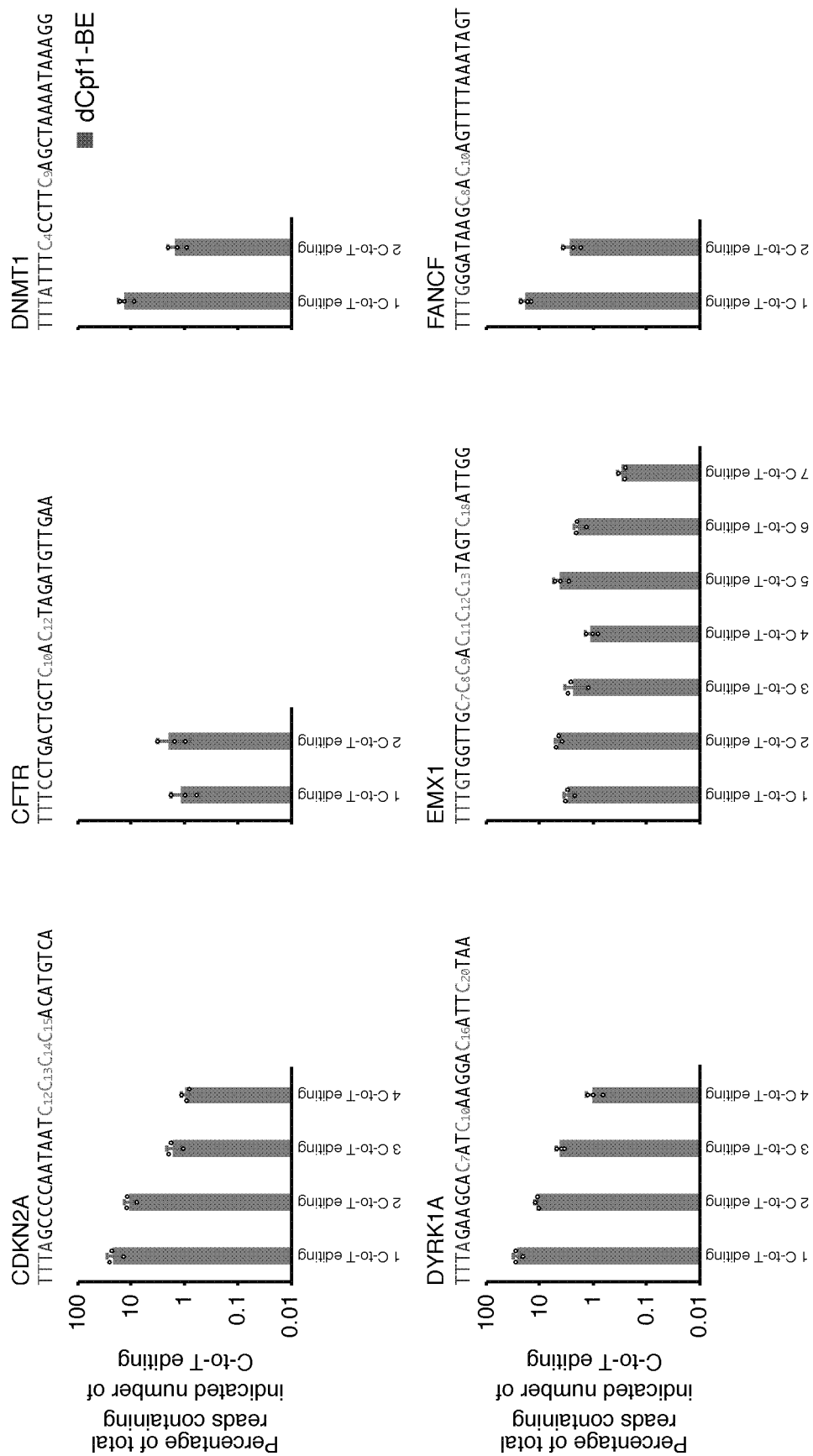
FIG. 11. Multiple C-to-T editing was induced by dCpf1-BE when more than one cytosines are in the spacer region. The frequencies of single and multiple C-to-T editing induced by dCpf1-BE at the indicated cytosines were determined at different genomic target sites. The deep sequencing data are same as in FIG. 1a. Means±s.d. were from three independent experiments. The sequences shown, from left to right and top to down, are SEQ ID NO:116-129.
Figure 12:
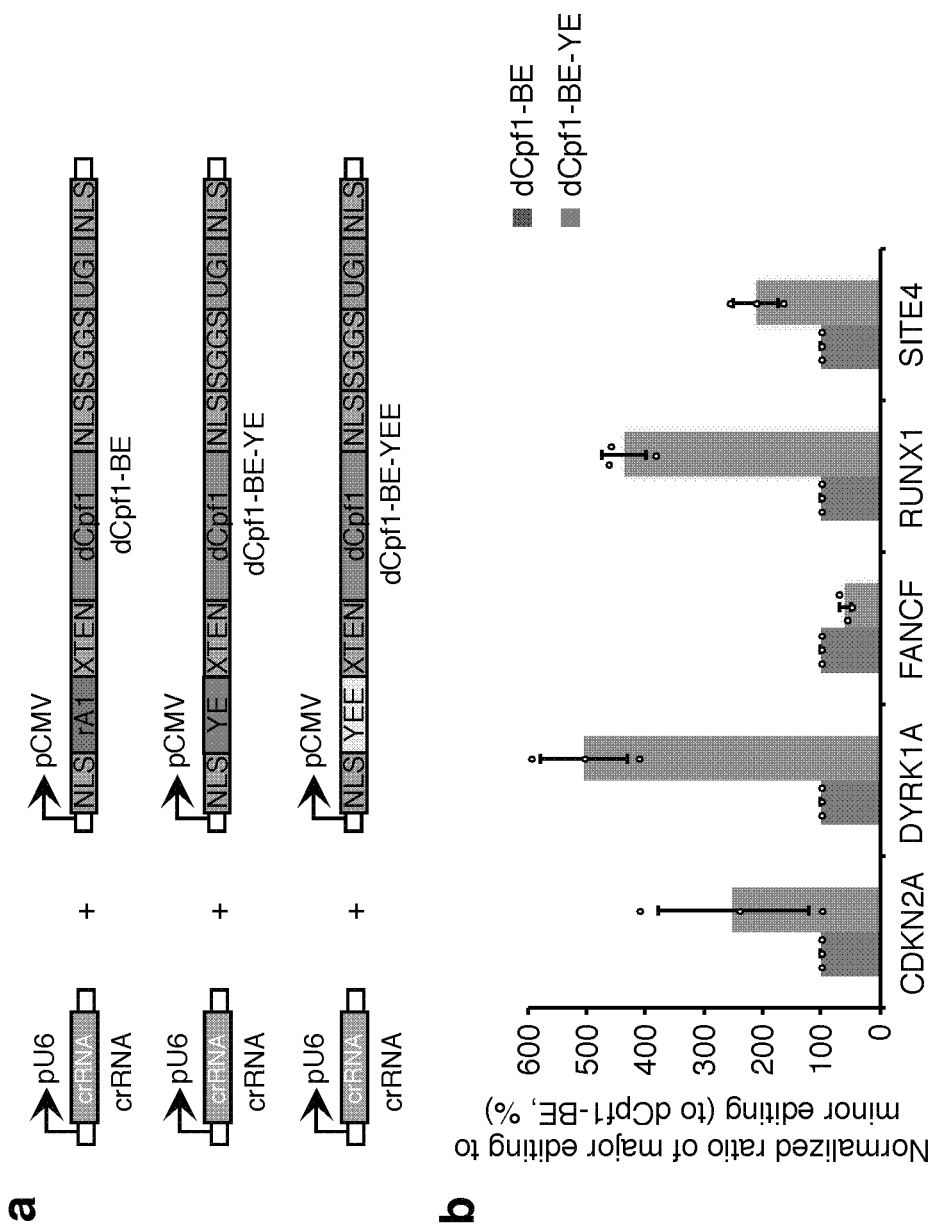
FIG. 12, with panels a-e. W90Y and R126E mutations in rat APOBEC1 (rA1) narrowed the base editing window to 3 nt. (a) Schematic diagram illustrating the design of expression vectors of dCpf1-BE, dCpf1-BE-YE and dCpf1-BE-YEE. (b) The normalized ratios of major editing to minor editing induced by dCpf1-BE (purple) and dCpf1-BE-YE (magenta), setting the ones induced by dCpf1-BE as 100%. (c) The fractions of single and multiple C-to-T conversions induced by dCpf1-BE and dCpf1-BE-YE. The sequences shown, from left to right and top to down, are SEQ ID NO:130-134. (d) Statistical analysis showed that the fraction of single C-to-T conversion induced by dCpf1-BE-YE was significantly higher than that induced by dCpf1-BE. P values, one-tailed Student's T test. The median and IQR are shown. n=15 independent samples from 3 independent experiments. (e) The indel frequencies were determined at the indicated genomic loci from the 293FT cells transfected with dCpf1-BE (purple), dCpf1-BE-YE (magenta), dCpf1-BE-YEE (yellow) or non-transfected (gray). Asterisk denotes an unusually high basal indel frequency (or amplification, sequencing, alignment artifact) at the examined RUNX1 site in the non-transfected 293FT cells. (b, e) Means±s.d. were from three independent experiments.

To further narrow the 6-nt editing window of dCpf1-BE (positions 8 to 13, FIG. 7a) and reduce multiple C-to-T base conversion (FIG. 11), this example introduced mutations (W90Y and R126E) into the APOBEC domain (FIG. 12a). In four out of five tested genomic loci, dCpf1-BE-YE retained ~30% to 90% of original editing efficiencies at its highly preferred editing positions (major editing sites, positions 10 to 12, FIG. 2a) but showed greatly reduced editing efficiencies elsewhere in the spacer region (minor editing sites, positions 1 to 9 and 13-23, FIG. 2a), which led to the increased ratios of major editing to minor editing (FIG. 2b). After being normalized to dCpf1-BE (FIG. 12b), the ratios of major editing to minor editing induced by dCpf1-BE-YE increased about 2 to 3 folds (FIG. 2c, P=0.0005). dCpf1-BE-YE also yielded a higher fraction of single C-to-T fraction than dCpf1-BE when two or more cytosines are in the editing window (FIG. 12c, 12d). dCpf1-BE-YEE with a third mutation (R132E) decreased base editing frequency at all editing positions to near background level (FIG. 2a). Similar to dCpf1-BE, both dCpf1-BE-YE and dCpf1-BE-YEE barely induced unwanted indels (FIG. 12e). Collectively, base editing can be specifically narrowed into a 3-nt window (positions 10 to 12) by dCpf1-BE-YE.

Figure 13:
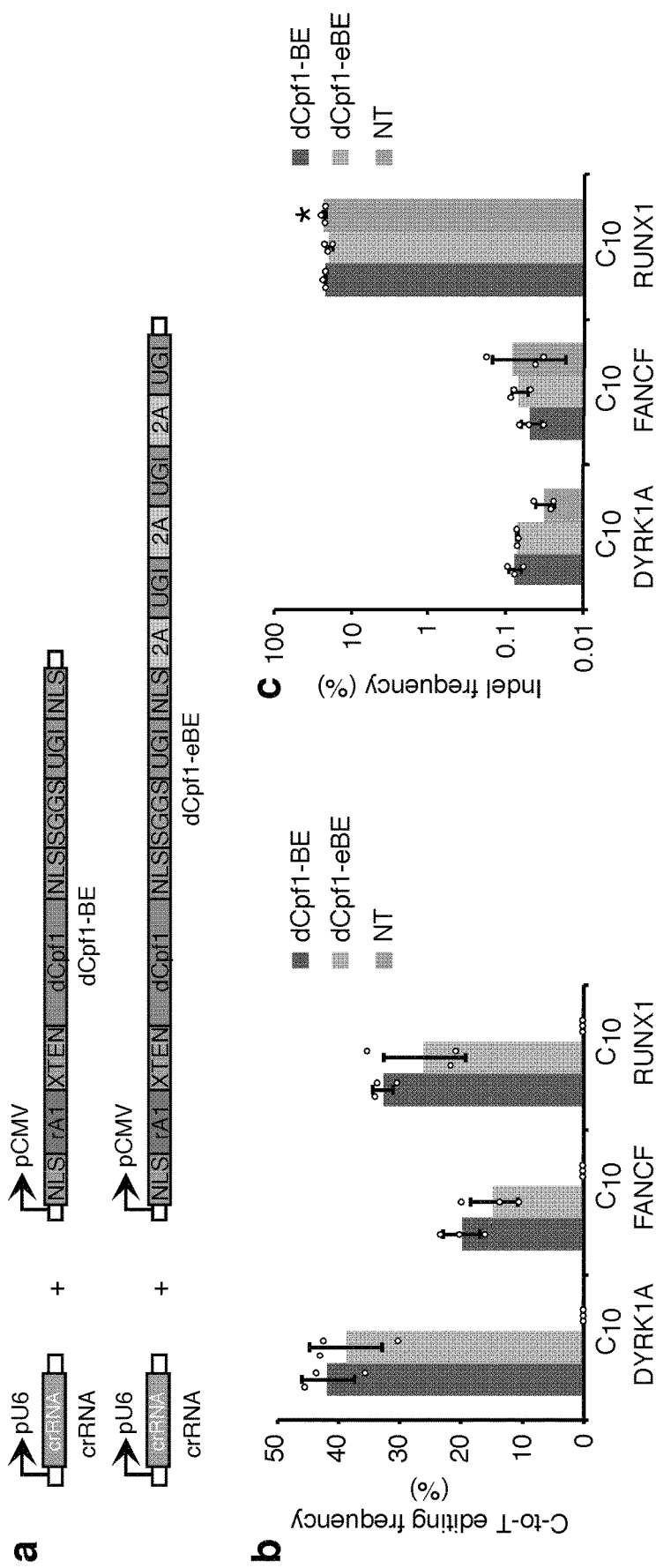
FIG. 13, with panels a-f. The fusion of three copies of 2A-UGI sequences did not substantially affect editing efficiency and induced no detectable indel formation. (a) Schematic diagram illustrating the design of expression vectors of dCpf1-BE and dCpf1-eBE. (b) The base editing frequencies induced by dCpf1-BE (purple) and dCpf1-eBE (green) were determined at indicated positions in genomic DNA. (c) The indel frequencies were determined at the indicated genomic loci. The 293FT cells were either treated with dCpf1-BE (purple), dCpf1-eBE (green) or left non-transfected (gray) before deep sequencing. (d) Schematic diagram illustrating the design of expression vectors of dCpf1-BE-YE and dCpf1-eBE-YE. (e) The base editing frequencies induced by dCpf1-BE-YE (magenta) and dCpf1-eBE-YE (brown) were determined at the indicated positions in genomic DNA. (f) The indel frequencies were determined at the indicated genomic. The 293FT cells were either treated with dCpf1-BE-YE (magenta), dCpf1-eBE-YE (brown) or non-transfected (gray) before deep sequencing. Asterisk denotes an unusually high basal indel frequency (or amplification, sequencing, alignment artifact) at the examined RUNX1 site in the non-transfected 293FT cells. Means±s.d. were from three independent experiments.

The non-C-to-T substitutions induced by dCpf1-BE are fewer than those induced by nCas9-BE3 (FIG. 1b), but still noticeable at some editing sites (DYRK1A-$C_{10}$, FANCF-$C_{10}$ and RUNX1-$C_{10}$, FIG. 1b, fractions of cytosine substitutions). As shown in Example 2, co-expressing extra UGI proteins can substantially reduce these unintended non-C-to-T substitutions. This example, thus, added three copies of self-cleaving peptide 2A (2A)-UGI sequences to the 3' end of dCpf1-BE coding region to construct dCpf1-eBE (FIG. 13a). The formation of non-C-to-T substitutions was suppressed in dCpf1-eBE-mediated editing (FIG. 2d). As a result, fraction of C-to-T substitutions was further enhanced (FIG. 2e, P=0.0002) while the editing efficiencies remained largely unchanged (comparing dCpf1-eBE with dCpf1-BE, FIG. 13b). Similarly, the C-to-T fraction was also increased in dCpf1-eBE-YE-mediated base editing (FIG. 2f, 2g, P=0.007 and FIG. 13d) with little influence on the editing efficiency (FIG. 13e). Consistently, both dCpf1-eBE and dCpf1-eBE-YE induced almost undetected indels at all examined genomic loci (FIG. 13c, 13f).

Figure 14:
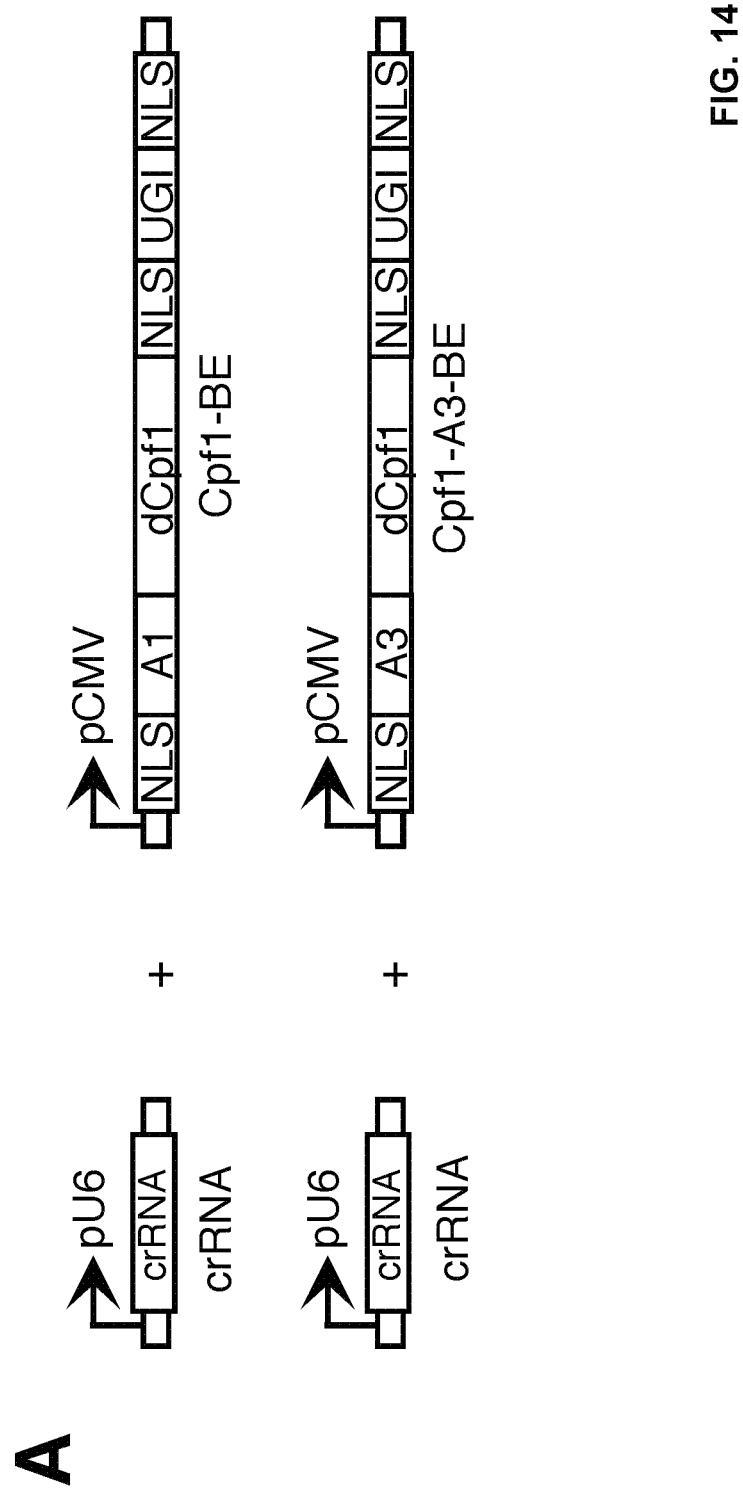
FIG. 14, with panels A-B. (A) Schematic diagram illustrating the design of expression vectors of Cpf1-BE and Cpf1-A3-BE. (B) The base editing efficiency induced by Cpf1-A3-BE and Cpf1-BE were determined at the indicated sites in genomic DNA. The base editing efficiency of Cpf1-A3-BE is higher than that of Cpf1-BE (positions 7 and 10 at DYRK1A site and positions 7, 8 and 10 at RUNX1 site). The sequences shown, from left to right and top to down, are SEQ ID NO:135-140.
Figure 15:
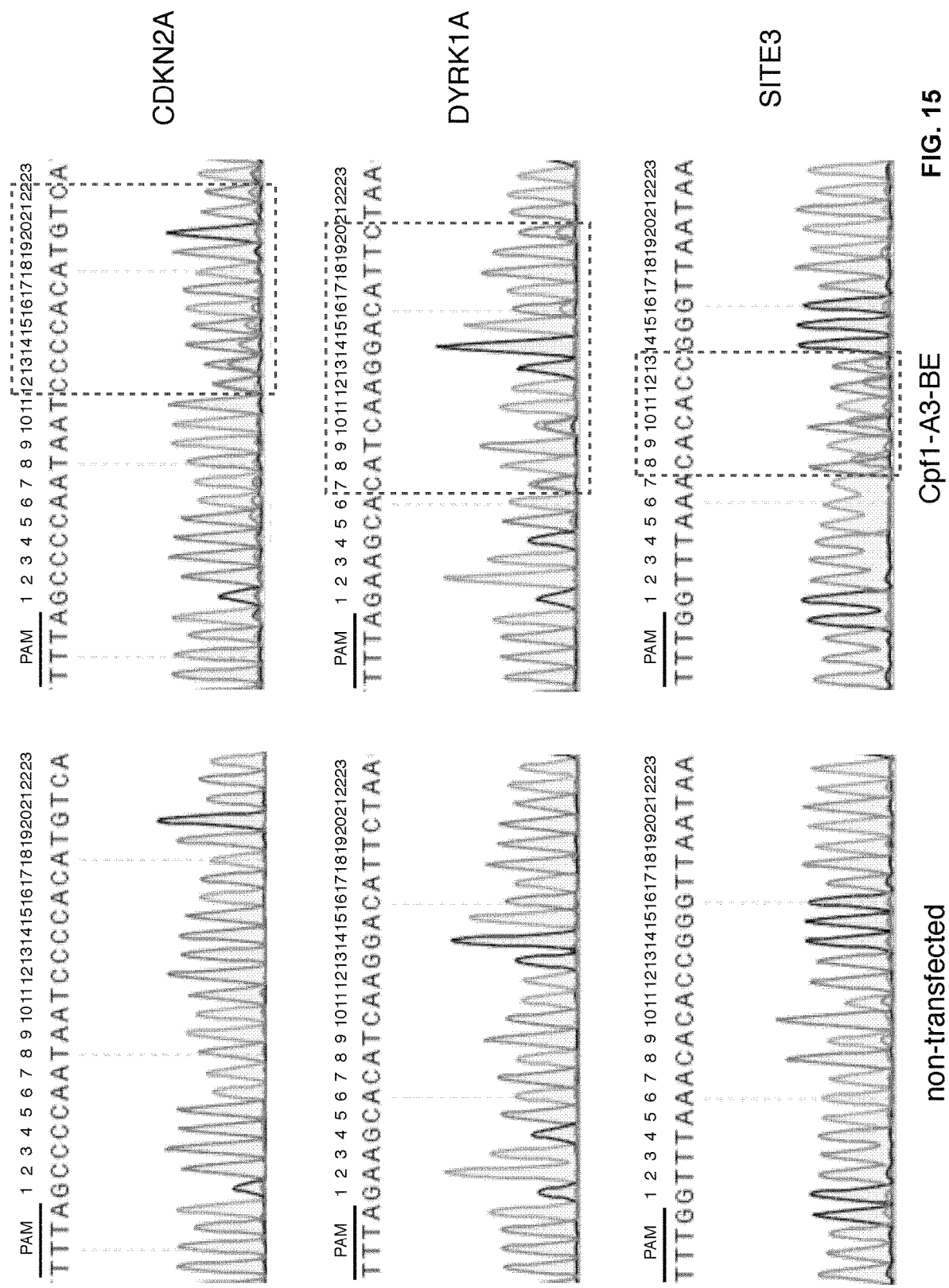
FIG. 15. Editing window of Cpf1-A3-BE. The editing window of Cpf1-A3-BE spans from positions 6 to 22 in the tested protospacer region. The sequences shown, from left to right and top to down, are SEQ ID NO:141-150.

In another experiment, dCpf1 was fused to APOBEC3 (A3) to generate a dCpf1-A3-BE editor (FIG. 14A). Like the Cpf1-A1-based editors, this Cpf1-A3 fusion editor had greatly improved editing frequency over Cas9 based editors (FIG. 14B). The editing window of Cpf1-A3-BE was from position 6 to 22 (FIG. 15). The instant inventors have recently discovered that mutations W104A, Y130F, D131Y, D131E, and Y132D can narrow the editing window of A3, consistent with the mutations tested in A1.

In summary, this example developed a series of CRISPR-Cpf1-based BEs, which can perform targeted base editing with very low levels of indel formation and non-C-to-T substitutions (FIG. 2h) and facilitate base editing in A/T-rich regions.

Example 2: Enhanced Base Editing by Co-Expression of Free Uracil DNA Glycosylase Inhibitor Compared to earlier generations of BEs (BE1 and BE2), the latest BE3 achieved much higher base editing frequencies by substituting catalytically-dead Cas9 (dCas9) with Cas9 nickase (nCas9). Because BEs achieve gene corrections without introducing DNA double-strand breaks (DSBs), unwanted indels converted from DSBs through non-homologous end joining (NHEJ) were thought to be excluded in base editing. However, non-negligible levels of indels (~4%-12%) were still observed in BE3-mediated base editing. In addition, unwanted non-C-to-T (i.e., C-to-A or C-to-G) substitutions were observed, and the frequencies of C-to-A/C-to-G substitutions could be as high as that of C-to-T substitution in some examined cases. The existence of unwanted indels and C-to-A/C-to-G substitutions compromises the fidelity of base editing outcome.

Figure 16:
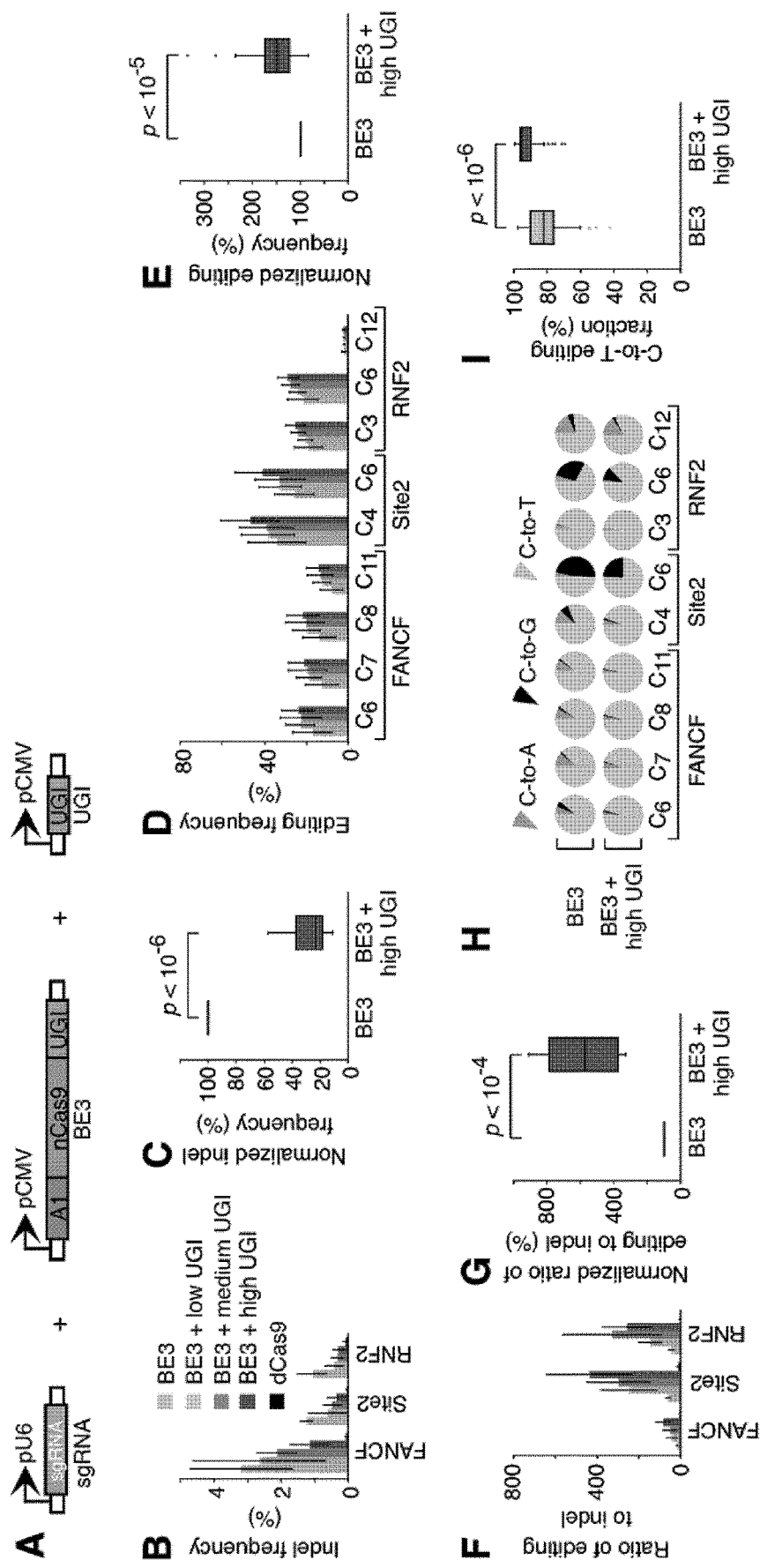
FIG. 16, with panels A-R. Enhanced base editing system. (A-I) Enhanced base editing by co-expressing BE3 and free UGI from separate vectors in 293FT cells. Schematic diagram illustrating the design of sgRNA, BE3 and UGI expression vectors (A). The indel frequency (B), the C-to-T editing frequency at the indicated position of the sgRNA target region (D), the ratio of desired C-to-T editing to unwanted indels (F) and the fractions of C-to-T, C-to-A and C-to-G substitutions (H) were individually determined at the specified genomic sites for the indicated conditions and plotted as follows: orange represents BE3, faint blue represents BE+low UGI, blue represents BE3+medium UGI, dark blue represents BE3+high UGI and black represents dCas9. The positions of edited Cs in the sgFANCF, sgSite2 and sgRNF2 target regions were indicated with the base distal from the PAM set as position 1. Statistical analyses highlighted the significant differences between BE3 (orange) and BE3+high UGI (dark blue) in indel frequency (C), in C-to-T editing frequency at the indicated position within sgRNA target region (E), in the ratio of desired C-to-T editing to unwanted indels (G) and in the fraction of C-to-T substitution (I). (J-R) Enhanced base editing by eBE-S1 and eBE-S3 in 293FT cells. Schematic diagram illustrating the design of sgRNA, BE3, eBE-S1 and eBE-S3 expression vectors (J). The indel frequency (K), the C-to-T editing frequency (M), the ratio of desired C-to-T editing to unwanted indels (O) and the fractions of C-to-T, C-to-A and C-to-G substitutions (Q) were individually determined at the indicated genomic sites for BE3 (orange), eBE-S1 (faint cyan) and eBE-S3 (cyan). The positions of edited Cs in the sgEMX1, sgFANCF, sgSite2, sgSite4 and sgRNF2 target regions were indicated with the base distal from the PAM set as position 1. Statistical analyses highlighted the significant differences between BE3 (orange) and eBE-S3 (cyan) in indel frequency (L), in the C-to-T editing frequency (N), in the ratio of desired C-to-T editing to unwanted indels (P) and in the fraction of C-to-T substitution (R). (B, D, F, K, M and O) Error bars (±), standard deviations of 3 replicates. (C, E, G, I, L, N, P and R) P values, one-tailed Student's T-test.

Although UGI was fused to nCas9 in BE3, indels could still be observed in reported studies. It was contemplated that additional UGI activity may be useful to further improve the efficiency and fidelity of BE3-mediated base editing. This example then co-expressed UGI in trans with BE3. After co-transfection of UGI in trans with sgRNA/BE3 in 293FT cells (FIG. 16A), this example applied deep-sequencing to determine the indel and base substitution frequencies at three sgRNA target sites. Compared to BE3 alone, co-expressing BE3 and UGI in trans evidently reduced the indel frequencies (FIGS. 16B and 16C, P<10$^{-6}$) and promoted C-to-T editing frequencies at target bases (FIGS. 16D and 16E, P<10$^{-5}$). Specifically, the expression level of UGI is positively correlated with the ratio of C-to-T editing to indels (FIG. 16F). When a high level of free UGI was present, the ratio of desired base editing to unwanted indels increased by ~6-fold (FIG. 16G, P<10$^{-4}$). At the same time, the unwanted C-to-A/C-to-G substitutions were also suppressed in most tested cases by free UGI expression, resulting in a significant increase of C-to-T over C-to-A/C-to-G substitutions (FIGS. 16H and 16I, P<10$^{-6}$). It was noticed that the variations among biological replicates were not trivial (FIGS. 16B, 16D and 16F, standard deviation represented by error bar), which could be explained by the different transfection efficiencies among replicates. To exclude the influence of transfection efficiency among different biological replicates, this example normalized the indel frequencies, C-to-T editing frequencies and the ratios of editing to indels induced in BE3/UGI co-expression by those induced in paired BE3 tests. Consistently better base editing effects were observed in BE3/UGI co-expression than in BE3. Moreover, the statistical analysis indicates that those improving effects conferred by high level of free UGI were highly significant (FIGS. 16C, 16E and 16G), P values were all within the range of 10$^{-6}$ to 10$^{-4}$). These results indicated that additional free UGI could reduce AP site formation on single-stranded NTS, thereby suppressing the generation of unwanted indels and C-to-A/C-to-G substitutions and simultaneously increasing the desired C-to-T editing.

This example next sought to set up the enhanced BE (eBE) more conveniently by using a single vector to co-express BE3 with either one (eBE-S1) or three (eBE-S3) copies of 2A-UGI sequence (FIG. 16J). After being transfected into 293FT cells together with five sgRNAs targeting different genomic loci, both eBEs showed lower indel frequencies and higher C-to-T editing frequencies than the original BE3 (FIGS. 16K and 16M); eBE-S3, with three copies of 2A-UGI and the highest level of UGI expression, displayed the most robust and highly significant effect (FIG. 16K-16N, $P<10^{-8}$-$10^{-4}$). Consistently, the ratios of C-to-T editing to indels were elevated when either eBE was used (FIGS. 16O and 16P, $P<10^{-4}$ for eBE-S3). Moreover, the C-to-A/C-to-G substitutions were also suppressed by eBEs and eBE-S3 induced a highly significant increase of C-to-T fractions over C-to-A/C-to-G (FIGS. 16Q and 16R, $P<10^{-9}$). It is worth noting that the nCas9-fused UGI domain is still important for achieving high fidelity of base editing, even when high levels of free UGI is present (data not shown).

Next, this example tested the effects of co-expressing BE3 and free UGI in another cell line, HeLa. Compared to BE3, co-expressing free UGI from a separate or the same vector both induced significantly lower indel frequencies, higher C-to-T editing frequencies, higher ratios of C-to-T editing to indels and higher C-to-T fractions over C-to-A/C-to-G. Taken together, these results indicated that our enhanced base editing system can improve the efficiency and outcome fidelity of base editing, leading to more accurate gene editing at the single-base level.

In conclusion, this example has developed an enhanced base editing system by co-expressing BE3 together with free UGI. This enhanced base editing system not only suppressed the formation of unwanted indels and substitutions but also increased the frequency of C-to-T editing, thereby improving both the fidelity and efficiency of base editing. In conditions such as therapy-related applications of BEs, the 'cleanness' of editing is pursued. This finding thus provides a method to further improve BEs for cleaner editing outcomes. Since new BEs utilizing nCas9s with altered PAMs have recently been developed, this enhanced base editing strategy could also be used to improve the fidelity and efficiency of these newly emerged BEs.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A fusion protein comprising a first fragment comprising a cytidine deaminase and a second fragment comprising a catalytically inactive Lachnospiraceae bacterium Cpf1 (dLbCpf1), wherein the dLbCpf1 comprises the amino acid sequence of SEQ ID NO:5, wherein the cytidine deaminase is an apolipoprotein B mRNA editing enzyme, catalytic polypeptide-like (APOBEC) protein selected from the group consisting of a wild-type rat APOBEC1, a wild-type human APOBEC3A, a wild-type human activation-induced (cytidine) deaminase (AID), and a variant comprising an amino acid sequence that is at least 95% identical to SEQ ID NO: 1 or 4.

2. The fusion protein of claim 1, wherein the cytidine deaminase has at least 95% sequence identity to the polypeptide of SEQ ID NO:1 and comprises one or two substitutions that correspond to substitutions in the polypeptide of SEQ ID NO:1 selected from the group consisting of W90Y and R126E.

3. The fusion protein of claim 1, wherein the APOBEC protein is the wild-type human APOBEC3A or a variant comprising an amino acid sequence that is at least 95% identical to SEQ ID NO: 4.

4. The fusion protein of claim 1, further comprising at least one uracil DNA glycosylase inhibitor (UGI).

5. The fusion protein of claim 4, which comprises at least two UGIs, wherein at least one of the UGIs is separated from the first fragment and the second fragment by a protease cleavage site.

6. The fusion protein of claim 1, further comprising one or more nuclear localization sequences (NLS).

7. The fusion protein of claim 1, which comprises, from the N-terminus to the C-terminus, a first NLS, the first fragment, the second fragment, a second NLS, a first UGI, a third NLS, a self-cleaving peptide, and a second UGI.

8. The fusion protein of claim 7, further comprising a fourth NLS between the second fragment and the first UGI.

9. The fusion protein of claim 8, further comprising an additional self-cleaving peptide and a third UGI between the self-cleaving peptide and the second UGI, wherein the third UGI is at the C-terminus of the self-cleaving peptide and the additional self-cleaving peptide is at the C-terminus of the third UGI.

10. A method of editing a cytosine on a nucleic acid in a sample, comprising contacting the sample with a suitable guide RNA and the fusion protein of claim 1.

11. The method of claim 10, wherein the cytidine deaminase is the wild-type human APOBEC3 or a variant comprising an amino acid sequence that is at least 95% identical to SEQ ID NO: 4.

12. The method of claim 10, wherein the cytidine deaminase is the wild-type rat APOBEC1 or a variant comprising an amino acid sequence that is at least 95% identical to SEQ ID NO: 1.

13. The method of claim 10, wherein the cytidine deaminase has at least 95% sequence identity to the polypeptide of SEQ ID NO: 1 and comprises one or two substitutions that correspond to substitutions in the polypeptide of SEQ ID NO: 1 selected from the group consisting of W90Y and R126E.

* * * * *

SEQUENCE LISTING

```
<160> NUMBER OF SEQ ID NOS: 150

<210> SEQ ID NO 1
<211> LENGTH: 229
<212> TYPE: PRT
<213> ORGANISM: Artificial Sequence
<220> FEATURE:
<223> OTHER INFORMATION: Synthetic

<400> SEQUENCE: 1

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
```

```
              180                 185                 190
Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
        210                 215                 220

Ala Thr Gly Leu Lys
225

<210> SEQ ID NO 2
<211> LENGTH: 229
<212> TYPE: PRT
<213> ORGANISM: Artificial Sequence
<220> FEATURE:
<223> OTHER INFORMATION: Synthetic

<400> SEQUENCE: 2

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Tyr Ser Pro Cys Gly Glu Cys
                85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Glu Asn Arg
            115                 120                 125

Gln Gly Leu Arg Asp Leu Ile Ser Ser Gly Val Thr Ile Gln Ile Met
        130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
        210                 215                 220

Ala Thr Gly Leu Lys
225

<210> SEQ ID NO 3
<211> LENGTH: 229
<212> TYPE: PRT
<213> ORGANISM: Artificial Sequence
<220> FEATURE:
<223> OTHER INFORMATION: Synthetic

<400> SEQUENCE: 3

Met Ser Ser Glu Thr Gly Pro Val Ala Val Asp Pro Thr Leu Arg Arg
1               5                   10                  15
```

```
Arg Ile Glu Pro His Glu Phe Glu Val Phe Asp Pro Arg Glu Leu
             20                  25                  30

Arg Lys Glu Thr Cys Leu Leu Tyr Glu Ile Asn Trp Gly Gly Arg His
         35                  40                  45

Ser Ile Trp Arg His Thr Ser Gln Asn Thr Asn Lys His Val Glu Val
 50                  55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Tyr Ser Pro Cys Gly Glu Cys
                 85                  90                  95

Ser Arg Ala Ile Thr Glu Phe Leu Ser Arg Tyr Pro Val Thr Leu
            100                 105                 110

Phe Ile Tyr Ile Ala Arg Leu Tyr His His Ala Asp Pro Glu Asn Arg
            115                 120                 125

Gln Gly Leu Glu Asp Leu Ile Ser Ser Gly Val Thr Ile Gln Ile Met
            130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro His Ile Leu Trp
210                 215                 220

Ala Thr Gly Leu Lys
225

<210> SEQ ID NO 4
<211> LENGTH: 199
<212> TYPE: PRT
<213> ORGANISM: Artificial Sequence
<220> FEATURE:
<223> OTHER INFORMATION: Synthetic

<400> SEQUENCE: 4

Met Glu Ala Ser Pro Ala Ser Gly Pro Arg His Leu Met Asp Pro His
 1               5                  10                  15

Ile Phe Thr Ser Asn Phe Asn Asn Gly Ile Gly Arg His Lys Thr Tyr
             20                  25                  30

Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
 50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
            130                 135                 140
```

```
Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 5
<211> LENGTH: 1237
<212> TYPE: PRT
<213> ORGANISM: Artificial Sequence
<220> FEATURE:
<223> OTHER INFORMATION: Synthetic

<400> SEQUENCE: 5

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
290                 295                 300
```

```
Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
            325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
            405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
            485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
            565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
            645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
```

-continued

```
            725                 730                 735
Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
            770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                    805                 810                 815

Arg Val Leu Leu Lys His Asp Asp Asn Pro Tyr Val Ile Gly Ile Ala
                    820                 825                 830

Arg Gly Glu Arg Asn Leu Leu Tyr Ile Val Val Asp Gly Lys Gly
                    835                 840                 845

Asn Ile Val Glu Gln Tyr Ser Leu Asn Glu Ile Ile Asn Asn Phe Asn
            850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                    885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Ala Asp Leu Asn
            915                 920                 925

Ser Gly Phe Lys Asn Ser Arg Val Lys Val Glu Lys Gln Val Tyr Gln
            930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                    965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
            995                 1000                1005

Gly Phe Val Asn Leu Leu Lys  Thr Lys Tyr Thr Ser  Ile Ala Asp
            1010                1015                1020

Ser Lys  Lys Phe Ile Ser Ser  Phe Asp Arg Ile Met  Tyr Val Pro
            1025                1030                1035

Glu Glu  Asp Leu Phe Glu Phe  Ala Leu Asp Tyr Lys  Asn Phe Ser
            1040                1045                1050

Arg Thr  Asp Ala Asp Tyr Ile  Lys Lys Trp Lys Leu  Tyr Ser Tyr
            1055                1060                1065

Gly Asn  Arg Ile Arg Ile Phe  Arg Asn Pro Lys Lys  Asn Asn Val
            1070                1075                1080

Phe Asp  Trp Glu Glu Val Cys  Leu Thr Ser Ala Tyr  Lys Glu Leu
            1085                1090                1095

Phe Asn  Lys Tyr Gly Ile Asn  Tyr Gln Gln Gly Asp  Ile Arg Ala
            1100                1105                1110

Leu Leu  Cys Glu Gln Ser Asp  Lys Ala Phe Tyr Ser  Ser Phe Met
            1115                1120                1125

Ala Leu  Met Ser Leu Met Leu  Gln Met Arg Asn Ser  Ile Thr Gly
            1130                1135                1140
```

-continued

```
Arg Thr Asp Val Ala Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Gly Ser Pro Lys Lys
    1220                1225                1230

Lys Arg Lys Val
    1235

<210> SEQ ID NO 6
<211> LENGTH: 1316
<212> TYPE: PRT
<213> ORGANISM: Artificial Sequence
<220> FEATURE:
<223> OTHER INFORMATION: Synthetic

<400> SEQUENCE: 6

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255
```

```
Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670
```

```
Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Ala Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Ala Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
```

```
                1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Ala Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn Gly
    1295                1300                1305

Ser Pro Lys Lys Lys Arg Lys Val
    1310                1315

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Pro Lys Lys Lys Arg Lys Val
1               5

<210> SEQ ID NO 8
<211> LENGTH: 83
<212> TYPE: PRT
<213> ORGANISM: Artificial Sequence
<220> FEATURE:
<223> OTHER INFORMATION: Synthetic

<400> SEQUENCE: 8

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
                20                  25                  30

Gly Asn Lys Pro Glu Ser Asp Ile Leu Val His Thr Ala Tyr Asp Glu
            35                  40                  45
```

```
Ser Thr Asp Glu Asn Val Met Leu Leu Thr Ser Asp Ala Pro Glu Tyr
     50                  55                  60

Lys Pro Trp Ala Leu Val Ile Gln Asp Ser Asn Gly Glu Asn Lys Ile
 65                  70                  75                  80

Lys Met Leu

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Gly Ser Gly Ala Thr Asn Phe Ser Leu Leu Lys Gln Ala Gly Asp Val
 1               5                  10                  15

Glu Glu Asn Pro Gly Pro
             20

<210> SEQ ID NO 10
<211> LENGTH: 23
<212> TYPE: PRT
<213> ORGANISM: Artificial Sequence
<220> FEATURE:
<223> OTHER INFORMATION: Synthetic

<400> SEQUENCE: 10

Gly Ser Gly Gln Cys Thr Asn Tyr Ala Leu Leu Lys Leu Ala Gly Asp
 1               5                  10                  15

Val Glu Ser Asn Pro Gly Pro
             20

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Gly Ser Gly Gln Cys Thr Asn Tyr Ala Leu Leu Lys Leu Ala Gly Asp
 1               5                  10                  15

Val Glu Ser Asn Pro Gly Pro
             20

<210> SEQ ID NO 12
<211> LENGTH: 199
<212> TYPE: PRT
<213> ORGANISM: Artificial Sequence
<220> FEATURE:
<223> OTHER INFORMATION: Synthetic

<400> SEQUENCE: 12

Met Glu Ala Ser Pro Ala Ser Gly Pro Arg His Leu Met Asp Pro His
 1               5                  10                  15

Ile Phe Thr Ser Asn Phe Asn Asn Gly Ile Gly Arg His Lys Thr Tyr
             20                  25                  30

Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
     50                  55                  60

Gly Phe Tyr Gly Arg His Ala Glu Leu Arg Phe Leu Asp Leu Val Pro
```

```
                65                  70                  75                  80
Ser Leu Gln Leu Asp Pro Ala Gln Ile Tyr Arg Val Thr Trp Phe Ile
                    85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
                115                 120                 125

Ile Phe Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
                195

<210> SEQ ID NO 13
<211> LENGTH: 199
<212> TYPE: PRT
<213> ORGANISM: Artificial Sequence
<220> FEATURE:
<223> OTHER INFORMATION: Synthetic

<400> SEQUENCE: 13

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
                35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                    85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
                115                 120                 125

Ile Tyr Asp Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
                195

<210> SEQ ID NO 14
<211> LENGTH: 199
<212> TYPE: PRT
```

<213> ORGANISM: Artificial Sequence
<220> FEATURE:
<223> OTHER INFORMATION: Synthetic

<400> SEQUENCE: 14

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
            85                  90                  95

Ser Trp Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
            165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 15
<211> LENGTH: 199
<212> TYPE: PRT
<213> ORGANISM: Artificial Sequence
<220> FEATURE:
<223> OTHER INFORMATION: Synthetic

<400> SEQUENCE: 15

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
            85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125
```

```
Ile Tyr Tyr Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 16
<211> LENGTH: 199
<212> TYPE: PRT
<213> ORGANISM: Artificial Sequence
<220> FEATURE:
<223> OTHER INFORMATION: Synthetic

<400> SEQUENCE: 16

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Phe Glu Asp Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 17
<211> LENGTH: 199
<212> TYPE: PRT
<213> ORGANISM: Artificial Sequence
<220> FEATURE:
<223> OTHER INFORMATION: Synthetic

<400> SEQUENCE: 17

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30
```

```
Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
     50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
             100                 105                 110

Phe Leu Gln Glu Asn Thr His Val Arg Leu Arg Ile Phe Ala Ala Arg
         115                 120                 125

Ile Phe Tyr Asp Asp Pro Leu Tyr Lys Glu Ala Leu Gln Met Leu Arg
     130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                 165                 170                 175

Asp Gly Leu Asp Glu His Ser Gln Ala Leu Ser Gly Arg Leu Arg Ala
             180                 185                 190

Ile Leu Gln Asn Gln Gly Asn
         195
```

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
tttagcccca ataatcccca catgtca         27

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
tttagaagca catcaaggac attctaa         27

<210> SEQ ID NO 20
<211> LENGTH: 27
<212> TYPE: DNA
<213> ORGANISM: Artificial Sequence
<220> FEATURE:
<223> OTHER INFORMATION: Synthetic

<400> SEQUENCE: 20
tttgggataa gcacagtttt aaatagt         27

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
tttcttctcc cctctgctgg atacctc						27

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
tttaccttaa tcctctccca gacataa						27

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
tttatttccc ttcagctaaa ataaagg						27

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
tttgtggttg cccaccctag tcattgg						27

<210> SEQ ID NO 25
<211> LENGTH: 27
<212> TYPE: DNA
<213> ORGANISM: Artificial Sequence
<220> FEATURE:
<223> OTHER INFORMATION: Synthetic

<400> SEQUENCE: 25
tttcactctc agtccctggc aggtcgg						27

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
tttgctctca agacccacaa tccaggc						27

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
tttggtttaa acacaccggg ttaata						26

<210> SEQ ID NO 28
<211> LENGTH: 27
<212> TYPE: DNA

<213> ORGANISM: Artificial Sequence
<220> FEATURE:
<223> OTHER INFORMATION: Synthetic

<400> SEQUENCE: 28
tttcctgact gctcactaga tgttgaa                                27

<210> SEQ ID NO 29
<211> LENGTH: 27
<212> TYPE: DNA
<213> ORGANISM: Artificial Sequence
<220> FEATURE:
<223> OTHER INFORMATION: Synthetic

<400> SEQUENCE: 29 tttccctcg tccccctgt gagtacc                                 27

<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30
ttttattctg aagaaacaaa tgacaag                               27

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ttttcataat ccccaaagag gagtcag                               27

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
ttttgccgaa tctagagctc ctctctg                               27

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
tttagcccca ataatcccca catgtca                               27

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
aatccccaca tgtcatggaa ggg                                   23

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
tttatttccc ttcagctaaa ataaagg                                              27

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
cccttcagct aaaataaagg agg                                                  23

<210> SEQ ID NO 37
<211> LENGTH: 27
<212> TYPE: DNA
<213> ORGANISM: Artificial Sequence
<220> FEATURE:
<223> OTHER INFORMATION: Synthetic

<400> SEQUENCE: 37
tttagaagca catcaaggac attctaa                                              27

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
agcacatcaa ggacattcta agg                                                  23

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
tttgtggttg cccaccctag tcattgg                                              27

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
ttgcccaccc tagtcattgg agg                                                  23

<210> SEQ ID NO 41
<211> LENGTH: 27
<212> TYPE: DNA
<213> ORGANISM: Artificial Sequence
<220> FEATURE:

```
<223> OTHER INFORMATION: Synthetic

<400> SEQUENCE: 41
tttgggataa gcacagtttt aaatagt                                           27

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
agcacagttt taaatagttc tgg                                               23

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
tttcttctcc cctctgctgg atacctc                                           27

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
tcccctctgc tggatacctc tgg                                               23

<210> SEQ ID NO 45
<211> LENGTH: 26
<212> TYPE: DNA
<213> ORGANISM: Artificial Sequence
<220> FEATURE:
<223> OTHER INFORMATION: Synthetic

<400> SEQUENCE: 45
tttggtttaa acacaccggg ttaata                                            26

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
ttaaacacac cgggttaata agg                                               23

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
tttgctctca agacccacaa tccaggc                                           27
```

```
<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
tcaagaccca caatccaggc cgg                                            23

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
tttagcccca ataatcccca catgtca                                        27

<210> SEQ ID NO 50
<211> LENGTH: 27
<212> TYPE: DNA
<213> ORGANISM: Artificial Sequence
<220> FEATURE:
<223> OTHER INFORMATION: Synthetic

<400> SEQUENCE: 50
tttagaagca catcaaggac attctaa                                        27

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
tttgggataa gcacagtttt aaatagt                                        27

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
tttcttctcc cctctgctgg atacctc                                        27

<210> SEQ ID NO 53
<211> LENGTH: 27
<212> TYPE: DNA
<213> ORGANISM: Artificial Sequence
<220> FEATURE:
<223> OTHER INFORMATION: Synthetic

<400> SEQUENCE: 53
tttaccttaa tcctctccca gacataa                                        27

<210> SEQ ID NO 54
<211> LENGTH: 27
<212> TYPE: DNA
<213> ORGANISM: Artificial Sequence
<220> FEATURE:
<223> OTHER INFORMATION: Synthetic
```

<400> SEQUENCE: 54
tttggccgct cgagaaccct ctagaag                                27

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
tttagagtct gctctctttg gccgctc                                27

<210> SEQ ID NO 56
<211> LENGTH: 27
<212> TYPE: DNA
<213> ORGANISM: Artificial Sequence
<220> FEATURE:
<223> OTHER INFORMATION: Synthetic

<400> SEQUENCE: 56
tttcttctag agggttctcg agcggcc                                27

<210> SEQ ID NO 57
<211> LENGTH: 27
<212> TYPE: DNA
<213> ORGANISM: Artificial Sequence
<220> FEATURE:
<223> OTHER INFORMATION: Synthetic

<400> SEQUENCE: 57
tttagcccca ataatcccca catgtca                                27

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
tttatttccc ttcagctaaa ataaagg                                27

<210> SEQ ID NO 59
<211> LENGTH: 27
<212> TYPE: DNA
<213> ORGANISM: Artificial Sequence
<220> FEATURE:
<223> OTHER INFORMATION: Synthetic

<400> SEQUENCE: 59
tttagaagca catcaaggac attctaa                                27

<210> SEQ ID NO 60
<211> LENGTH: 27
<212> TYPE: DNA
<213> ORGANISM: Artificial Sequence
<220> FEATURE:
<223> OTHER INFORMATION: Synthetic

<400> SEQUENCE: 60
tttgggataa gcacagtttt aaatagt                                27

<210> SEQ ID NO 61
<211> LENGTH: 27

```
<212> TYPE: DNA
<213> ORGANISM: Artificial Sequence
<220> FEATURE:
<223> OTHER INFORMATION: Synthetic

<400> SEQUENCE: 61
tttcttctcc cctctgctgg ataccte                                27

<210> SEQ ID NO 62
<211> LENGTH: 27
<212> TYPE: DNA
<213> ORGANISM: Artificial Sequence
<220> FEATURE:
<223> OTHER INFORMATION: Synthetic

<400> SEQUENCE: 62
tttaccttaa tcctctccca gacataa                                27

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
tttagcccca ataatcccca catgtca                                27

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
tttagaagca catcaaggac attctaa                                27

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65
tttgggataa gcacagtttt aaatagt                                27

<210> SEQ ID NO 66
<211> LENGTH: 27
<212> TYPE: DNA
<213> ORGANISM: Artificial Sequence
<220> FEATURE:
<223> OTHER INFORMATION: Synthetic

<400> SEQUENCE: 66
tttcttctcc cctctgctgg ataccte                                27

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
```
tttaccttaa tcctctccca gacataa         27

<210> SEQ ID NO 68
<211> LENGTH: 27
<212> TYPE: DNA
<213> ORGANISM: Artificial Sequence
<220> FEATURE:
<223> OTHER INFORMATION: Synthetic

<400> SEQUENCE: 68
tttagcccca ataatcccca catgtca         27

<210> SEQ ID NO 69
<211> LENGTH: 27
<212> TYPE: DNA
<213> ORGANISM: Artificial Sequence
<220> FEATURE:
<223> OTHER INFORMATION: Synthetic

<400> SEQUENCE: 69
tttggccctt ataatcccca catgtca         27

<210> SEQ ID NO 70
<211> LENGTH: 27
<212> TYPE: DNA
<213> ORGANISM: Artificial Sequence
<220> FEATURE:
<223> OTHER INFORMATION: Synthetic

<400> SEQUENCE: 70
tttagcgccc ataatcccca cgtgtca         27

<210> SEQ ID NO 71
<211> LENGTH: 27
<212> TYPE: DNA
<213> ORGANISM: Artificial Sequence
<220> FEATURE:
<223> OTHER INFORMATION: Synthetic

<400> SEQUENCE: 71
tttaatccct ataatcccca catgtca         27

<210> SEQ ID NO 72
<211> LENGTH: 27
<212> TYPE: DNA
<213> ORGANISM: Artificial Sequence
<220> FEATURE:
<223> OTHER INFORMATION: Synthetic

<400> SEQUENCE: 72
tttagccccc ataattccca taggtca         27

<210> SEQ ID NO 73
<211> LENGTH: 27
<212> TYPE: DNA
<213> ORGANISM: Artificial Sequence
<220> FEATURE:
<223> OTHER INFORMATION: Synthetic

<400> SEQUENCE: 73
tttaatcccc atagtcccca catgtca         27

<210> SEQ ID NO 74
<211> LENGTH: 27
<212> TYPE: DNA
<213> ORGANISM: Artificial Sequence

```
<220> FEATURE:
<223> OTHER INFORMATION: Synthetic

<400> SEQUENCE: 74
tttatttccc ttcagctaaa ataaagg                                              27

<210> SEQ ID NO 75
<211> LENGTH: 27
<212> TYPE: DNA
<213> ORGANISM: Artificial Sequence
<220> FEATURE:
<223> OTHER INFORMATION: Synthetic

<400> SEQUENCE: 75
tttttttccc ttgagctaaa ataaatg                                              27

<210> SEQ ID NO 76
<211> LENGTH: 27
<212> TYPE: DNA
<213> ORGANISM: Artificial Sequence
<220> FEATURE:
<223> OTHER INFORMATION: Synthetic

<400> SEQUENCE: 76
tttgtttccc ttcagttaaa atatggg                                              27

<210> SEQ ID NO 77
<211> LENGTH: 27
<212> TYPE: DNA
<213> ORGANISM: Artificial Sequence
<220> FEATURE:
<223> OTHER INFORMATION: Synthetic

<400> SEQUENCE: 77
tttattgccc ttcagctaaa atacagt                                              27

<210> SEQ ID NO 78
<211> LENGTH: 27
<212> TYPE: DNA
<213> ORGANISM: Artificial Sequence
<220> FEATURE:
<223> OTHER INFORMATION: Synthetic

<400> SEQUENCE: 78
tttctttccc tttagctaaa cttcagg                                              27

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
tttttttccc ttcctttaaa aaaaagg                                              27

<210> SEQ ID NO 80
<211> LENGTH: 27
<212> TYPE: DNA
<213> ORGANISM: Artificial Sequence
<220> FEATURE:
<223> OTHER INFORMATION: Synthetic

<400> SEQUENCE: 80
tttagaagca catcaaggac attctaa                                              27
```

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
tttttaaaaa catcaaggat attctaa                                          27

<210> SEQ ID NO 82
<211> LENGTH: 27
<212> TYPE: DNA
<213> ORGANISM: Artificial Sequence
<220> FEATURE:
<223> OTHER INFORMATION: Synthetic

<400> SEQUENCE: 82
tttgtcagca gatcaagtac attctaa                                          27

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
tttaggagta catcaaggaa tttctaa                                          27

<210> SEQ ID NO 84
<211> LENGTH: 27
<212> TYPE: DNA
<213> ORGANISM: Artificial Sequence
<220> FEATURE:
<223> OTHER INFORMATION: Synthetic

<400> SEQUENCE: 84
tttttaacca catcagggac atgctaa                                          27

<210> SEQ ID NO 85
<211> LENGTH: 27
<212> TYPE: DNA
<213> ORGANISM: Artificial Sequence
<220> FEATURE:
<223> OTHER INFORMATION: Synthetic

<400> SEQUENCE: 85
ttttgaagaa aatcaaggac attgtat                                          27

<210> SEQ ID NO 86
<211> LENGTH: 27
<212> TYPE: DNA
<213> ORGANISM: Artificial Sequence
<220> FEATURE:
<223> OTHER INFORMATION: Synthetic

<400> SEQUENCE: 86
tttgtggttg cccaccctag tcattgg                                          27

<210> SEQ ID NO 87
<211> LENGTH: 27
<212> TYPE: DNA
<213> ORGANISM: Artificial Sequence
<220> FEATURE:
<223> OTHER INFORMATION: Synthetic

```
<400> SEQUENCE: 87
tttctggctg ccctcactac tcattag                                      27

<210> SEQ ID NO 88
<211> LENGTH: 27
<212> TYPE: DNA
<213> ORGANISM: Artificial Sequence
<220> FEATURE:
<223> OTHER INFORMATION: Synthetic

<400> SEQUENCE: 88
tttctggctg ggctccctag tcatcgg                                      27

<210> SEQ ID NO 89
<211> LENGTH: 27
<212> TYPE: DNA
<213> ORGANISM: Artificial Sequence
<220> FEATURE:
<223> OTHER INFORMATION: Synthetic

<400> SEQUENCE: 89
tttgttgttg ctcactgtag tcattgt                                      27

<210> SEQ ID NO 90
<211> LENGTH: 27
<212> TYPE: DNA
<213> ORGANISM: Artificial Sequence
<220> FEATURE:
<223> OTHER INFORMATION: Synthetic

<400> SEQUENCE: 90
tttgttcttg acatccctag tcattgg                                      27

<210> SEQ ID NO 91
<211> LENGTH: 27
<212> TYPE: DNA
<213> ORGANISM: Artificial Sequence
<220> FEATURE:
<223> OTHER INFORMATION: Synthetic

<400> SEQUENCE: 91
tttatagttg cactccctag ggattgg                                      27

<210> SEQ ID NO 92
<211> LENGTH: 27
<212> TYPE: DNA
<213> ORGANISM: Artificial Sequence
<220> FEATURE:
<223> OTHER INFORMATION: Synthetic

<400> SEQUENCE: 92
tttgggataa gcacagtttt aaatagt                                      27

<210> SEQ ID NO 93
<211> LENGTH: 27
<212> TYPE: DNA
<213> ORGANISM: Artificial Sequence
<220> FEATURE:
<223> OTHER INFORMATION: Synthetic

<400> SEQUENCE: 93
tttgtgctaa gcactgtttt aaatggt                                      27

<210> SEQ ID NO 94
```

```
<211> LENGTH: 27
<212> TYPE: DNA
<213> ORGANISM: Artificial Sequence
<220> FEATURE:
<223> OTHER INFORMATION: Synthetic

<400> SEQUENCE: 94
ttttggacaa ggacagtatt aaatagc                                      27

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
ttttgacaaa gcactatttt aaatagt                                      27

<210> SEQ ID NO 96
<211> LENGTH: 27
<212> TYPE: DNA
<213> ORGANISM: Artificial Sequence
<220> FEATURE:
<223> OTHER INFORMATION: Synthetic

<400> SEQUENCE: 96
tttaggataa gcaacatttt aaaaatt                                      27

<210> SEQ ID NO 97
<211> LENGTH: 27
<212> TYPE: DNA
<213> ORGANISM: Artificial Sequence
<220> FEATURE:
<223> OTHER INFORMATION: Synthetic

<400> SEQUENCE: 97
ttttggataa ccacaattta aaaaaat                                      27

<210> SEQ ID NO 98
<211> LENGTH: 27
<212> TYPE: DNA
<213> ORGANISM: Artificial Sequence
<220> FEATURE:
<223> OTHER INFORMATION: Synthetic

<400> SEQUENCE: 98
tttcttctcc cctctgctgg atacctc                                      27

<210> SEQ ID NO 99
<211> LENGTH: 27
<212> TYPE: DNA
<213> ORGANISM: Artificial Sequence
<220> FEATURE:
<223> OTHER INFORMATION: Synthetic

<400> SEQUENCE: 99
tttcttctcc cctctgctgt tttcctc                                      27

<210> SEQ ID NO 100
<211> LENGTH: 27
<212> TYPE: DNA
<213> ORGANISM: Artificial Sequence
<220> FEATURE:
<223> OTHER INFORMATION: Synthetic

<400> SEQUENCE: 100
```
tttcttctcc cctctgctag aagccac                                              27

<210> SEQ ID NO 101
<211> LENGTH: 27
<212> TYPE: DNA
<213> ORGANISM: Artificial Sequence
<220> FEATURE:
<223> OTHER INFORMATION: Synthetic

<400> SEQUENCE: 101
tttcttctcc cctctgatgg agacaac                                              27

<210> SEQ ID NO 102
<211> LENGTH: 27
<212> TYPE: DNA
<213> ORGANISM: Artificial Sequence
<220> FEATURE:
<223> OTHER INFORMATION: Synthetic

<400> SEQUENCE: 102
tttgttcttc gctctgctgt ttacctc                                              27

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
tttattctcc actcccctgt atacctc                                              27

<210> SEQ ID NO 104
<211> LENGTH: 26
<212> TYPE: DNA
<213> ORGANISM: Artificial Sequence
<220> FEATURE:
<223> OTHER INFORMATION: Synthetic

<400> SEQUENCE: 104
tttggtttaa acacaccggg ttaata                                               26

<210> SEQ ID NO 105
<211> LENGTH: 27
<212> TYPE: DNA
<213> ORGANISM: Artificial Sequence
<220> FEATURE:
<223> OTHER INFORMATION: Synthetic

<400> SEQUENCE: 105
tttagtgtaa acacactggg atattaa                                              27

<210> SEQ ID NO 106
<211> LENGTH: 27
<212> TYPE: DNA
<213> ORGANISM: Artificial Sequence
<220> FEATURE:
<223> OTHER INFORMATION: Synthetic

<400> SEQUENCE: 106
tttcgtttaa ccacacagac ttaatga                                              27

<210> SEQ ID NO 107
<211> LENGTH: 27
<212> TYPE: DNA

```
<213> ORGANISM: Artificial Sequence
<220> FEATURE:
<223> OTHER INFORMATION: Synthetic

<400> SEQUENCE: 107
tttagtttat acactccagg taactaa                                              27

<210> SEQ ID NO 108
<211> LENGTH: 27
<212> TYPE: DNA
<213> ORGANISM: Artificial Sequence
<220> FEATURE:
<223> OTHER INFORMATION: Synthetic

<400> SEQUENCE: 108
ttttgtttaa acatactggc ttataaa                                              27

<210> SEQ ID NO 109
<211> LENGTH: 27
<212> TYPE: DNA
<213> ORGANISM: Artificial Sequence
<220> FEATURE:
<223> OTHER INFORMATION: Synthetic

<400> SEQUENCE: 109
tttggtttaa agactcctgg ttaattc                                              27

<210> SEQ ID NO 110
<211> LENGTH: 27
<212> TYPE: DNA
<213> ORGANISM: Artificial Sequence
<220> FEATURE:
<223> OTHER INFORMATION: Synthetic

<400> SEQUENCE: 110
tttaccttaa tcctctccca gacataa                                              27

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
tttaccttaa ttctctccca tacctaa                                              27

<210> SEQ ID NO 112
<211> LENGTH: 27
<212> TYPE: DNA
<213> ORGANISM: Artificial Sequence
<220> FEATURE:
<223> OTHER INFORMATION: Synthetic

<400> SEQUENCE: 112
ttttccttaa tcctctccaa gaaatag                                              27

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
ttttccttaa tcctcaccct cgcataa                                              27
```

<210> SEQ ID NO 114
<211> LENGTH: 27
<212> TYPE: DNA
<213> ORGANISM: Artificial Sequence
<220> FEATURE:
<223> OTHER INFORMATION: Synthetic

<400> SEQUENCE: 114
ttttccttag tcctttctca gacatac                                            27

<210> SEQ ID NO 115
<211> LENGTH: 27
<212> TYPE: DNA
<213> ORGANISM: Artificial Sequence
<220> FEATURE:
<223> OTHER INFORMATION: Synthetic

<400> SEQUENCE: 115
tttcccttaa gcctcaccca gacagag                                            27

<210> SEQ ID NO 116
<211> LENGTH: 27
<212> TYPE: DNA
<213> ORGANISM: Artificial Sequence
<220> FEATURE:
<223> OTHER INFORMATION: Synthetic

<400> SEQUENCE: 116
tttagcccca ataatcccca catgtca                                            27

<210> SEQ ID NO 117
<211> LENGTH: 27
<212> TYPE: DNA
<213> ORGANISM: Artificial Sequence
<220> FEATURE:
<223> OTHER INFORMATION: Synthetic

<400> SEQUENCE: 117
tttcctgact gctcactaga tgttgaa                                            27

<210> SEQ ID NO 118
<211> LENGTH: 27
<212> TYPE: DNA
<213> ORGANISM: Artificial Sequence
<220> FEATURE:
<223> OTHER INFORMATION: Synthetic

<400> SEQUENCE: 118
tttatttccc ttcagctaaa ataaagg                                            27

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119
tttagaagca catcaaggac attctaa                                            27

<210> SEQ ID NO 120
<211> LENGTH: 27
<212> TYPE: DNA
<213> ORGANISM: Artificial Sequence
<220> FEATURE:

<223> OTHER INFORMATION: Synthetic

<400> SEQUENCE: 120
tttgtggttg cccaccctag tcattgg                                              27

<210> SEQ ID NO 121
<211> LENGTH: 27
<212> TYPE: DNA
<213> ORGANISM: Artificial Sequence
<220> FEATURE:
<223> OTHER INFORMATION: Synthetic

<400> SEQUENCE: 121
tttgggataa gcacagtttt aaatagt                                              27

<210> SEQ ID NO 122
<211> LENGTH: 27
<212> TYPE: DNA
<213> ORGANISM: Artificial Sequence
<220> FEATURE:
<223> OTHER INFORMATION: Synthetic

<400> SEQUENCE: 122
tttcactctc agtccctggc aggtcgg                                              27

<210> SEQ ID NO 123
<211> LENGTH: 27
<212> TYPE: DNA
<213> ORGANISM: Artificial Sequence
<220> FEATURE:
<223> OTHER INFORMATION: Synthetic

<400> SEQUENCE: 123
tttcttctcc cctctgctgg atacctc                                              27

<210> SEQ ID NO 124
<211> LENGTH: 26
<212> TYPE: DNA
<213> ORGANISM: Artificial Sequence
<220> FEATURE:
<223> OTHER INFORMATION: Synthetic

<400> SEQUENCE: 124
tttggtttaa acacaccggg ttaata                                               26

<210> SEQ ID NO 125
<211> LENGTH: 27
<212> TYPE: DNA
<213> ORGANISM: Artificial Sequence
<220> FEATURE:
<223> OTHER INFORMATION: Synthetic

<400> SEQUENCE: 125
tttaccttaa tcctctccca gacataa                                              27

<210> SEQ ID NO 126
<211> LENGTH: 27
<212> TYPE: DNA
<213> ORGANISM: Artificial Sequence
<220> FEATURE:
<223> OTHER INFORMATION: Synthetic

<400> SEQUENCE: 126
tttcccctcg tcccccctgt gagtacc                                              27

```
<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
tttgctctca agacccacaa tccaggc                                        27

<210> SEQ ID NO 128
<211> LENGTH: 27
<212> TYPE: DNA
<213> ORGANISM: Artificial Sequence
<220> FEATURE:
<223> OTHER INFORMATION: Synthetic

<400> SEQUENCE: 128
ttttcataat ccccaaagag gagtcag                                        27

<210> SEQ ID NO 129
<211> LENGTH: 27
<212> TYPE: DNA
<213> ORGANISM: Artificial Sequence
<220> FEATURE:
<223> OTHER INFORMATION: Synthetic

<400> SEQUENCE: 129
ttttgccgaa tctagagctc ctctctg                                        27

<210> SEQ ID NO 130
<211> LENGTH: 27
<212> TYPE: DNA
<213> ORGANISM: Artificial Sequence
<220> FEATURE:
<223> OTHER INFORMATION: Synthetic

<400> SEQUENCE: 130
tttagcccca ataatcccca catgtca                                        27

<210> SEQ ID NO 131
<211> LENGTH: 27
<212> TYPE: DNA
<213> ORGANISM: Artificial Sequence
<220> FEATURE:
<223> OTHER INFORMATION: Synthetic

<400> SEQUENCE: 131
tttagaagca catcaaggac attctaa                                        27

<210> SEQ ID NO 132
<211> LENGTH: 27
<212> TYPE: DNA
<213> ORGANISM: Artificial Sequence
<220> FEATURE:
<223> OTHER INFORMATION: Synthetic

<400> SEQUENCE: 132
tttgggataa gcacagtttt aaatagt                                        27

<210> SEQ ID NO 133
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 133
tttcttctcc cctctgctgg atacctc                                          27

<210> SEQ ID NO 134
<211> LENGTH: 27
<212> TYPE: DNA
<213> ORGANISM: Artificial Sequence
<220> FEATURE:
<223> OTHER INFORMATION: Synthetic

<400> SEQUENCE: 134
tttaccttaa tcctctccca gacataa                                          27

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
tttagaagca catcaaggac attctaa                                          27

<210> SEQ ID NO 136
<211> LENGTH: 27
<212> TYPE: DNA
<213> ORGANISM: Artificial Sequence
<220> FEATURE:
<223> OTHER INFORMATION: Synthetic

<400> SEQUENCE: 136
tttcttctcc cctctgctgg atacctc                                          27

<210> SEQ ID NO 137
<211> LENGTH: 27
<212> TYPE: DNA
<213> ORGANISM: Artificial Sequence
<220> FEATURE:
<223> OTHER INFORMATION: Synthetic

<400> SEQUENCE: 137
tttagaagca catcaaggac attctaa                                          27

<210> SEQ ID NO 138
<211> LENGTH: 27
<212> TYPE: DNA
<213> ORGANISM: Artificial Sequence
<220> FEATURE:
<223> OTHER INFORMATION: Synthetic

<400> SEQUENCE: 138
tttcttctcc cctctgctgg atacctc                                          27

<210> SEQ ID NO 139
<211> LENGTH: 27
<212> TYPE: DNA
<213> ORGANISM: Artificial Sequence
<220> FEATURE:
<223> OTHER INFORMATION: Synthetic

<400> SEQUENCE: 139
tttagaagca catcaaggac attctaa                                          27

<210> SEQ ID NO 140
<211> LENGTH: 27
```

```
<212> TYPE: DNA
<213> ORGANISM: Artificial Sequence
<220> FEATURE:
<223> OTHER INFORMATION: Synthetic

<400> SEQUENCE: 140
tttcttctcc tttttgctgg ataccctc                                           27

<210> SEQ ID NO 141
<211> LENGTH: 27
<212> TYPE: DNA
<213> ORGANISM: Artificial Sequence
<220> FEATURE:
<223> OTHER INFORMATION: Synthetic

<400> SEQUENCE: 141
tttagcccca ataatcccca catgtca                                            27

<210> SEQ ID NO 142
<211> LENGTH: 27
<212> TYPE: DNA
<213> ORGANISM: Artificial Sequence
<220> FEATURE:
<223> OTHER INFORMATION: Synthetic

<400> SEQUENCE: 142
tttagcccca ataatcccca catgtca                                            27

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
tttagaagca catcaaggac attctaa                                            27

<210> SEQ ID NO 144
<211> LENGTH: 27
<212> TYPE: DNA
<213> ORGANISM: Artificial Sequence
<220> FEATURE:
<223> OTHER INFORMATION: Synthetic

<400> SEQUENCE: 144
tttagaagca catcaaggac attctaa                                            27

<210> SEQ ID NO 145
<211> LENGTH: 26
<212> TYPE: DNA
<213> ORGANISM: Artificial Sequence
<220> FEATURE:
<223> OTHER INFORMATION: Synthetic

<400> SEQUENCE: 145
tttggtttaa acacaccggg ttaata                                             26

<210> SEQ ID NO 146
<211> LENGTH: 26
<212> TYPE: DNA
<213> ORGANISM: Artificial Sequence
<220> FEATURE:
<223> OTHER INFORMATION: Synthetic

<400> SEQUENCE: 146
```

```
tttggtttaa acacaccggg ttaata                                          26

<210> SEQ ID NO 147
<211> LENGTH: 27
<212> TYPE: DNA
<213> ORGANISM: Artificial Sequence
<220> FEATURE:
<223> OTHER INFORMATION: Synthetic

<400> SEQUENCE: 147
tttaccttaa tcctctccca gacataa                                         27

<210> SEQ ID NO 148
<211> LENGTH: 27
<212> TYPE: DNA
<213> ORGANISM: Artificial Sequence
<220> FEATURE:
<223> OTHER INFORMATION: Synthetic

<400> SEQUENCE: 148
tttaccttaa tcctctccca gacataa                                         27

<210> SEQ ID NO 149
<211> LENGTH: 27
<212> TYPE: DNA
<213> ORGANISM: Artificial Sequence
<220> FEATURE:
<223> OTHER INFORMATION: Synthetic

<400> SEQUENCE: 149
tttcttctcc cctctgctgg atacctc                                         27

<210> SEQ ID NO 150
<211> LENGTH: 27
<212> TYPE: DNA
<213> ORGANISM: Artificial Sequence
<220> FEATURE:
<223> OTHER INFORMATION: Synthetic

<400> SEQUENCE: 150
tttcttctcc ttttttgctgg atacctc                                        27
```